(12) United States Patent
Srivastava et al.

(10) Patent No.: US 9,909,136 B2
(45) Date of Patent: Mar. 6, 2018

(54) METHODS AND COMPOSITIONS FOR ALTERING LIGNIN COMPOSITION IN PLANTS

(71) Applicant: The Samuel Roberts Noble Foundation, Inc., Ardmore, OK (US)

(72) Inventors: Avinash C. Srivastava, Arcadia, CA (US); Yuhong Tang, Norman, OK (US); Elison Blancaflor, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 45 days.

(21) Appl. No.: 14/710,419

(22) Filed: May 12, 2015

(65) Prior Publication Data

US 2015/0322448 A1 Nov. 12, 2015

Related U.S. Application Data

(60) Provisional application No. 61/992,130, filed on May 12, 2014.

(51) Int. Cl.
*C12N 15/82* (2006.01)
*D01F 9/17* (2006.01)
*D01F 9/16* (2006.01)

(52) U.S. Cl.
CPC ..... *C12N 15/8255* (2013.01); *C12N 15/8218* (2013.01); *D01F 9/17* (2013.01); *D01F 9/16* (2013.01)

(58) Field of Classification Search
None
See application file for complete search history.

(56) References Cited

U.S. PATENT DOCUMENTS 3,990,944 A 11/1976 Gauss et al.
2011/0167514 A1* 7/2011 Brover ................. C07K 14/415
800/278

OTHER PUBLICATIONS

Mehrshahi et al 2010 The Plant Journal 64:267-279.*
Alonso et al., "Genome-Wide insertion mutagenesis of *Arabidopsis thaliana,*" *Science* 301:653-657, 2003.
Bonawitz et al., "The genetics of lignin biosynthesis: connecting genotype to phenotype," *Annu Rev Genet* 44:337-363, 2010.
Broeck et al., "Differential expression of genes involved in $C_1$ metabolism and lignin biosynthesis in wooden core and bast tissues of fibre hemp (*Cannabis sativa* L.)," *Plant Science* 174:205-220, 2008.
Castro et al., "Quantification of plasma S-adenosylmethionine and S-adenosylhomocysteine as their fluorescent $1,N^6$-etheno derivatives: an adaptation of previously described methodology," *J Pharm Biomed Anal* 29:963-968, 2002.
Curtis et al., "A Gateway cloning vector set for high-throughput functional analysis of genes in planta,"*Plant Physiol* 133:462-469, 2003.
Demartini et al., "Changes in composition and sugar release across the annual rings of Populus wood and implications on recalcitrance," *Bioresour Technol* 102:1352-1358, 2011.
Demartini et al., "Small-scale and automatable high-throughput compositional analysis of biomass," *Biotechnol Bioeng* 108:306-312, 2011.
Dozmorov et al., "An associative analysis of gene expression array data," *Bioinformatics* 19:204-211, 2003.
Dubois et al., "Colorimetric method for determination of sugars and related substances," *Anal Chem* 28:350-356, 1956.
Fu et al., "Downregulation of cinnamyl alcohol dehydrogenase (CAD) leads to improved saccharification efficiency in switchgrass," *Bioenergy Res* 4:153-164, 2011.
Fu et al., "Genetic manipulation of lignin reduced recalcitrance and improves ethanol production from switchgrass," *Proc Natl Acad Sci U S A* 108:3803-3808, 2011.
Gong et al., "Ethanol production from renewable resources," *Adv Biochem Eng Biotechnol* 65:207-241, 1999.
Hatfield et al., "Using the Acetyl Bromide Assay to determine lignin concentrations in herbaceous plants: some cautionary notes," *J Agri Food Chem* 47:628-632, 1999.
Irizarry et al., "Exploration, normalization, and summaries of high density oligonucleotide array probe level data," *Biostatistics* 4:249-264, 2003.
Jeoh et al., "Cellulase digestibility of pretreated biomass is limited by cellulose accessibility," *Biotechnol Bioeng* 98:112-122; 2007.
Lapierre et al., "New insights into the molecular architecture of hardwood lignins by chemical degradative methods," *Res Chem Intermed* 21:397-412, 1995.
Li et al., "The maize brown midrib4 (bm4) gene encodes a functional folylpolyglutamate synthase," *Plant J* 81:493-504, 2015.
Li et al., "Model-based analysis of oligonucleotide arrays: expression index computation and outlier detection," *Proc Natl Acad Sci U S A* 98:31-36, 2001.
Mershashi et al., "Functional analysis of folate polyglutamylation and its essential role in plant metabolism and development," *Plant J* 64:267-279, 2010.
NCBI Reference Sequence: NP_196217.2, "DHFS-FPGS homolog B [*Arabidopsis thaliana*]," Available at: https://www.ncbi.nlm.nih.gov/protein/NP_196217.
Olsson et al., "Fermentation of lignocellulosic hydrolysates for ethanol production," *Enzyme Microb Technol* 18:312-331, 1996.
Pattahil et al., "Immunological approaches to plant cell wall and biomass characterization: glycome profiling," *Methods Mol Biol* 908:61-72, 2012.

(Continued)

*Primary Examiner* — Brent T Page
(74) *Attorney, Agent, or Firm* — Dentons US LLP

(57) ABSTRACT

The invention provides methods for decreasing lignin content in plants by reducing expression of a folylpolyglutamate synthetase 1 (FPGS1) coding sequence in the plant. Also provided are methods for reducing lignin content in a plant by down-regulation of FPGS1 expression in the plant. Nucleic acid molecules for modulation of FPGS1 expression and transgenic plants the same are also provided. Plants described herein may be used, for example, as improved biofuel feedstock and as highly digestible forage crops. Methods for processing plant tissue and for producing biofuels by utilizing such plants are also provided.

27 Claims, 26 Drawing Sheets

(56) References Cited

OTHER PUBLICATIONS

Pattathil et al., "A comprehensive toolkit of plant cell wall glycan-directed monoclonal antibodies," *Plant Physiol* 153:514-525, 2010.
Ramakers et al., "Assumption-free analysis of quantitative real-time polymerase chain reaction (PCR) data," *Neurosci Lett* 339:62-66, 2003.
Rébeillé et al., "Methionine catabolism in *Arabidopsis* cells is initiated by a γ-cleavage process and leads to S-methylcysteine and isoleucine syntheses," *Proc Natl Acad Sci U S A* 103:15687-15692, 2006.
Shen et al., "Functional characterization of the switchgrass (*Panicum virgatum*) R2R3-MYB transcription factor PvMYB4 for improvement of lignocellulosic feedstocks," *New Phytol* 193:121-136, 2012.
Srivastava, "Molecular and functional characterization of tetrahydrofolylpolyglutamate synthase—homolog-B," Presentation to BioEnergy Science Center Group, Oct. 27, 2010.
Srivastava et al., "Laser capture microdissection (LCM) of switchgrass vascular bundles leads to the identification of potential recalcitrance genes," BioEnergy Science Center Retreat 2010, Annual BioEnergy Science Center Meeting, Asheville, North Carolina, Jun. 20-23, 2010.
Srivastava, "Importance of plastidial folylpolyglutamate synthetase (FPGS) isofrom in lignin formation," :Laboratory Seminar, Samuel Roberts Noble Foundation, Ardmore, Oklahoma, Apr. 6, 2011.
Srivastava, "Importance of folypolyglutamate synthetase in cell-wall recalcitrance," Divisional Seminar, Samuel Roberts Noble Foundation, Ardmore, Oklahoma, Mar. 19, 2012.
Srivastava et al., "Collection and analysis of expressed sequence tags derived from laser capture microdissected switchgrass (*Panicum virgatum* L. Alamo) vascular tissues," *Bioenerg Res* 3:278-294, 2010.
Srivastava et al., "The folylpolyglutamate synthetase plastidial isoform is required for postembryonic root development in *Arabidopsis*," *Plant Physiol* 155:1237-1251, 2011.
Srivastava et al., "The plastidial folylpolyglutamate synthetase and root apical meristem maintenance," *Plant Signal Behav* 6:751-754, 2011.
Srivastava et al., "Manipulation of one carbon (C1) metabolism genes for reduced recalcitrance in model plants and bioenergy crops," BioEnergy Science Center Retreat 2012, Annual BioEnergy Science Center Meeting, Chattanooga Loop, Tennessee, Jul. 16-18, 2012.
Srivastava et al., "Repression of folypolyglutamate synthetase alters lignin composition and improves cell wall digestibility in *Arabidopsis*," 24th International Conference on Arabidopsis Research, Sydney, Australia, Jun. 23-28, 2013.
Srivastava et al., "Loss of function of folylpolyglutamate synthetase 1 reduces lignin content and improves cell wall digestibility in *Arabidopsis*," *Biotechnol Biofuels* 8:224, 2015.
Studer et al., "Engineering of a high-throughput screening system to identify cellulosic biomass, pretreatments, and enzyme formulations that enhance sugar release," *Biotechnol Bioeng* 105:231-238, 2010.
Sun et al., "Hydrolysis of lignocellulosic materials for ethanol production: a review," *Bioresour Technol* 83:1-11; 2002.
TAIR Locus: AT5G05980, Available at https://www.arabidopsis.org/servlets/TairObject?name=AT5G05980&type=locus.
Tang et al., "Repression of folylpolyglutamate synthetase alters lignin composition and improves cell wall digestibility in *Arabidopsis*," American Society of Plant Biologists, Plant Biology 2014 Conference, Jul. 12-16, 2014, Portland, Oregon, Final Program pp. 80, poster # P08016-A.
Turner et al., "Vascular patterning," *Arabidopsis Book* 2:e0073; 2003.
Van Acker et al, "Lignin biosynthesis perturbations affect secondary cell wall composition and saccharification yield in *Arabidopsis thaliana*," *Biotechnol Biofuels* 6:46, 2013.
Wyman, "Biomass ethanol: technical progress, opportunities, and commercial challenges," *Annu Rev Energy Environ* 24:189-226, 1999.
Zhu et al., "Virus-induced gene silencing offers a functional genomics platform for studying plant cell wall formation," *Mol Plant* 3:818-833, 2010.

\* cited by examiner

FIG. 2

```
ATGTTTGCAGTTTCGATAGTACCTCGAACCACATCGTGCCGTTTGAGCTCTGCCTTTCTCTGTCAACTCTCGATTCCTCTCA
CTCTTCGGCTCCACCATCACTACCAACACCACCAGCCTCACCTACCATCTCCTCTCTCTTTTCAGgtttccctttctctttc
gctctctgtctctcatattccgagaatctcggagtttcggcatctctgatattctctcttattcgtgtttcagATTCATTCG
TTAAGAAAGCAGATCGACATGGCAGCTCAAGgtttgttattgattttcttattcttctctagctcttcctcacttgatgata
acagtaatcgaatcgagttcacttgttttgttttgttggtgacagGAGGTGATTCATATGAGGAAGCGTTGGCTGCTTTGTC
GTCTTTGATCACGAAACGAAGTCGTGCTGATAAGAGCAATAAAGGGGATCGCTTTGAGTTAGTCTTTGATTATCTCAAGgtt
tctcttttcgattggattctcgtagagttttgaatatttattgcacctttgttttatttctgattgaatacgcttcttgt
aattaattggcagCTACTTGACCTGGAAGAAGACATTTTAAAGATGAATGTTATTCATGTGCCTGGTACCAAAGGCAAGgt
aacaacaacaactttacttttttctggtaaagctcaataaatgatactaaatcatctattgtcaatattaggagttggttttg
ttacttttagttagttagttagatatcttctgaattcgtgtcagcttctacactagttgtgaccgttacgtccttatgactgc
tttgtcagaagaagcctaaggtttttgctctgtgggattagagataacgtttctggactgagtcatcttgagcttttttcca
atttgagtgagtgcgagaagaacattggttttgagatccttgcatgcttggagatgcgtatggtttcatctgatggagtgtc
agttttgcaaaagttgctactttaatcttgactcatatcacttatgtgatagtagatttgggatagcacaaaggaaattgtt
atgaaactagtacttgcttacttttgattcaaaccttcagtgaacttgtttgatgaaagtggttcattgttagcatggctg
attactatctgatccagcacctaacagtattccttttttgtttcttatgtggcatgaagGGATCCACATGTACCTTTACAGAG
TCTATTATTCGAAACTATGGCTTTCGAACTGGACTCTTCACTTCACCTCACCTCATTGATGTCCGGGAAAGATTTCGTTTGG
ATGGgtaagtcttttctaagtttgctgaaaattttgagaaaataaatatatagttacggcctcatataatcaggaaccaac
aatacttcgctagcataatcctgtttttcactctcttttactgagaaatgcttatatctcgcttaatctgatatgtctattt
attgctgcagTGTGGACATAAGTGAAGACGAAATTTTTCGGTATATTCTGGTGGTGCTATAACAGCCTCAAGgtatgttcgtg
agaaaagaaggttcagctatttgattcattgttttgaactcaatatctgtagtttggttatctcgattgactagtagacta
gttgttagtaacgttctgtaaacttggaatcttagtgatgaaagccatatcgaatgtgatcaacatgtaaaacaccctttt
catgaacacttattttgttttctccattttagcttaaaaccatggtgttcagtactgaagtttttggtacttagagaaattgta
ttattggaactattttcatcgaggggtgtgtgatgcggtagagctcatgtatagtgtcttcctgtatcttgttgaagtcac
ctttgttttgcggtctgagtatttcatgatatgaactcataagaatttcaatggtgtgcatagtgcaaattaagatca
tgcttagttttttactcaaatacaaggttgcgacgtatttgatttgcagGAGCAACTAACGAGCAGATACCAATGCCTA
CATATTTCCGCTTCCTTGCATTGCTAGCTTTTAAAATATTTGCTGCAGAAGCAGttgatccagtcttcacttggctgac
tatttttcttactcagtgacatgatagataaactaaatcatgttctcttttattgatataaggggtctgctttttgcttct
ttatgcagGTAGATGCTGCTATATTGGAGGTTGGATTAGCTGGAAAGTTTGATGCCACCAATGCGtatgtttgacctttt
tcagctgaaatgcttttgtctgaacatatccctttacctaacatcctgaattacgaagaggaaagttatatgaaaaccta
gataagatcggaaccccaaatcctaactaatcgtatactgaagtatagtaatatcctcaaaagactccaattactaaaatat
gaataacttccggaccggtgtaagtagagcttctttgtgccaattaagttctctatggtgattactactgacttgttacag
GTTCAGAAACCTGTGGTATGTGGTATTTCTTCACTCGGATATGACCACATGGAAAATTCTAGgtttgtaactggaatcttctc
agcatgccatacgaatatttgtccatgcctctactctttttttcatatcagaactttaaagcatgaagtctatgcttgcat
taaatgagcagacatattttgagttacatttcgttttttataatttctttcttatctgtggaatgcatcacagGTGATACACT
TGGAAAAATTGCTGGTGAGAAGGCTGGAATTTTCAAGgtggctataactctgttaaattgtaacttagcaatattctccata
gttgcctcatcttcattgttcatatttcagCTTGGAGTTCCAGCTTTCACAGTGCCCCAACCTGATGAAGCCATGCGTGTCC
TTGAAGAGAAAGCTTCCGAAACAGAAgtacgctcaattttaattaatgagcactatggtcattaaatttggtagacaatgta
tgtacatatatagtttctgtttatgtcctgcgtggttgattgtagtgctttagatctaccattcttttacgtaaataat
gagaaatcaatgtgtccacaaatatgtgcattagttatagtcccattctagcttttttgatctgtgaagtaagagtgggtg
cttttgcggagatgattcaacattctattgacagatcttgaagtaggtaagtgttttggagaagctttaacatcatattga
cagGTGAATCTCGAAGTGGTGCAGCCACTAACGCAAGGCTGTTAAGTGGTCAGAAACTTGGGCTTGATGGGAACACCAAT
ATGTCAATGCTGGTCTAGCAGTTTCGCTTGCCTCTATCTGGCTTCAGCAAATTGGTAAACTAGAAGTTCCGAGTCGGACTCA
GATGgtaaaatgctcttttccgtctttacgcttactcacagtttgtatcttggcccttctctcatttgtgaatttcatccct
ttttcgacattcttcttcgaattagAGTATTCTGCCTGAGAAATTCATCAAAGGGTTAGCTACAGCGAGTTTGCAAGGACGA
GCACAGGTCGTCCCTGATCAATATACTGAATCTCGGACTTCAGGAGATCTAGTATTTTATCTGGATGGAGCTCACAGTCCAG
AAAGCATGGAAGCATGCGCCAAATGTTTTCGGTTGCGGTTAAGGGAGACAACCAGTCAGGGAGTTCAGGACATTTGGTTAA
TGGCTCTGCAGGATCCTCTCATGATAAATGGTCAAATGAAACCTGTGAACAGgtaaggtccgggtttcgtggtctgtcttgg
atttataaatcatatgagagactgaatgaattcacaggaaaaggattgggtttagagtatcttcttatgtctatgcttgtct
ttctctagttctcagcttttaaatatctgaacgagagcatctggctgctttgcagATATTGTTGTTCAATTGTATGTCAG
TTCGGGACCCAAATCTACTGCTTCCACATCTAAAGAATATGTGCGCAAAATACGgtaagtccgtgagcccttgtgtcttcaa
aagacaaaatgtagaaacagaaaacttggcctgaggtaaaacggatagttagagaagctgaataatggttgatgtagGTGTC
AATTTCAAGAAGCATTGTTTGTACCAAACATGTCGGTGTATCATAAGGTTGGTACAGCAGTCGATTTGCCAGAGAATGATC
CACAGGTTGACTTGTCATGGCAGTTCACACTTCAGAAAGTGTGGGAAAGCCTTGTGCAGAGTGAAAGAGgtagtcctaaatc
tttatgatcatggaataaaatcaacacgtcacaatcgttatctcaacttaactcttcttgtttggtcacgcagATGGAGAAA
AAGATGGTGAAAGTGATGGAAACAGTGAGGTGTTTACTTCACTACCCATGGCAATAAAATGTCTAAGGGACACTGTACATGA
GAGTAGCTCAGCCACACGTTCCAGgtataaaacaaacccctttttctgaacgagtgttcaatccggttttcagttttcgg
ataatgaatagttagcaatgtaagatggctcagggactgtttgtgtgtgcagGTCCTTGTAACTGGTTCGTTACATCTTGTG
GGCGATGTACTGAGATTAATCAGAAAATGA
```

FIG. 3

```
ATGTTTGCAGTTTCGATAGTACCTCGAACCACATCGTGCCGTTTGAGCTCTGCCTTTCTCTGTCAACTCTCGATTCCTCTCA
CTCTTCGGCTCCACCATCACTACCAACACCACCAGCCTCACCTACCATCTCCTCTCTCTTTTCAGgttttccctttctcttttc
gctctctgtctctcatattccgagaatctcggagtttcggcatctctgatattctctcttattcgtgtttcagATTCATTCG
TTAAGAAAGCAGATCGACATGGCAGCTCAAGgtttgttattgatttttcttattcttctctagctcttcctcacttgatgata
acagtaatcgaatcgagttcacttgtttgttttttgttggtgacagGAGGTGATTCATATGAGGAAGCGTTGGCTGCTTTGTC
GTCTTTGATCACGAAACGAAGTCGTGCTGATAAGAGCAATAAAGGGGATCGCTTTGAGTTAGTCTTTGATTATCTCAAGgtt
tctctttttcgattggattctcgtagagttttttgaatattttattgcaccttttgttttattttctgattgaatacgcttcttgt
aattaatttggcagCTACTTGACCTGGAAGAAGACATTTTAAAGATGAATGTTATTCATGTCGCTGGTACCAAAGGCAAGgt
aacaacaacaacttttacttttttctgtaaagctcaataaatgatactaaatcatctattgtcaatattaggagttggttttg
ttactttagttagttagttagatatcttctgaattcgtgtcagcttctacactagttgtgaccgttacgtccttatgactgc
tttgtcagaagaagcctaaggtttttgctctgtggggattagagatacgtttctggactgagtcatcttgagctttttttcca
atttgagtgagtgcgagaagaacattggtttttgagatccttgcatgcttggagatgcgtatggtttcatctgatggagtgtc
agttttgcaaaagttgctactttaatcttgactcatatcacttatgtgatagtagatttgggatagcacaaggaaattgtt
atgaaactagtacttgcttacttttttgattcaaaccttcagtgaacttgtttgatgaaagtggttcattgttagcatggctg
attactatctgatccagcacctaacagtattccttttttgttttcttatgtggcatgaagGGATCCACATGTACCTTTACAGAG
TCTATTATTCGAAACTATGGCTTTCGAACTGGACTCTTCACTTCACCTCACCTCATTGATGTCCGGGAAAGATTTCGTTTGG
ATGGgtaagttttttctaagtttgctgaaaattttgagaaaataaatatatagttaccggccctcatataatcaggaaccaac
aatgacttcgctagcataatcctgttttttcactcttctttactgagaaatgcttatattcgcttaatctgatatgttctattt
attgctgcagTGTGGACATAAGTGAAGAGAAATTTTTGGGATATTTCTGGTGGTGCTATAACAGGCTCAAGgtatgttcgtg
agaaaagaaggttcagctatttgattcatttgttttgaactcaatatctgtagtttggttatctcgattgactagtagacta
gttgttagtaacgttctgtaaacttggaatcttagtgatgaaagccatatagaatgtgataaacatgtaaaacaccctttttt
catgaacacttattttgtttttccattttagcttaaaaccatggtgttcagtactgaagtttggtacttagagaaattgta
ttattggaactattttcatcgaggggtggtagatccggtagcatgtatagtgcttccctgtatcttctgtgaagcac
cttttgttttgcggtctagtacttcatgatatgaactcataagcatttacaatgcggtgctagtggcaaatcaagataca
tgctttagttttttactcaaaatacaaggttgccgactatttgattgcagGAGAGAACTACCGACGGCGATACCAATGCCTA
CATATTTCCGCTTCCTTCCATTGCTAGCTTTAAAATATTTCCTGCAGAAGAGtttgatacccagtcttcacttggttgac
tattttcttactcaagtgacatgatagataaactcaacatcagttccctcttgatataggggttctgctctttgcttct
ttaggcagCTACATGTTCTATATTCGACCTTCGCATTAGCTGCAAATTTCATGCCACCAATGCgtatagttgacccttta
tcagctgaaatgcttttgtctgaacatccctttaactaacatcctgaattacgaaagggaaagttcatatgaaaaccttta
gataagatccgaaccaaatcttacaatcgtatactgaagtatagtaatatcccaaagactccaattactaaaatat
gaataacttttcaggacaggttcaagtagagctttcttgtgctcaataactctcatggtgcttactactgacttgttacag
GTTCGAAACCTGTGCTATGTGGTATTTCTTCACTCGGATATGACCACATGGAAATTCTAGgtttgtaactggaatcttctc
agcatgccatacgaatattgtccatgcctctactcttttttttttcatatcagaactttaaagcatgaagtctatgcttcat
taaatgagcagacatattttgagttacatttcgttttttataattttctttcttatctgtggaatgcatcacagGTGATACACT
TGGAAAAATTGCTGGTGAGAAGGCTGGAATTTTCAAGgtggctataactctgttaaattgtaacttagcaatattctccata
gttgcctcatcttcattcagtattttcagCTTGGAGTTCCAGCGTTTCACAGTGCCCCAACCTGATGAAGCCATGCSTGTCC
TTGAAGAGAAAGCTTCCGAAACAGAAgtacgctcaattttaattaatgagcactatggtcattaaattttggtagacaatgta
tgtacatatatatagttttctgtttatgtcctgcgtggttgattgtagtgcttagatctaccattcttttacggtaaataat
gagaaatcaatgtgtccacaaatatgtgcattagttatagtcccattctagcttttttgatctgtgaaagtaagagtgggtg
cttttgcggagatgattcaacattctattgacagatcttgaaagtagtaagtgttttttgagaagcttaacatcatattga
cagGTGAATCTCGAAGTGGTGCAGCCACTAACGCAAGGCTGTTAAGTGGTCAGAAACTTGGGCTTGATGGGGACACCAAT
ATGTCAATGCTGGTCTAGCAGTTTCGCTTGCCTCTATCTGGCTTCAGCAAATTGGTAAACTAGAAGTTCCGAGTCGGACTCA
GATGgtaaaatgctcttttccgtcttttacgcttactcacagtttgtatcttggccctctctcattgtgaatttcatcct
ttttcgacattcttcttcgaattagAGTATTCTACCTGAGAAATTCATCAAAGGGTTAGCTACAGCGAGTTTGCAAGGACGA
GCACAGGTCGTCCCTGATCAATATACTGAATCTCGGACTTCAGGAGATCTAGTATTTATCTGGATGGAGCTCACAGTCCAG
AAAGCATGGAAGCATGCGCCAAATGGTTTTCGGTTGCGGTTAAGGGAGACAACCAGTCAGGGAGTTCAGGACATTTGGTTAA
TGGCTCTGCAGGATCCTCTCATGATAAATGGTCAAATGAAACCTGTGAACAGgtaaggtccgggtttcgtggtctgtcttgg
attttataaatcatatgagagactgaatgaattcacaggaaaaggattgggtttagagtatcttcttatgtctatgcttgtct
ttctctagtttctcagcttttaaatatctgaacgagagcatctggctgctttgcagATATTGTTGTTCAATTGTATGTCAG
TTCGGGACCCAAATCTACTGCTTCCACATCTAAAGAATATGTCGCAAAATACGgtaagtcgtgagccttgtgtcttcaa
aagacaaaatgtagaaacagaaaacttggcctgagtaaaacggatagttagagagagtcgaataatggttgatgtagGTGTC
AATTTCAAGAAGGCATTGTTTGTACCAAACATGTCGGTGTATCATAAGGTTGGCTACAGCAGCTGATTTGCCAGAGAATGATC
CACAGGTTGACTTGTCATGGCAGTTCACACTTCAGAAAGTGTGGGAAAGCCTTGTGCAGAGTGAAAGAGgtagtcctaaatc
tttatgatcatggaataaaatcaacacgtcacaatcgttatctcaacttaactcttcttgtttggtcacgcagATGGAGAAA
AAGATGGTGAAAGTGATGAAAACAGTGAGGTGTTTACTTCACTACCCATGGCAATAAAAATGTCTAAGGGACACTGTACATGA
GAGTAGCTCAGCCACACGTTTCCAGtatataacaaaccccttttttctgaacgagtgttcaatccgggttttcagtttttcgg
ataatgaatagttagcaatgtaagatggctcagggactgtttgtgtgtgcagGTCCTTGTAACTGGTTCGTTACATCTTGTG
GGCGATGTACTGAGATTAATCAGAAAATGA
```

FIG. 4

```
ATGTTTGCAGTTTCGATAGTACCTCGAACCACATCGTGCCGTTTGAGCTCTGCCTTTCTCTGTCAACTCTCGATTCCTCTCA
CTCTTCGGCTCCACCATCACTACCAACACCACCAGCCTCACCTACCATCTCCTCTCTCTTTTCAGgtttccctttctctttc
gctctctgtctctcatattccgagaatctcggagtttcggcatctctgatattctctcttattcgtgtttcagATTCATTCG
TTAAGAAAGCAGATCGACATGGCAGCTCAAGgtttgttattgattttcttattcttctctagctcttcctcacttgatgata
acagtaatcgaatcgagttcacttgtttgttttgttggtgacagGAGGTGATTCATATGAGGAAGCGTTGGCTGCTTTGTC
GTCTTTGATCACGAAACGAAGTCGTGCTGATAAGAGCAATAAAGGGGATCGCTTTGAGTTAGTCTTTGATTATCTCAAGgtt
tctcttttcgattggattctcgtgagttttgaatatttattgcaccttttgttttattttctgattgaatacgcttcttgt
aattaatttggcagCTACTTGACCTGGAAGAAGACATTTTAAAGATGAATGTTATTCATGTCGCTGGTACCAAAGGCAAGgt
aacaacaacaactttacttttctggtaaagctcaataaatgatactaaatcatctattgtcaatattaggagttggttttg
ttactttagttagttagttagatatcttctgaattcgtgtcagcttctacactagttgtgaccgttacgtccttatgactgc
tttgtcagaagaagcctaaggttttttgctctgtggggattagagatacgtttctggactgagtcatcttgagcttttttcca
atttgagtgagtgcgagaagaacattggttttgagatccttgcatgcttggagatgcgtatggtttcatctgatggagtgtc
agtttttgcaaaagttgctactttaatcttgactcatatctacttatgtgatagtagattggatagcacaaaggaaattgtt
atgaaactagtacttgcttacttttttgattcaaaccttcgtgaacttgtttgatgaaagtggttcattgttagcatggctg
attactatctgatccagcacctaacagtattccttttttgtttcttatgtggcatgaagGGATCCACATGTACCTTTACAGAG
TCTATTATTCGAAACTATGGCTTTCGAACTGGACTCTTCACTTCACCTCACCTCATTGATGTCCGGGAAAGATTTCGTTTGG
ATGGgtaagtttttctaagtttgctgaaaattttgagaaaataaatatatagttaccggcctcatataatcaggaaccaac
aatacttcgctagcataatcctgtttttcactcttcttactgcgagaattgcttatatcgcttaatctgatatgttctattt
attgctgcagTGTGGACATAAGTGAAGAGAAATTTTTGGGATATTTCTGGTGGTGCTATAACAGGCTCAAGgtatgttcgtg
agaaaagaaggttcagctattttgattcatttgttttgaactcaatatctgtagtttggttatctcgattgactagtagacta
gttgttagtaacgttctgtaaacttggaatcttagtgatgaaagccatatagaatgtgataaacatgtaaaacaccccttttt
catgaacacttattttgtttttccatttttagcttaaaaccatggtgttcagtactgaagttttggtacttagagaaattgta
ttattggaactattttcatcgaggggtggtgatgcggtagagctcatgtatagtgtcttccctgtatcttgttgaagtcac
cttttgttttgcggtctgagtatttcatgatatgaactcataagaatttacaatggtgtgcatagttgcaaattaagataca
tgcttttagttttttactcaaaatcaaggttgccgactatttgatttgcagGAGAGAACTAGCAGTAGGTTGCAAATCGCTA
CATATTTGCGCTTCTTGCATTCGTAGCTTTTAAAATATTTGACAGATGCGGgttggatacgagtcttttcgtcttggctgat
tattttctctcctcagtgacatgataagataacatcatgtctctcttattgataatagggtttcgtctttgcttgt
ttatgcagGTAGATGCTCCTATATTGAGGTTGGATTACGCTGGAAAGTTTGATGCCACCAATGCGgtatgttttgaccttttt
tcagctgaaatgctttttgcctgaacatatcccttttacctaacatcctgaattacgaaagcggaaagtctatatgaaaacctta
gataagatcggaaccccaaatccttaactaatcgtatactgaagtatagtaatatcctcaaagactccaattactaaaatat
gaataactttcaggaacgggtgtaagtagagcttcttgtgcctaattaagttccctatggtgattactactgacttgttacag
GTTCAAGAAACCTTGGTATGTGGTATTTCTTCACTCGGATATGACCACATGGAAATTCTAGgtttgtaactggaatcttctc
agcatgcccatacgaatattgctccatgcctctactcttttttccatatcagaacttcaaagcatgaagtctatgcttgcat
taaatgagcagacatattttgagttacattctgttttttataatttcttcttatctgtggaatgcatcacagGTGATACACT
TGGAAAAATTGCTGGTGAGAAGGCTGGAAATTTTCAAGgtggctataactctgttaaattgtaacttagcaatattctccata
gttgcctcatcttcattgttcatatttcagCTTGGAGTTCCAGCTTTCACAGTGCCCCAACCTGATGAAGCCATGCGTGTCC
TTGAAGAGAAAGCTTCCGAAACAGAAgtacgctcaattttttaattaatgagcactatggtcattaaatttgtagacaatgta
tgtacatatatatagtttctgtttatgtcctgcgtggttgattgtagtgcttttagatctaccattcttttacggtaaataat
gagaaatcaatgtgtccaccaatatgtgcattagttatagtcccattctagcttttttgatctgtgaaagtaagagtgggtg
cttttgcggagatgatcaatcatctattgacagatcttgaaagtaggtaagtgtttgtttgagaagcttaacatcatattga
cagGTGAATCTCGAAGTGGTGCAGCCACTAACCGCAAGGCTGTTAAGTGGTCAGAAACTTGGGCTTGATGGGGAACACCAAT
ATGTCAATGCTGGTCTAGCAGTTTCGCTTGCCTCTATCTGGCTTAGCAAATTGGTAAACTAGAAGTTCCGAGTCGGACTCA
GATGgtaaaatgctcttttccgtctttacgcttactcacagtttgtatcttggcccttctctcatttgtgaatttcatccct
ttttcgacattcttcttcgaattagAGTATTCTGCCTGAGAAATTCATCAAAGGGTTAGCTACAGCGAGTTTGCAAGGACGA
GCACAGGTCGTCCCTGATCAATATACTGAATCTCGGACTTCAGGAGATCTAGTATTTTATCTGGATGGAGCTCACAGTCCAG
AAAGCATGGAAGCATGCGCCAAATGGTTTTCGGTTGCGGTTAAGGGAGACAACCAGTCAGGGAGTTCAGGACATTTGGTTAA
TGGCTCTGCAGGATCCTCTCATGATAAATGGTCAAATGAAACCTGTGAACAGgtaaggtccgggtttcgtggtctgtcttgg
atttataaatcatatgagagactgaatgaattcacaggaaaaggattgggtttagagtatcttcttatgtctatgcttgtct
ttctctagtttctcagcttttttaaatatctgaacgagagcatctggctgctttgcagATATTGTTGTTCAATTGTATGTCAG
TTCGGACCCAAATCTACTGCTTCCACATCTAAAGAATATGTGCGCAAAATACGgtaagttcgtgagcccttgtgtcttcaa
aagacaaatgtagaaacagaaacttggcctgaggtaaaacggatagttagagaagctgaataatggttgatgtagGTGTC
AATTTCAAGAAGGCATTGTTTGTACCAAACATGTCGGTGTATCATAAGGTTGGTACAGCAGCTGATTTGCCAGAGAATGATC
CACAGGTTGACTTGTCATGGCAGTTCACACTTCAGAAAGTGTGGGAAAGCCTTGTGCAGAGTGAAAGAGgtagtcctaaatc
tttatgatcatggaataaaatcaacacgtcacaatcgttatctcaacttaactcttcttgtttggtcacgcagATGGAGAAA
AAGATGGTGAAAGTGATGGAAACAGTGAGGTGTTTACTTCACTACCCATGGCAATAAAATGTCTAAGGGACACTGTACATGA
GAGTAGCTCAGCCACACGTTTCCAGgtataaaacaaacccctttttctgaacgagtgttcaatccgggttttcagttttcgg
ataatgaatagtcagcaatgtaagatggctcagggactgtttgtgtgtgcagGTGCTTGTAACTGGTTCGTTACATCTTGTG
GGCGATGTACTGAGATTAATCAGAAAATGA
```

FIG. 11
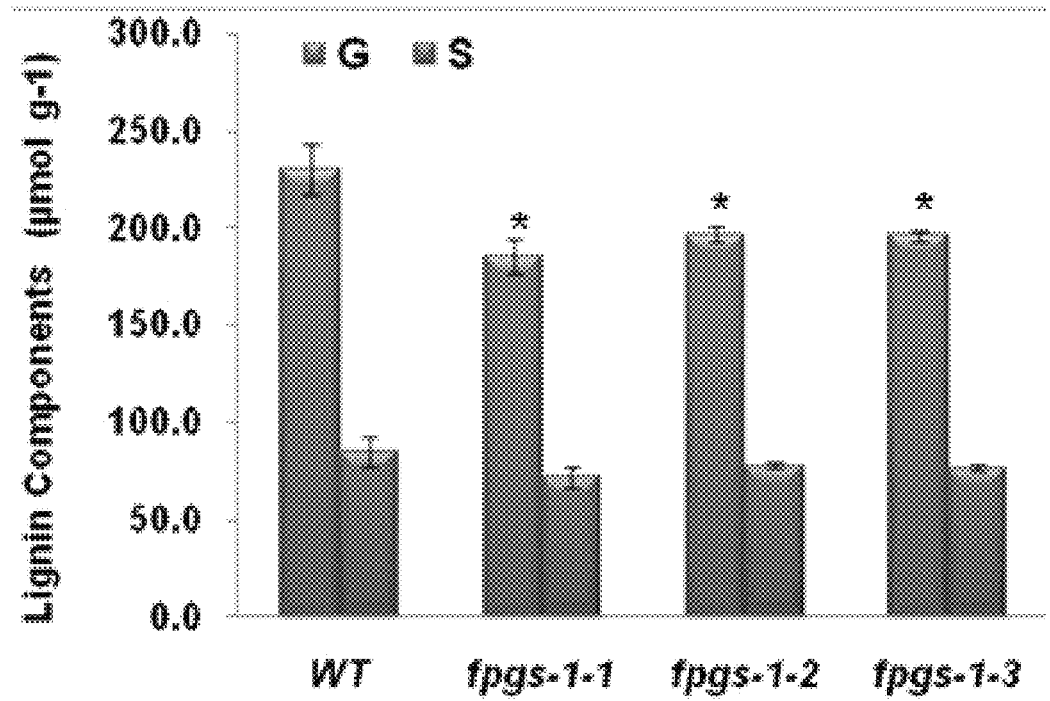
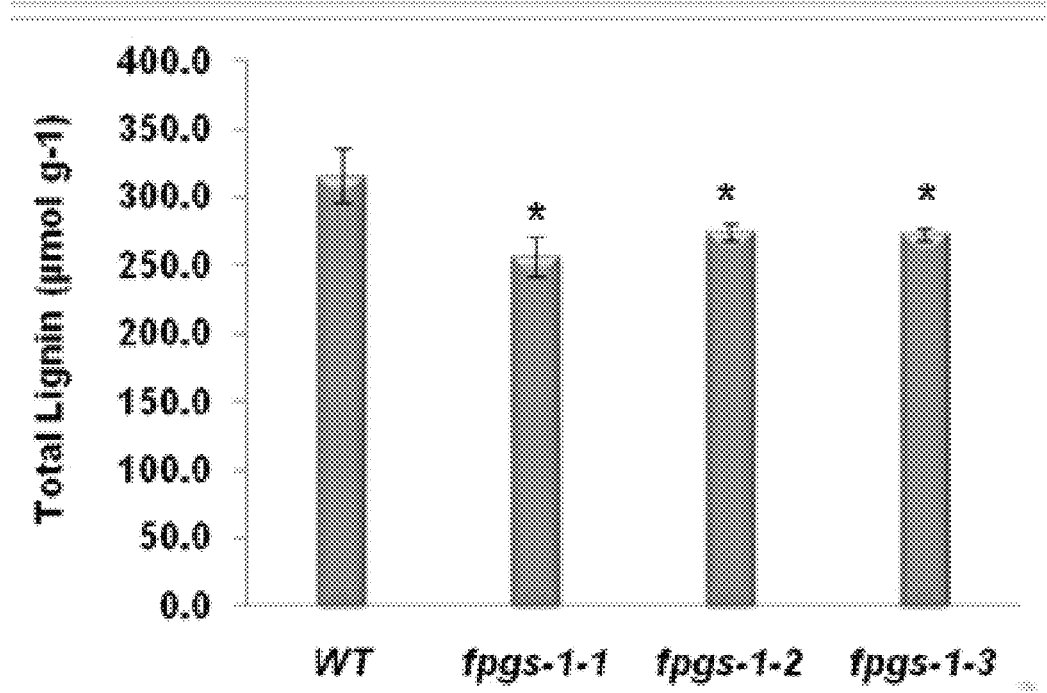

FIG. 16

ATGCGCTCGCATCCCCTCTCGCCGCCTCCTCCTCTCGCCTCGCCTCCACCCAACTAA
CCCATCGGCCGCCATGGCCCTCCACCGCCGCGCGTCGCTCGGGCAGTGCTGTGGCCGGAGTACGA
GGAGGTGCTGGGGCGGCCTCCTCCTGCTCATCACGCAGAGAAGGTGCGCGCACAGCGGCAACGAGGCAAC
CAGTGGGACCTCATGGCCAGGGACCAAGGCACACTACGTCAAGGAGATTCTGGACATGCCGAGGTCA
TCCACGTCGCAGGGACCAAGGCAAGGCACGTCACCTCACCACATTTGATGGATGTCAGGGAGGCGATTCCGGCTAGATGGAGTT
CTTCCACACTGGGCTGTTCACCTCACCACATTTGATGGATGTCAGGGAGGCGATTCCGGCTAGAGAAGACTGATG
GATATATTCTGAAGAGAATGCCAGCCTATTTGAAGTACTTCAGGTCCTGGCGTTGCTCGGCATTCAAGATAATTTCTGCTGAGCA
ATGAGATGTTGCTGTTCTGAGGTTGGCCTTGGAGGGAAGTTGATGCAACTAATGTGGTTGAAGCACCT
GGTAGATGTTGCTGTTCTCGAGGTTGGCCTTGGAGGGAAGTTGATGCAACTAATGTGGTTGAAGCACCT
GTAGTTTGTGGGGTATCTTCGCTTGGATATGATCATATGGAAATTCTTGGAATACGCTTGGAGAATCG
CTGGGAGAAGGCTGGGATTTTCAAGAAGAAGGAGTTCCAGCCTATACCCTCCACAACAAGAAGAGGCAAT
GGTTGCTCTCAAACAAGGTCAACTTCTTGGGACTGAATGCAGGCACTGTGATCCTCTGGTGCCGTAT
CACTTAAAAGGTCAACTTCTTGGGACTGAATGGTGAACACCAATACATAAATGCTGGCCTTGCAGTTGCTT
TGGCTAGTACAGCCTTGAGAGCAGGAGCCATAGGACAGGATACCTCAATCGTACTGATCCCCTACC
AGATCATTTATTAGAGGTCTATCAAATGCTTGTTGCAAGGCGAGCACAGATGTCCAGATCACGA
GTGAATTCAGGAGGCGGCCAGAATTCTCTTGGTTTCTATTGGGCTCACGTCCAGAAGTA
TGGAATATGTGCCAGTGGTTTCCCAGTCACTAATGATGATAAAGAATACCATCCACAGAGCA
GTCTCAGAGTTCGAAGTCTTCAAGAATCCTTCAATGAGATCCGTGAGAGATCCTATGAGACTG
CTTCCGCATCGTCGATGCTAACTCAAAATGCTCACTTGATCGTGCCTATTGTACCAAATC
AATCCGATAACAGCTGGTTCTAGTACATCAGCAGCCTGAACAAAATCGATTTGTCATG
GCAGTGTCACTCCAAACAGTGTGGGAGAAGTTACTTCCACTTGCGATCGAGTGGCTAAGGAAGATAGTGCAATTCCAGT
GACAATAGTAAAGTTTTGCATCTCTTCCACTTGCGATCGAGTGGCTAAGGAAGATAGTGGCAAAACG
GATCTACTTCTTCTTTCAGAACCAGGTCTTGTTACTGGCTCCCTGCATCTGTTGGTGATGTCTTGAGGCT
TATTAAGAAGTGA

FIG. 23
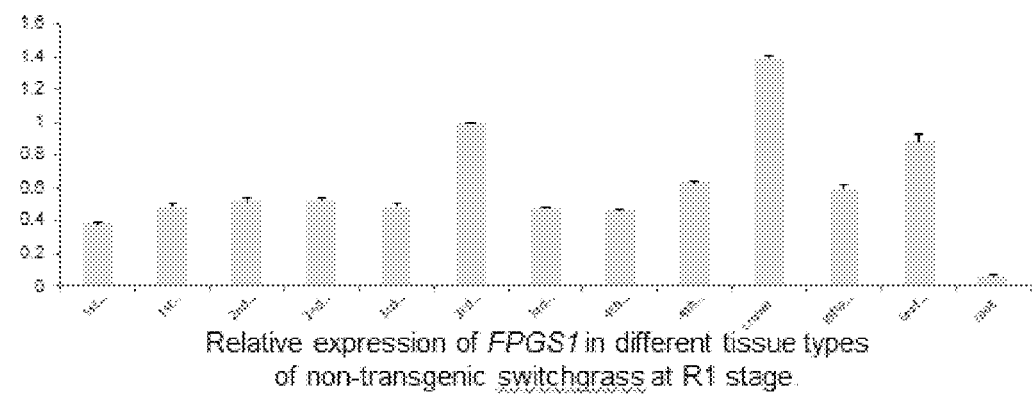
Relative expression of FPGS1 in different tissue types
of non-transgenic switchgrass at R1 stage.
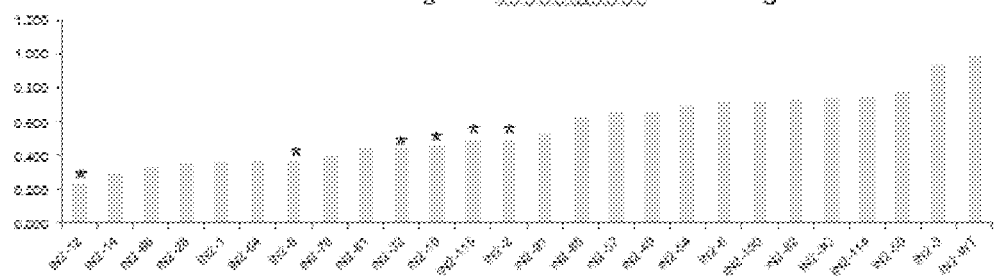
Relative expression of PvFPGS1 in 2nd internode of RNAi lines.
Lines 2, 8, 10, 12, 32, 115 were selected for field trial. These lines
are marked with *

FIG. 26
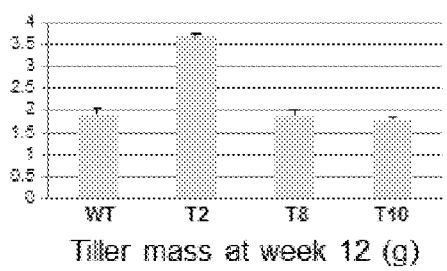
Tiller mass at week 12 (g)
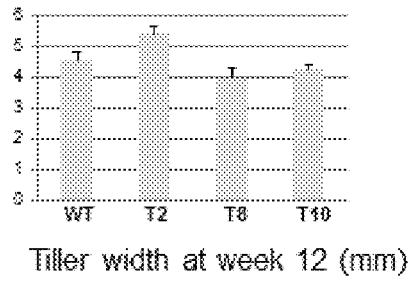
Tiller width at week 12 (mm)
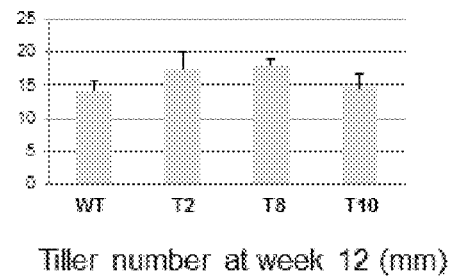
Tiller number at week 12 (mm)
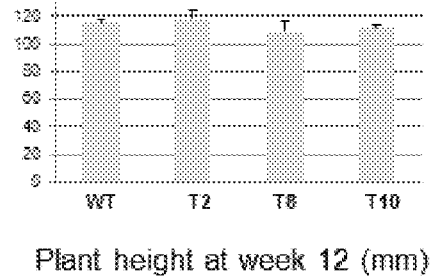
Plant height at week 12 (mm)

METHODS AND COMPOSITIONS FOR ALTERING LIGNIN COMPOSITION IN PLANTS

CROSS REFERENCE TO RELATED APPLICATIONS

This application claims benefit of U.S. Provisional Application No. 61/992,130, filed May 12, 2014, herein incorporated by reference in its entirety.

STATEMENT REGARDING FEDERALLY SPONSORED RESEARCH

This invention was made with Government support under subcontract number 4000064018, Prime Contract No. DE-AC05-00OR22725, awarded by the Department of Energy. The Government has certain rights in this invention.

FIELD OF THE INVENTION

The present invention relates generally to the field of agriculture and plant genetics. More specifically, the invention provides genetically modified plants comprising altered lignin content.

INCORPORATION OF SEQUENCE LISTING

The sequence listing that is contained in the file named "NBLE084US_ST25.txt," which is 44 kilobytes as measured in Microsoft Windows operating system and was created on May 12, 2015, is filed electronically herewith and incorporated herein by reference.

BACKGROUND OF THE INVENTION

Genetic modification of plants has, in combination with conventional breeding programs, led to significant increases in agricultural yield over the last decades. Genetically modified plants may be selected for one or more agronomic traits, for example by expression of enzyme coding sequences (e.g., enzymes that provide herbicide resistance). Genetic manipulation of genes involved in plant growth or yield may enable increased production of valuable commercial crops, resulting in benefits in agriculture and development of alternate energy sources such as biofuels.

Plant biomass content has recently become an intense area of research due to the broad ranging commercial applications for such technology. For example, biofuel is increasingly being considered as a renewable, cleaner alternative to petroleum-based fuels. A variety of fuels may also be produced from sugars and starches as well as from lignocellulosic-based biomass, which constitute the most abundant biomass on earth. However, the types of biofuels that can be efficiently produced from plant mass depend upon the content of component materials such as lignin. Likewise, biomass content dictates the nutritional value of plant mass as animal feed. In particular, high lignin content in plant matter can result in animal feed that is difficult for livestock to digest. Development of plants with modified cell wall composition would have a significant benefit for the production of biofuels and animal feeds and could potentially have a broad range of other beneficial applications. However genetic modification of plants to achieve these goals has not been realized.

SUMMARY OF THE INVENTION

In one aspect, the invention provides a plant or plant part exhibiting artificially down-regulated FPGS1 gene expression, wherein the plant exhibits reduced lignin content. In some embodiments, the plant part is a protoplast, cell, meristem, root, pistil, anther, flower, seed, embryo, stalk or petiole. In some embodiments, the plant comprises a mutated genomic FPGS1 gene, or is defined as an R0 transgenic plant, or is further defined as a progeny plant of any generation of an R0 transgenic plant, wherein the transgenic plant has inherited the selected DNA from the R0 transgenic plant. In another embodiment, the mutated genomic FPGS1 gene is produced by irradiation, T-DNA insertion, transposon insertion, or chemical mutagenesis. In another embodiment, the plant comprises an RNAi construct directed against the FPGS1 gene. In another embodiment, the RNAi construct comprises all or a portion of SEQ ID NO:1 or SEQ ID NO:3 or a complement thereof. In another embodiment, the plant is a forage plant, a biofuel crop, a cereal crop, or an industrial plant. In still another embodiment, the plant is a switchgrass (*Panicum virgatum*) or poplar plant. In a further embodiment, such a plant may be further defined as an R0 transgenic plant or as a progeny plant of any generation of an R0 transgenic plant, wherein the transgenic plant has inherited the selected DNA from the R0 transgenic plant. In another embodiment, the invention provides a plant part of such a plant, such as a protoplast, cell, meristem, root, pistil, anther, flower, seed, embryo, stalk or petiole.

In another aspect, the invention provides a method of reducing lignin content in a plant comprising down-regulating expression of the FPGS1 gene in the plant, wherein the lignin content of the plant is reduced when compared to a plant exhibiting normal FPGS1 expression. In one embodiment, reducing expression of the FPGS1 gene comprises RNAi or mutation of the genomic FPGS1 gene. In another embodiment, the FPGS1 gene is mutated using irradiation, T-DNA insertion, transposon insertion, or chemical mutagenesis. In other embodiments, the plant is a monocotyledonous plant or a dicotyledonous plant. In another embodiment, the reduced lignin content further comprises reduced G lignin content. Another embodiment of the invention provides a plant produced by such a method, wherein the plant comprises reduced lignin content. In other embodiments, the invention provides a seed produced by such a plant or a plant part of such a plant. In another embodiment, such a plant part is further defined as a protoplast, cell, meristem, root, leaf, node, pistil, anther, flower, seed, embryo, stalk or petiole.

In another aspect, the invention provides a method of improving a forage crop or biofuel crop comprising down-regulating expression of the FPGS1 gene in a plant, wherein the plant comprises reduced lignin content and further comprises a beneficial trait when compared to a plant that lacks the reduced expression. In one embodiment, said beneficial trait is selected from the group consisting of increased sugar release, increased forage digestibility, and increased saccharification efficiency. In other embodiments, the plant is a monocotyledonous plant or a dicotyledonous plant. In another embodiment, the reduced lignin content further comprises reduced G lignin content. Another embodiment of the invention provides a plant produced by such a method, wherein said plant comprises reduced lignin content. In other embodiments, the invention provides a seed produced by such a plant or a DNA-containing plant part of such a plant. In another embodiment, such a plant part is further defined as a protoplast, cell, meristem, root, leaf, node, pistil, anther, flower, seed, embryo, stalk or petiole.

In another aspect, the invention provides a method of producing plant biomass, the method comprising: (a) obtaining a plant exhibiting reduced expression of the FPGS1 gene; (b) growing said plant under plant growth conditions to produce plant tissue from the plant; and (c) preparing biomass from said plant tissue. In one embodiment, said preparing biomass comprises harvesting said plant tissue. In another embodiment, such a method further comprises using the biomass for biofuel.

In still another aspect, the invention provides a method of making a commodity product comprising: (a) obtaining a plant exhibiting reduced expression of the FPGS1 gene, wherein the lignin content of the plant is decreased when compared to a plant that lacks the reduced expression; (b) growing the plant under plant growth conditions to produce plant tissue from the plant; and (c) preparing a commodity product from the plant tissue. In one embodiment, preparing the commodity product comprises harvesting the plant tissue. In another embodiment, the commodity product is selected from the group consisting of paper, paper pulp, ethanol, butanol, biodiesel, biogas, silage, carbon fiber, animal feed, and fermentable biofuel feedstock.

In another aspect, the invention provides a method for increasing the digestibility of a forage crop comprising down-regulating FPGS1 gene expression in the plant. In an embodiment, the invention provides a plant produced by such a method, wherein said plant is selected from the group consisting of Pvfpgs1-RNAi lines 2, 8, and 10.

In another aspect, the invention provides a method for increasing the sugar release of a forage crop comprising down-regulating FPGS1 gene expression in the plant. In an embodiment, the invention provides a plant produced by such a method, wherein said plant is selected from the group consisting of Pvfpgs1-RNAi lines 2, 8, and 10.

In a still further aspect, the invention provides a method for increasing the saccharification efficiency of a forage crop comprising down-regulating FPGS1 gene expression in the plant. In an embodiment, the invention provides a plant produced by such a method, wherein said plant is selected from the group consisting of Pvfpgs1-RNAi lines 2, 8, and 10.

BRIEF DESCRIPTION OF THE SEQUENCE LISTING

SEQ ID NO:1—FPGS1 nucleotide sequence in *Arabidopsis*.
SEQ ID NO:2—FPGS1 protein sequence in *Arabidopsis*.
SEQ ID NO:3—FPGS1 nucleotide sequence in switchgrass (*Panicum virgatum*) from which PvFPGS1-RNAi construct was prepared.
SEQ ID NO:4—FPGS1 protein sequence in switchgrass.
SEQ ID NO:5—Gene-specific forward primer PvDFB-RNAi-F used to analyze the PvFPGS1 expression in Switchgrass RNAi lines.
SEQ ID NO:6—Gene-specific reverse primer PvDFB-RNAi-R used to analyze the PvFPGS1 expression in Switchgrass RNAi lines.
SEQ ID NO:7—Affected genomic region for T-DNA insertion line fpgs1-1 (atdfb1-1), shown in FIG. 2.
SEQ ID NO:8—Affected genomic region for T-DNA insertion line fpgs1-2 (atdfb1-2), shown in FIG. 3.
SEQ ID NO:9—Affected genomic region for T-DNA insertion line fpgs1-3 (atdfb1-3), shown in FIG. 4.
SEQ ID NOs:10-39—Sense primer sequences used for genotyping, plasmid construction, and gene expression analysis by RT-qPCR, provided in column 2 of Table 1.
SEQ ID NOs:40-69—Antisense primer sequences used for genotyping, plasmid construction, and gene expression analysis by RT-qPCR, provided in column 3 of Table 1.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2: Shows the affected genomic region for T-DNA insertion line fpgs1-1 (atdfb1-1), corresponding to SEQ ID NO:7. Lowercase letters indicate introns, and uppercase letters indicate exons. The affected region is indicated by shading.

FIG. 3: Shows the affected genomic region for T-DNA insertion line fpgs1-2 (atdfb1-2), corresponding to SEQ ID NO:8. Lowercase letters indicate introns, and uppercase letters indicate exons. The affected region is indicated by shading.

FIG. 4: Shows the affected genomic region for T-DNA insertion line fpgs1-3 (atdfb1-3), corresponding to SEQ ID NO:9. Lowercase letters indicate introns, and uppercase letters indicate exons. The affected region is indicated by shading.

FIG. 11: Shows thioacidolysis analysis of lignin monomers from 35-d-old stems of wild-type and fpgs1 plants. Levels of released S and G units, and total thioacidolysis yields, were compared between wild type and all three mutant alleles of fpgs1 (fpgs1-1, fpgs1-2, fpgs1-3) (FIGS. 7a and b). Mature inflorescence stems of 20 individual plants were pooled and assayed for lignin monomers. Data are the means±SE from five separate assays. *Statistically significant difference; t-test (P<0.05).

FIG. 16: Shows the FPGS1 gene sequence of Switchgrass, corresponding to SEQ ID NO:3. The shaded area indicates the gene region selected for RNAi down-regulation.

FIG. 23: Shows FPGS1 expression in different switchgrass tissues and transgenic FPGS1 RNAi lines.

FIG. 26: Shows greenhouse growth data for FPGS RNAi Lines. Three lines with significant reduction in fpgs1 gene expression selected for greenhouse growth study. Measurements were collected at week 12. The biomass of the RNAi lines were similar or superior to the wild-type. Line T10 exhibited growth traits similar to the parent (WT) plant in the greenhouse and the field.

DETAILED DESCRIPTION OF THE INVENTION

Figure 1:
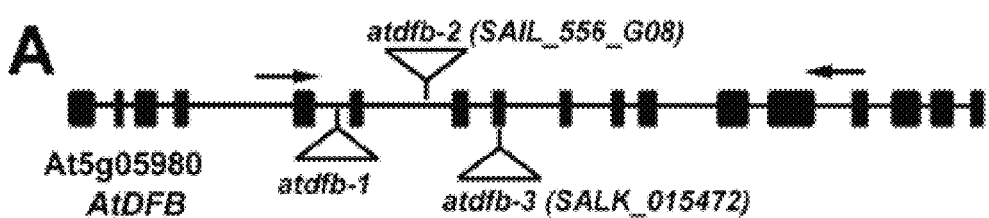
FIG. 1: Shows the insertion sites for T-DNA insertion lines fpgs1-1 (atdfb1-1), fpgs1-2 (atdfb1-2), and fpgs1-3 (atdfb1-3).

The present invention provides a plant exhibiting artificially down-regulated folylpolyglutamate synthetase (FPGS1) gene expression, wherein the plant exhibits reduced lignin content. Also provided are methods of reducing lignin content in a plant comprising down-regulating expression of the FPGS1 gene in the plant, wherein the lignin content of the plant is reduced when compared to a plant exhibiting normal FPGS1 expression. Also provided are methods of improving a forage crop or biofuel crop comprising down-regulating expression of the FPGS1 gene in a plant, wherein the plant comprises reduced lignin content and further comprises a beneficial trait including, but not limited to, increased sugar release, increased forage digestibility, and increased saccharification efficiency when compared to a plant that lacks the reduced expression. The present invention also provides methods of producing plant biomass and making a commodity product comprising: (a) obtaining a plant exhibiting reduced expression of an FPGS gene, wherein the lignin content of the plant is decreased when compared to a plant that lacks the reduced expression; (b) growing the plant under plant growth conditions to produce plant tissue from the plant; and (c) preparing biomass or a commodity product from the plant tissue. Also provided are methods for increasing the digestibility, the sugar release, and the saccharification efficiency of a forage crop comprising down-regulating FPGS1 gene expression in the plant. Previous studies have shown that reduction in lignin content and altered cell wall composition translate into improved saccharification efficiency, which is an important trait for enhanced biofuel production (Fu et al., *Proc. Natl. Acad. Sci. U.S.A.* 108, 3803-3808, 2011; Shen et al., *New Phytol.* 193, 121-136, 2012; Van Acker et al., *Biotechnol. Biofuels,* 6, 46, 2013).

The invention further provides novel methods and compositions for the modification of plant lignin content. A major stumbling block to the use of biomass for production fuels is access to cell wall components that store a large portion of the solar energy converted by the plant. Likewise, plant cell wall components are difficult for animals to digest and thus are not able to be efficiently converted into animal mass for human food (e.g., in grazing livestock). Much effort has been focused on genetic modification of plants to improve digestibility and energy yield from cell wall components. However, modifying the expression of many genes in the lignin synthesis and deposition pathway often has little effect on lignin content and/or results in severe phenotypes that render the resulting plants unusable for commercial processes.

The studies described herein surprisingly demonstrate that altering the expression of FPGS1, such as in an *Arabidopsis* plant or a switchgrass (*Panicum virgatum*) plant, is highly effective in reducing the lignin content of plants. Previous attempts to reduce lignin levels in plants have resulted in growth inhibition, thus making use of these lines for biofuel crops problematic. FPGS1 catalyzes the addition of a glutamate tail to folates to form folylpolyglutamates in the pathways involved in lignin biosynthesis. Knockouts of FPGS1 in *Arabidopsis* lead to reduced levels of methionine and other one-carbon (C1) metabolic intermediates in young seedlings, and as a result, primary roots of the seedlings fail to develop properly and exhibit compromised cell division and cell elongation. Despite these developmental defects, fpgs1 mutants exhibit above-ground biomass comparable to wild-type plants. The present invention demonstrates for the first time that artificially reducing FPGS1 expression in a plant may enable reduction in lignin content in a plant without significantly compromising biomass yields. In accordance with the invention, the methods provided herein may reduce in a plant the content of any specific lignin monomer, such as H lignin, G lignin, or S lignin. In a specific embodiment, the G lignin content is reduced in a plant. Changes in lignin composition typically lead to corresponding modifications in other components of the cell wall and thus mutations in FPGS1 are accompanied by changes in gene expression, metabolites, lignin, and cell wall composition, resulting in plants with enhanced digestibility and sugar release efficiency, important requirements for efficient biofuel processing.

Plants according to the present invention comprising a down-regulated FPGS1 gene exhibit normal growth but have a lower level of stem lignin content. Plants with reduced lignin content are therefore useful in certain biofuel production processes, such as ethanol production. Likewise, reduction in lignin levels directly impacts forage digestibility in a parallel manner to the effects on enzymatic saccharification. Thus, forage plants down-regulated in FPGS1 exhibit improved digestibility.

The methods described herein overcome the previous inability to alter global cell wall composition in the plants. The provided transgenic plants comprise reduced lignin levels that render them useful in the production of improved agricultural products that could not previously have been realized.

In one embodiment, a plant according to the invention comprises down-regulated FPGS1 gene expression. Down-regulation of the FPGS1 gene may be accomplished by introducing a mutation that disrupts the gene by down-regulating FPGS1 expression, by abrogating expression entirely, or by rendering the gene product non-functional. For example, the mutation may be a point mutation, an insertion, a deletion, or any type of mutation known in the art that may result in down-regulation of a gene, and the mutation may be located in a coding (e.g., in an FPGS1 exon) or non-coding portion of the FPGS1 gene (e.g., in the FPGS1 promoter region). Mutations in the FPGS1 gene can be accomplished by any of the methods well known to those in the art including random mutagenesis methods such as irradiation, random DNA integration (e.g., via a transposon), or by using a chemical mutagen. Moreover, in certain aspects, an FPGS1 gene may be mutated using a site-directed mutagenesis approach such as by using a homologous recombination vector, or by irradiation, T-DNA insertion, or chemical mutagenesis. These methods are known in the art, and one of skill will be able to identify such methods as appropriate in light of the present disclosure.

In a further embodiment, a selected DNA that down-regulates FPGS1 expression comprises a DNA molecule capable of expressing a nucleic acid sequence complementary to all or a portion of an FPGS1 gene sequence or an FPGS1 messenger RNA (mRNA). Thus, in some aspects, a transgenic plant may comprise an antisense, RNAi, siRNA, shRNA, or miRNA construct for down-regulation of FPGS1. In a specific embodiment, a plant according to the invention may comprise an RNAi construct comprising all or a portion of SEQ ID NO:1 or SEQ ID NO:3. Such a construct may be engineered to target some or a portion of the FPGS1 gene to achieve down-regulation of the FPGS1 gene. In some embodiments, such a construct may be engineered to target introns or exons, or both, of a particular gene. For example, a transgenic plant may comprise a promoter that expresses a sequence complimentary to all or a portion of an FPGS1 sequence from the plant. In certain specific embodiments, a transgenic plant may comprise a nucleic acid molecule capable of expressing a nucleic acid sequence complementary to all or a portion of an *Arabidopsis* FPGS1 gene (SEQ ID NO:1) or a switchgrass FPGS1, set forth in SEQ ID NO:3. In another embodiment, a transgenic plant in accordance with the invention may express a protein sequence such as set forth in SEQ ID NO:2 or SEQ ID NO:4. Moreover, in certain aspects, the selected DNA that down-regulates FPGS1 expression may comprise a tissue-specific or inducible promoter operably linked to the nucleic acid sequence complimentary to all or part of a plant FPGS1 gene or mRNA. In some cases, the promoter sequence is selected from the group consisting of a developmentally-regulated, organelle-specific, inducible, tissue-specific, constitutive, cell-specific, seed-specific, or germination-specific promoter.

A transgenic plant in accordance with the invention may further comprise a second DNA sequence that down-regulates lignin biosynthesis. For example, in certain embodiments, the second DNA sequence may down-regulate a lignin biosynthesis gene, for example 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase 1 (CCR1), 4-coumarate-CoA ligase (4CL), monolignol-lignin-specific glycosyltransferase, or aldehyde dehydrogenase (ALDH). In certain embodiments, the second DNA may comprise a mutated genomic copy of one or more lignin biosynthesis gene that disrupts expression of the gene or the function of the gene product. A transgenic plant may further comprise a selected DNA that is an antisense or RNAi construct comprising an expressible nucleic acid sequence complimentary to all or part of a lignin biosynthesis gene. In certain embodiments, at least two, at least three, or at least four additional lignin biosynthesis genes may be down-regulated.

Plants according to the invention exhibiting reduced lignin content may comprise any plant for which reduced lignin content may be beneficial, for example a forage plant, a biofuel crop, a cereal crop, or an industrial plant. A variety of plants may be useful in accordance with the present invention. In some embodiments, a plant according to the invention may be a monocotyledonous plant or a dicotyledonous plant. In other embodiments, the plant may be a forage plant, a biofuel crop, a cereal crop, or an industrial plant. In one embodiment, a forage plant may include, but is not limited to, a forage soybean, alfalfa, clover, Bahia grass, Bermuda grass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, reed canarygrass plant, switchgrass (*Panicum virgatum*), or the like. In certain other embodiments, the plant may be a biofuel crop including, but not limited to, switchgrass (*Panicum virgatum*), giant reed (*Arundo donax*), reed canarygrass (*Phalaris arundinacea*), Miscanthus×giganteus, *Miscanthus* sp., sericea lespedeza (*Lespedeza cuneata*), corn, sugarcane, sorghum, millet, ryegrass (*Lolium multiflorum, Lolium* sp.), timothy, *Kochia* (*Kochia scoparia*), soybeans, alfalfa, tomato, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass or poplar. Cereal crops for use according to the present invention include, but are not limited to, maize, rice, wheat, barley, sorghum, millet, oat, rye, triticle, buckwheat, fonio, and quinoa. In certain specific embodiments, the plant may be defined as an *Arabidopsis* or a switchgrass plant having an FPGS1 coding region set forth in SEQ ID NO:1 (*Arabidopsis*), or SEQ ID NO:3 (switchgrass). In certain other specific embodiments, the plant may be defined as an *Arabidopsis* or a switchgrass plant expressing an FPGS1 protein set forth in SEQ ID NO:2 (*Arabidopsis*), or SEQ ID NO:4 (switchgrass).

In some aspects, the invention provides a plant part of a plant comprising down-regulated FPGS1 gene expression. Plant parts in accordance with the invention may include, but are not limited to, a protoplast, cell, meristem, root, pistil, anther, flower, seed, embryo, stalk, or petiole.

In another embodiment, a transgenic or mutated plant produced herein may be further defined as an R0 plant, or as a progeny plant of any generation of an R0 plant, wherein the plant has inherited the selected DNA or mutation from the R0 plant. Moreover, in certain aspects, a progeny plant as described herein may be defined as a progeny plant that has been crossed with a second plant, such as a variety with reduced lodging. In other embodiments, the invention comprises a seed of a plant wherein the seed comprises a mutation or selected DNA described herein. A transgenic cell of such a plant also comprises an embodiment of the invention.

In further embodiments, a transgenic plant, plant part, or plant cell comprising a nucleic acid molecule as described herein is provided. For example, in certain aspects, nucleic acid molecules are provided that down-regulate FPGS1 expression. Plants and plant parts comprising a down-regulated FPGS1 may, in certain aspects, be defined as comprising decreased lignin content and increased fermentable carbohydrate content. In certain aspects, such plants may be used as feedstock for biofuel production. In another embodiment, nucleic acid molecules are provided for expression or overexpression of FPGS1.

The present invention also provides a method of decreasing the lignin content in a plant comprising down-regulating FPGS1 gene expression in the plant. Thus, in certain embodiments, a plant provided herein may be defined as having reduced lignin content relative to a wild-type counterpart. Moreover, in certain embodiments, a plant may be defined as having reduced G lignin content. Plants provided herein comprising reduced lignin content may, in certain aspects, be used in the manufacture of biofuel feedstock (e.g., ethanol, butanol and biodiesel) or paper pulp materials.

In a specific embodiment, the invention provides methods for improving a forage crop or a biofuel crop comprising down-regulating expression of the FPGS1 gene in a plant, wherein the plant comprises reduced lignin content and further comprises a beneficial trait when compared to a plant that lacks the reduced expression. In certain other embodiments, the beneficial trait may comprise increased sugar release, increased forage digestibility, or increased saccharification efficiency. Also provided herein are methods for increasing these traits in a plant of the invention.

In a specific embodiment, the invention provides a method for increasing the digestibility of a forage crop comprising down-regulating FPGS1 gene expression in the plant. For example, in certain embodiments, plants described herein comprise reduced lignin content and have enhanced digestibility. In some cases such plants or parts thereof may be used for livestock forage or in the manufacture of a livestock feed.

In accordance with the invention, a method is provided for the manufacture of a commodity product comprising obtaining a plant or plant part comprising a mutation or a selected DNA that down-regulates a FPGS1 gene and producing a commercial product therefrom. For example, a plant or plant part described herein can be manufactured into a product such as, paper, paper pulp, ethanol, biodiesel, silage, animal feed or fermentable biofuel feedstock.

In yet another aspect, the invention provides a method of producing ethanol comprising: (a) obtaining a plant of a biofuel crop species comprising a selected DNA that down-regulates FPGS1 gene expression in the plant wherein the plant exhibits an increase in fermentable carbohydrates relative to a plant of the same genotype lacking the selected DNA; (b) treating tissue from the plant to render carbohydrates in the tissue fermentable; and (c) fermenting the carbohydrates to produce ethanol.

In yet another aspect, the invention provides a method for processing lignocellulosic biomass from a plant or plant part described herein. In one embodiment the method for processing lignocellulosic biomass from a plant or plant part, may comprise acid and/or enzymatic treatment(s). The enzymatic treatment may comprise treatment with one or more cellulolytic enzymes, such as a cellulase. In another embodiment, the method comprises an acid treatment prior to or during a treatment to render carbohydrates in the plant fermentable. In yet another embodiment, no acid treatment is performed.

Embodiments discussed in the context of methods and/or compositions of the invention may be employed with respect to any other method or composition described herein. Thus, an embodiment pertaining to one method or composition may be applied to other methods and compositions of the invention as well.

I. Plant Transformation Constructs

In certain aspects, the invention provides vectors for plant transformation and/or expression. Vectors used for plant transformation may include, for example, plasmids, cosmids, YACs (yeast artificial chromosomes), BACs (bacterial artificial chromosomes), or any other suitable cloning system, as well as fragments of DNA therefrom. Thus when the term "vector" or "expression vector" is used, all of the foregoing types of vectors, as well as nucleic acid sequences isolated therefrom, are included. Vectors may be used to express a gene coding sequence such as an FPGS1 coding sequence or an RNA sequences such as sequence complementary to all or part of an FPGS1 gene sequence.

It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein that will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue-specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. No. 2004/0049802, the entire disclosure of which is specifically incorporated herein by reference). In one embodiment of the invention, the native promoter of a lignin biosynthesis coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those that comprise sequences predicted to direct optimum expression of the attached gene, i.e., to include a preferred consensus leader sequence that may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16-bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that lignin biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters that direct specific or enhanced expression in certain plant tissues will be known to those of skill in the art in light of the present disclosure. These include, for example, the rbcS promoter, specific for green tissue; the ocs, nos, and mas promoters, which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a lignin biosynthesis coding sequence is used. Alternatively, a heterologous 3' end may enhance the expression of sense or antisense lignin biosynthesis coding sequences. Examples of terminators that may be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product, and which facilitate the transport of the protein into or through intracellular or extracellular membranes, are termed transit (usually into vacuoles, vesicles, plastids, and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Many examples of suitable marker proteins are known to the art and can be employed in the practice of the invention.

Included within the terms "selectable" or "screenable" markers also are genes which encode a "secretable marker" whose secretion can be detected as a means of identifying or selecting for transformed cells. Examples include markers that are secretable antigens that can be identified by antibody interaction, or even secretable enzymes that can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase), and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea, or other ALS inhibiting chemicals (European Patent Application No. 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983), which encodes a catechol dioxygenase that can convert chromogenic catechols; an α-amylase gene (Ikuta et al., 1990); a tyrosinase gene (Katz et al., 1983), which encodes an enzyme capable of oxidizing tyrosine to DOPA and dopaquinone, which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985), which may be employed in calcium-sensitive bioluminescence detection; or a gene encoding for green fluorescent protein (GFP) (Sheen et al., 1995; Haseloff et al., 1997; Reichel et al., 1996; Tian et al., 1997; WO 97/41228). The gene that encodes GFP is also contemplated as a particularly useful reporter gene (Sheen et al., 1995; Haseloff et al., 1997; Reichel et al., 1996; Tian et al., 1997; WO 97/41228). Expression of GFP may be visualized in a cell or plant as fluorescence following illumination by particular wavelengths of light.

II. Antisense and RNAi Constructs

Antisense and RNAi treatments represent one way of altering lignin biosynthesis activity in accordance with the invention (e.g., by down-regulation of FPGS1 gene expression). In particular, constructs comprising a lignin biosynthesis coding sequence, including fragments thereof, in antisense orientation, or combinations of sense and antisense orientation, may be used to decrease or effectively eliminate the expression of a lignin biosynthesis gene in a plant and obtain an improvement in lignin profile as is described herein. Accordingly, this may be used to "knock-out" the function of a lignin biosynthesis coding sequence or homologous sequences thereof.

Techniques for RNAi are well known in the art and are described in, for example, Lehner et al., (2004) and Downward (2004). The technique is based on the fact that double-stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation, or both, within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75, or 100 or more contiguous nucleic acids of the nucleic acid sequence of a lignin biosynthesis gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns, or even exon-intron boundaries of a gene. It is contemplated that the most effective constructs may include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences that are entirely complementary throughout their entire length and have no base mismatches. Other sequences with lower degrees of homology also are contemplated. For example, an RNAi or antisense construct that has limited regions of high homology, but also contains a non-homologous region (e.g., ribozyme; see above) could be designed. Methods for selection and design of sequences that generate RNAi are well known in the art (e.g., Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

III. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species, including biofuel crop species, may be stably transformed, and these cells developed into transgenic plants.

A. Agrobacterium-Mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, alfalfa and potato. Indeed, while Agrobacterium-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990), and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Similarly, *Agrobacterium*-mediated transformation has also proven to be effective in switchgrass. Somleva et al., (2002) describe the creation of approximately 600 transgenic switchgrass plants carrying a bar gene and a uidA gene (beta-glucuronidase) under control of a maize ubiquitin promoter and rice actin promoter, respectively. Both genes were expressed in the primary transformants and could be inherited and expressed in subsequent generations. Addition of 50 to 200 µM acetosyringone to the inoculation medium increased the frequency of transgenic switchgrass plants recovered.

B. Electroporation

To effect transformation by electroporation, one may employ either friable tissues, such as a suspension culture of cells or embryogenic callus, or alternatively, one may transform immature embryos or other organized tissue directly. In this technique, one would partially degrade the cell walls of the chosen cells by exposing them to pectin-degrading enzymes (pectolyases) or mechanically wounding in a controlled manner. Examples of some species that have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987), and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994), and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species that have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

Richards et al., (2001) describe the creation of transgenic switchgrass plants using particle bombardment. Callus was bombarded with a plasmid carrying a sgfp (green fluorescent protein) gene and a bar (bialaphos and Basta tolerance) gene under control of a rice actin promoter and maize ubiquitin promoter respectively. Plants regenerated from bombarded callus were Basta tolerant and expressed GFP. These primary transformants were then crossed with non-transgenic control plants, and Basta tolerance was observed in progeny plants, demonstrating inheritance of the bar gene.

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTOAGAR, GELRITE, and GELGRO, among others, are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos, and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques that may be employed to select target cells include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators, and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

IV. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes, one may employ a means for selecting those cells that are stably transformed. One exemplary embodiment of such a method is to introduce into the host cell, a marker gene that confers resistance to some normally inhibitory agent, such as an antibiotic or herbicide. Examples of antibiotics that may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide that constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT), which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318).

Another example of a herbicide that is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker that may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and similar ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated from about 6 weeks to 10 months after a transformant is identified, depending on the initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 week on media containing the above ingredients along with 10-5 M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques, it would be possible to clone fragments of the host genomic DNA adjacent to an introduced gene.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization, which are modifications of Southern hybridization techniques, one could obtain the same information that is derived from PCR™, e.g., the presence of a gene.

Both PCR™ and Southern hybridization techniques can be used to demonstrate transmission of a transgene to progeny. In most instances, the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™, it is first necessary to reverse-transcribe RNA into DNA, using enzymes such as reverse transcriptase, and then amplify the DNA through the use of conventional PCR™ techniques. In most instances, PCR™ techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting, in which antibodies are used to locate individual gene products that have been separated by electrophoretic techniques. Additional techniques may be employed to absolutely confirm the identity of the product of interest, such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and 14C-acetyl CoA or for anthranilate synthase activity by following loss of fluorescence of anthranilate, to name two.

Very frequently, the expression of a gene product is determined by evaluating the phenotypic results of its expression. These assays also may take many forms including, but not limited to, analyzing changes in the chemical composition, morphology, or physiological properties of the plant. Chemical composition may be altered by expression of genes encoding enzymes or storage proteins that change amino acid composition and may be detected by amino acid analysis, or by enzymes that change starch quantity that may be analyzed by near infrared reflectance spectrometry. Morphological changes may include greater stature or thicker stalks. Most often changes in response of plants or plant parts to imposed treatments are evaluated under carefully controlled conditions termed bioassays.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this, one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Production of Biofuel from Lignocellulosic Biomass

The overall processes for the production of biofuels from plant matter well known in the art. As an example, ethanol production typically involves two steps: saccharification and fermentation. First, saccharification produces fermentable sugars from the cellulose and hemicellulose in the lignocellulosic biomass. Second, those sugars are then fermented to produce ethanol. Thorough, detailed discussion of additional methods and protocols for the production of ethanol from biomass are reviewed in Wyman (1999); Gong et al., (1999); Sun and Cheng, (2002); and Olsson and Hahn-Hagerdal (1996).

A. Pretreatment

Raw biomass is typically pretreated to increase porosity, hydrolyze hemicellulose, remove lignin, and reduce cellulose crystallinity, all in order to improve recovery of fermentable sugars from the cellulose polymer. As a preliminary step in pretreatment, the lignocellulosic material may be chipped or ground. The size of the biomass particles after chipping or grinding is typically between 0.2 and 30 mm. After chipping a number of other pretreatment options may be used to further prepare the biomass for saccharification and fermentation, including steam explosion, ammonia fiber explosion, acid hydrolysis.

1. Steam Explosion

Steam explosion is a very common method for pretreatment of lignocellulosic biomass and increases the amount of cellulose available for enzymatic hydrolysis (U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process causes hemicellulose degradation and lignin transformation. Addition of $H_2SO_4$, $SO_2$, or $CO_2$ to the steam explosion reaction can improve subsequent cellulose hydrolysis, decrease production of inhibitory compounds, and lead to the more complete removal of hemicellulose (Morjanoff and Gray, 1987).

2. Ammonia Fiber Explosion (AFEX)

In AFEX pretreatment, the biomass is treated with approximately 1-2 kg ammonia per kg dry biomass for approximately 30 minutes at pressures of 1.5 to 2 MPa. (U.S. Pat. No. 4,600,590; U.S. Pat. No. 5,037,663; Mes-Hartree, et al., 1988). Like steam explosion, the pressure is then rapidly reduced to atmospheric levels, boiling the ammonia and exploding the lignocellulosic material. AFEX pretreatment appears to be especially effective for biomass with a relatively low lignin content, but not for biomass with high lignin content such as newspaper or aspen chips (Sun and Cheng, 2002).

3. Acid Hydrolysis

Concentrated or dilute acids may also be used for pretreatment of lignocellulosic biomass. $H_2SO_4$ and HCl have been used at high, >70%, concentrations. In addition to pretreatment, concentrated acid may also be used for hydrolysis of cellulose (U.S. Pat. No. 5,972,118). Dilute acids can be used at either high (>160° C.) or low (<160° C.) temperatures, although high temperature is preferred for cellulose hydrolysis (Sun and Cheng, 2002). $H_2SO_4$ and HCl at concentrations of 0.3 to 2% (w/w) and treatment times ranging from minutes to 2 hours or longer can be used for dilute acid pretreatment.

Other pretreatments include alkaline hydrolysis, oxidative delignification, organosolv process, or biological pretreatment; see Sun and Cheng (2002).

B. Saccharification

After pretreatment, the cellulose in the lignocellulosic biomass may be hydrolyzed with cellulase enzymes. Cellulase catalyzes the breakdown of cellulose to release glucose, which can then be fermented into ethanol.

Bacteria and fungi produce cellulases suitable for use in ethanol production (Duff and Murray, 1995). For example, *Cellulomonas fimi* and *Thermomonospora fusca* have been extensively studied for cellulase production. Among fungi, members of the *Trichoderma* genus, and in particular *Trichoderma reesi*, have been the most extensively studied. Numerous cellulases are available from commercial sources as well. Cellulases are usually actually a mixture of several different specific activities. First, endoglucanases create free chain ends of the cellulose fiber. Exoglucanases remove cellobiose units from the free chain ends and beta-glucosidase hydrolyzes cellobiose to produce free glucose.

Reaction conditions for enzymatic hydrolysis are typically around pH 4.8 at a temperature between 45 and 50° C. with incubations of between 10 and 120 hours. Cellulase loading can vary from around 5 to 35 filter paper units (FPU) of activity per gram of substrate. Surfactants like Tween 20, 80, polyoxyethylene glycol or Tween 81 may also be used during enzyme hydrolysis to improve cellulose conversion. Additionally, combinations or mixtures of available cellulases and other enzymes may also lead to increased saccharification.

Aside from enzymatic hydrolysis, cellulose may also be hydrolyzed with weak acids or hydrochloric acid (Lee et al., 1999).

C. Fermentation

Once fermentable sugars have been produced from the lignocellulosic biomass, those sugars may be used to produce ethanol via fermentation. Fermentation processes for producing ethanol from lignocellulosic biomass are extensively reviewed in Olsson and Hahn-Hagerdal (1996). Briefly, for maximum efficiencies, both pentose sugars from the hemicellulose fraction of the lignocellulosic material (e.g., xylose) and hexose sugars from the cellulose fraction (e.g., glucose) should be utilized. *Saccharomyces cerevisiae* are widely used for fermentation of hexose sugars. Pentose sugars, released from the hemicellulose portion of the biomass, may be fermented using genetically engineered bacteria, including *Escherichia coli* (U.S. Pat. No. 5,000,000) or *Zymomonas mobilis* (Zhang et al., 1995). Fermentation with yeast strains is typically optimal around temperatures of 30 to 37° C.

D. Simultaneous Saccharification and Fermentation (SSF)

Cellulase activity is inhibited by its end products, cellobiose and glucose. Consequently, as saccharification proceeds, the build up of those end products increasingly inhibits continued hydrolysis of the cellulose substrate. Thus, the fermentation of sugars as they are produced in the saccharification process leads to improved efficiencies for cellulose utilization (e.g., U.S. Pat. No. 3,990,944). This process is known as simultaneous saccharification and fermentation (SSF), and is an alternative to the above described separate saccharification and fermentation steps. In addition to increased cellulose utilization, SSF also eliminates the need for a separate vessel and processing step. The optimal temperature for SSF is around 38° C., which is a compromise between the optimal temperatures of cellulose hydrolysis and sugar fermentation. SSF reactions can proceed up to 5 to 7 days.

E. Distillation

The final step for production of ethanol is distillation. The fermentation or SSF product is distilled using conventional methods producing ethanol, for instance 95% ethanol.

VII. Definitions

Artificially down-regulated: A gene may be referred to as artificially down-regulated if the normal or natural expression level of the gene is reduced as a result of a non-natural occurrence, such as by induced mutation or genetic modification.

Biofuel crop species: A plant that may be used to provide biomass for production of lignocellulosic-derived ethanol. Examples of such plants include switchgrass (*Panicum virgatum*), giant reed (*Arundo donax*), reed canarygrass (*Phalaris arundinacea*), Miscanthus×giganteus, *Miscanthus* sp., *sericea lespedeza* (*Lespedeza cuneata*), corn, sugarcane, sorghum, millet, ryegrass (*Lolium multiflorum, Lolium* sp.), timothy, *Kochia* (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, and poplar, among others.

Down-regulated: As used herein, down-regulation of a gene refers to a reduction in its expression, whether by natural means or as a result of genetic modification.

FPGS1 coding sequence: As used herein a FPGS1 coding sequence refers to a nucleic acid sequence encoding a functional folylpolyglutamate synthetase.

Expression: The combination of intracellular processes, including transcription and translation undergone by a coding DNA molecule such as a structural gene to produce a polypeptide.

Forage crops: Crops including grasses and legumes used as fodder or silage for livestock production.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence that is not normally present in a given host genome in the genetic context in which the sequence is currently found In this respect, the sequence may be native to the host genome but be rearranged with respect to other genetic sequences within the host sequence. For example, a regulatory sequence may be heterologous in that it is linked to a different coding sequence relative to the native regulatory sequence.

Normal expression: As used herein, "normal expression" is the level of expression of a gene such as FPGS1 that is measured in a measured in a non-transgenic or wild-type plant.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

R0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule that is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation that was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences that are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Characterization of fpgs1 Mutants fpgs1-1 (originally designated as drh2 or atdfb-1) was identified through a forward genetic screen. Two additional T-DNA insertion lines (SALK_015472, and SAIL_556_G08) at the FPGS1 locus (AT5G05980) acquired from *Arabidopsis* Biological Resource Center (ABRC) were also used in this study (Alonso et al., *Science*, 301, 653-657, 2003) and renamed as fpgs1-2 and fpgs1-3 respectively. The insertion sites for these 3 lines are shown in FIG. 1, and the corresponding affected genomic regions for fpgs1-1 (atdfb1-1), fpgs1-2 (atdfb1-2), and fpgs1-3 (atdfb1-3) are shown in FIGS. 2-4, respectively, indicated by shading. Molecular characterization of all of these mutants was conducted. Most of the analyses described here were conducted on the fpgs1-1 mutant unless otherwise indicated. Plants were grown on SunGro-Metro-Mix 350 in 3.5-inch-square pots and cultivated in a controlled-environment chamber (Percival Scientific, IA, USA) at 120 to 140 µmol photons $m^2 s^1$, 14 h of light at 21° C., and 10 h of dark at 19° C. No additional fertilizers were provided in order to maintain homogenous growing conditions.

Example 2

Plasmid Construction

All constructs were made using Gateway™ technology (Invitrogen, Now Life Technologies). The entry clones were obtained using the pENTR-D-TOPO vector (Invitrogen) and expression vectors using the Gateway vectors (Curtis et al., *Plant Physiol.* 133, 462-469, 2003). These were propagated in the *E. coli* strain Top10 (Invitrogen) and DH5α, respectively. The templates used to clone all genes were genomic DNA or cDNA preparations derived from *Arabidopsis thaliana* Col-0. The promoter region 2-kb upstream of the ATG start codon of FPGS1 was amplified using Taq DNA polymerase (Invitrogen) and the gene-specific primers (Table 1). The amplified 2-kb promoter sequences were cloned into pENTR-D-TOPO, and later fused to uidA GUS reporter gene via LR-reaction in the destination vector pMDC162. The constructs were transformed into *Agrobacterium tumefaciens* strain LBA4404. For complementation studies, a 7-kb genomic DNA fragment containing the pAtFPGS1-FPGS1 was amplified using gene-specific primers (Table 1). This construct is comprised of 2-kb upstream of the promoter region of the ATG start codon and 5-kb downstream of the start codon. This region was cloned into pMDC107 binary vectors and transformed into *A. tumefaciens* LBA4404. The fpgs1-1 mutant was then transformed using the Floral-dip method (Clough et al., *Plant J.* 16, 735-743, 1998). Transgenic plants were selected on 25 µg ml$^{-1}$ hygromycin plates and later propagated on soil. Around 10 independent T2 transgenic lines were tested for fluorescence and complementation.

TABLE 1

Primer sequences used for genotyping, plasmid construction, and gene expression analysis by RT-qPCR. Sense primers are provided in column 2 as SEQ ID NOs: 10-39, and antisense primers are provided in column 3 as SEQ ID NOs: 40-69.

| Genes | Sense (5'-3')/Left Primer | Antisense (5'-3')/Right Primer | Usage |
|---|---|---|---|
| SALK_015472 | GGCTTTCGAACTGGACTCTTC (LP) (SEQ ID NO: 10) | TTAAGGATTTGGGTTCCGATC (RP) (SEQ ID NO: 40) | Genotyping |
| SAIL_556_G08 | CTGACCACTTAACAGCCTTGC (LP) (SEQ ID NO: 11) | ATTGGAGGTTGGATTAGGTGG (RP) (SEQ ID NO: 41) | Genotyping |

TABLE 1 -continued

Primer sequences used for genotyping, plasmid construction, and gene expression analysis by RT-qPCR. Sense primers are provided in column 2 as SEQ ID NOs: 10-39, and antisense primers are provided in column 3 as SEQ ID NOs: 40-69.

| Genes | Sense (5'-3')/Left Primer | Antisense (5'-3')/Right Primer | Usage |
|---|---|---|---|
| SALK008883 | CGATGGTTCTCTTCTGCAGTC(LP) (SEQ ID NO: 12) | GGAGGGTTCTCACTTCTCATG(RP) (SEQ ID NO: 42) | Genotyping |
| SAIL510E12 | GGCCCAAGTTGTTTGTATCATC(LP) (SEQ ID NO: 13) | TTCAAGCTTGTCACGATTTCC(RP) (SEQ ID NO: 43) | Genotyping |
| SAIL151E09 | CTCTTTCTGCGGTTCAGACAC(LP) (SEQ ID NO: 14) | TGATCCCTTCAAAACGATCAC(RP) (SEQ ID NO: 44) | Genotyping |
| pFPGS1 | TGTTAAGGTCAAAACATAAACTCCAT (SEQ ID NO: 15) | TCTCTTGTCACTAACATTGCTACACTT (SEQ ID NO: 45) | 2 Kb-Promoter |
| pFPGS-FPGS1 | TGTTAAGGTCAAAACATAAACTCCAT (SEQ ID NO: 16) | TTTTCTGATTAATCTCAGTACATCGC (SEQ ID NO: 46) | 7 kb-Promoter-Gene |
| AtFPGS1 | GGAAAGATTTCGTTTGGATGG (SEQ ID NO: 17) | TGACATACAATTGAACAACAATATC (SEQ ID NO: 47) | Real time |
| AtFPGS2 | GGGGCTTGACCTACACTGA (SEQ ID NO: 18) | CTGCAGGTCCACCACATTG (SEQ ID NO: 48) | Real time |
| AtFPGS3 | GCAAAGAAGAAGAGAAGAGTTTCG (SEQ ID NO: 19) | GAAAACGAACTTGTTTACTTTGGC (SEQ ID NO: 49) | Real time |
| EIF4A2 | GGCTGAATGAAGTTCTCGATGGACAG (SEQ ID NO: 20) | ACGAGAGCCTGGCACTGGAGAAG (SEQ ID NO: 50) | Real time-Control |
| CCoAMT-AT1G67980 | CAGTACATCATGGAAACGTCAGC (SEQ ID NO: 21) | GGTAATACGGCCATCTTCAGG (SEQ ID NO: 51) | Real time |
| Laccase4-AT2G38080 | CACTGGCACGGTGTGAGA (SEQ ID NO: 22) | CATTCACCTAGAACGATGACTTTCT (SEQ ID NO: 52) | Real time |
| COMT-AT1G33030 | CTTCTCCAGGAATTGAGCATG (SEQ ID NO: 23) | GTGTCTCCTGGGAACTCTGG (SEQ ID NO: 53) | Real time |
| C3H-AT2G40890 | GTAACCTTCCTGAAAACAGAGCA (SEQ ID NO: 24) | GCTATTGACAGTGAAGCACCTAGC (SEQ ID NO: 54) | Real time |
| IGMT1-AT1G21100 | GTCTTCCTTAATACCTGGGCAC (SEQ ID NO: 25) | CATCAACTAAAACTTTCACACCTTTG (SEQ ID NO: 55) | Real time |
| HMT3-AT3G22740 | GTTACAAAGGTGCACTTGGATTAC (SEQ ID NO: 26) | CATGAACCCTTGGTGCATC (SEQ ID NO: 56) | Real time |
| MAT3-AT2G36880 | TAGATCCACTTGCAGGGAGATT (SEQ ID NO: 27) | TATCTTCAGGCTTCTTGGTCAAA (SEQ ID NO: 57) | Real time |
| SAMS3-AT3G17390 | TCGTAAAACATGCCGTGAGA (SEQ ID NO: 28) | CCTCCTCTGGCTTCTTGGT (SEQ ID NO: 58) | Real time |
| SAMS2-AT4G01850 | TAATGGCATGGCTCGCAG (SEQ ID NO: 29) | GAATGTCTCTTTCACGATCTTCAG (SEQ ID NO: 59) | Real time |
| SAM-MT-AT1G69526 | GATTCGAGCTTCACGAGATCA (SEQ ID NO: 30) | GAAATGTTTCTGAAACATCCTTGG (SEQ ID NO: 60) | Real time |
| SAM-MT-AT1G66690 | GTCATCGTATCAGAGAGCTTTGTT (SEQ ID NO: 31) | CTCTAAGATACTTCTCTTCCACGGC (SEQ ID NO: 61) | Real time |
| SAM-MT-AT1G55450 | CCATCTTGTTCCAAAACTTGC (SEQ ID NO: 32) | GGTGCGAGATCGAAGTAGTGA (SEQ ID NO: 62) | Real time |
| SAM-MT-AT3G54150 | TGGGCTTGTGGAGCATTAC (SEQ ID NO: 33) | GTCGAAGAAATGGACAGCTTG (SEQ ID NO: 63) | Real time |
| SMT2530-AT4G22530 | CATCGGAATCGCCGAAC (SEQ ID NO: 34) | CCACAGAGTTCTCTCCTCCAAT (SEQ ID NO: 64) | Real time |
| SAM-MT-AT1G15125 | ACCTCTCCCACACTGATTTC (SEQ ID NO: 35) | GTGTAGTGAATCCTGCCTCTG (SEQ ID NO: 65) | Real time |
| SAMS1-AT1G02500 | ACCATCTTCCACTTGAACCC (SEQ ID NO: 36) | GCGTATGAGACCTGAACAAGAG (SEQ ID NO: 66) | Real time |

TABLE 1 -continued

Primer sequences used for genotyping, plasmid construction, and gene expression analysis by RT-qPCR. Sense primers are provided in column 2 as SEQ ID NOs: 10-39, and antisense primers are provided in column 3 as SEQ ID NOs: 40-69.

| Genes | Sense (5'-3')/Left Primer | Antisense (5'-3')/Right Primer | Usage |
|---|---|---|---|
| CCR1-AT1G15950 | CCGGAACAAATGGTGGAG (SEQ ID NO: 37) | CAATACCAATTCTTGGTGTTTTG (SEQ ID NO: 67) | Real time |
| PAL3-AT5G04230 | CCGCTTCAGAAACCTAAACAAG (SEQ ID NO: 38) | GCTAGACGAGTGTTATCCATGG (SEQ ID NO: 68) | Real time |
| CAD1-AT1G72680 | CCTGGGCATGAGATTGCT (SEQ ID NO: 39) | GCAGTACCTTTCATGAACAACAAT (SEQ ID NO: 69) | Real time |

Example 3

Affymetrix Microarray and RT-qPCR Studies

Total RNA was isolated from 35-d-old inflorescence stems of plants using an RNeasy Mini Kit (Qiagen, Valencia, Calif.), according to the manufacturer's instructions. RNA was quantified and evaluated for purity using a Nanodrop Spectrophotometer ND-100 (NanoDrop Technologies, Willington, Del.) and Bioanalyzer 2100 (Agilent, Santa Clara, Calif.).

For microarray analysis, three biological replicates were included for both the WT control and the fpgs1 mutant. For each array experiment, 500 ng of total RNA were used for labeling using the Affymetrix GeneChip® *Arabidopsis* ATH1 Genome Array (Affymetrix, Santa Clara, Calif.). Probe labeling, chip hybridization, and scanning were performed according to the manufacturer's instructions for the IVT Express Labeling Kit (Affymetrix). Data normalization between chips was conducted using RMA (Robust Multichip Average) (Irizarry et al., *Biostatistics*, 4, 249, 2003). Presence/absence calls for each probe set were obtained using dCHIP (Li et al., *Proc. Natl. Acad. Sci. U.S.A.* 98, 31, 2001). Gene selections for pairwise comparison were made based on Associative Analysis (Dozmorov et al., *Bioinformatics*, 19, 204-211, 2003) in Matlab (MathWorks, Natick, Mass.). In this method, the background noise presented between replicates and technical noise during microarray experiments was measured by the residual presented among a group of genes whose residuals are homoscedastic. Genes whose residuals between the compared sample pairs that are significantly higher than the measured background noise level were considered to be differentially expressed. A selection threshold of 2 for transcript ratios and a Bonferroni-corrected P value threshold of 2.19202E-06 were used. The Bonferroni-corrected P value threshold was derived from 0.05/N in these analyses, where N is the number of probe sets (22810) on the chip in order to correct the family wide false discovery rate.

For quantitative two-step RT-PCR, 1 µg of total RNA was reverse-transcribed to first-strand cDNA with the Qiagen cDNA synthesis kit (Qiagen, Hilden, Germany), and those cDNA were subsequently used as a template for qPCR with gene-specific primers. The plant-specific EF4A2 (At1g54270) gene served as a control for constitutive gene expression. Relative expression levels ($2^{-\Delta Ct}$) were calculated according to Ramakers et al. (*Neuroscience Letters*, 339, 62-66, 2003). In brief, expression levels of each gene were compared to the expression level of EF4A2, which was constant in all RNA samples and was set to 1. Values were the means of three biological and three technical replicates, and the oligonucleotides used in the study are presented in Table 1.

Example 4

Lignin Content and Composition Analysis

Figure 5:
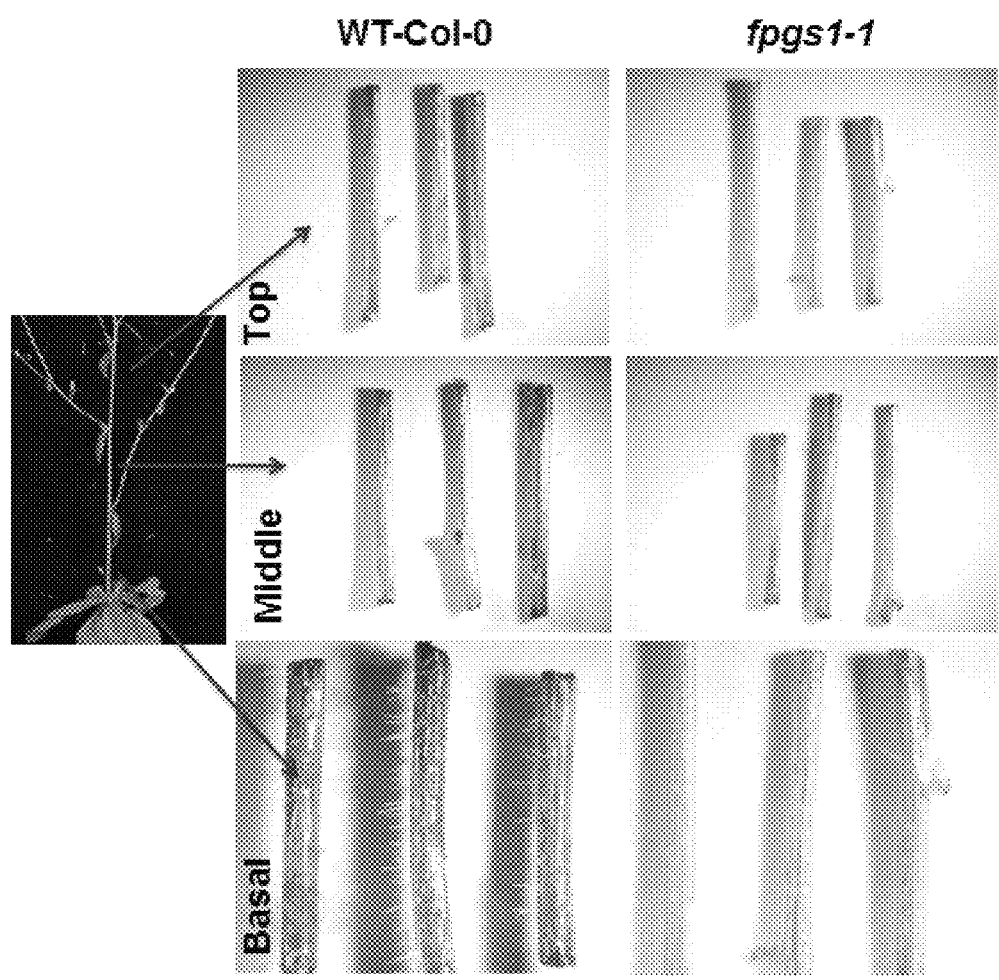
FIG. 5: Shows lignification in the inflorescence stems of wild-type and fpgs1-1 plants. (a) Basal stem portions were sectioned (50 μm), stained with phloroglucinol-HCl and imaged using Olympus-SZX 12 and Nikon Microphot-FX microscopes (UV filter). Less lignin staining was recorded in the fpgs1-1 plants. (b) Inflorescence stems were harvested from the top, middle and basal portion and were stained with phloroglucinol-HCl. All three sections showed less red coloration in fpgs1-1 mutants compared to wild-type plants.

Lignin content quantification was performed using inflorescence stems of 35-d-old plants. Basal parts (i.e., the region of the stem immediately adjacent to the rosette leaves) of the inflorescence stem were harvested into a fixation mixture of ethanol:acetic acid (3:1; v/v) and incubated at −20° C. for 24 hours. This was followed by a wash in 15% (w/v) sucrose and sectioning with a Cryostat Leica CM 1850. Sections (50 µM) were stained with phloroglucinol-HCl (0.5% [w/v] phloroglucinol in 6 N HCl) and color development was recorded using an Olympus SZX 12—Stereo Microscope and a Nikon DXM1200C Digital Camera, run by Nikon ACT-1C for DXM1200C software. In addition, a novel approach was used for robust and accurate staining of stem tissues for total lignin. Instead of tissue sections, whole intact stem segments were used for staining for more accurate visualization. Stem segments were harvested from three regions of the stem from top to bottom (FIG. 5b). Stem tissue in each segment was chopped into small pieces (5 mm) and incubated in chloroform:methanol (1:1; v/v) for 30 min. After two washings with chloroform:methanol, samples were incubated with 100% methanol for 30 min, followed by two final washings in $H_2O$. Samples were lyophilized for at least two days and later analyzed by phloroglucinol-HCl staining as described for tissue sections.

Lignin content and composition were measured in the post-flowering 35-d-old stem tissues by acetyl bromide (AcBr) (Hatfield et al., *J. Agri. Food Chem.*, 47, 628-632, 1999) and thioacidolysis methods (Lapierre et al., *Res. Chem. Intermed.*, 21, 397-412, 1995). Lignin-derived monomers (S, G, and H) were identified and quantified by GC/MS using a Hewlett-Packard 5890 series II gas chromatograph with a 5971 series mass selective detector (column: HP-1, 60 m×0.25 mm×0.25 µm film thickness). Mass spectra were recorded in electron impact mode (70 eV) with 60-650 m/z scanning range.

Example 5

Glycome Profiling and Immunofluorescence Labeling

Preparation of cell wall alcohol insoluble residue (AIR), cell wall fractionation and glycome profiling were carried out. Plant glycan-directed monoclonal antibodies (Pattathil et al., *Plant Physiol.* 153, 514-525, 2010) were obtained as hybridoma cell culture supernatants from laboratory stocks at the Complex Carbohydrate Research Center [CCRC, JIM and MAC series; available from CarboSource Services (www.carbosource.net)]. Thirty-five-day-old stems from both WT and fgps1-1 were fixed, sectioned, and immunolabeled.

Example 6

Determination of Saccharification Efficiency

Cell-wall residues (CWR) used in lignin analysis was also used for sugar analyses. Sugar release was analyzed spectrophotometrically using the phenol-sulfuric acid assay method (Dubois et al., *Analy. Chem.* 28, 350-356, 1956). Saccharification efficiency was determined as the ratio of sugars released by enzymatic hydrolysis to the amount of sugars present in the cell-wall material before enzymatic hydrolysis as described by Fu et al. (*BioEnergy Research*, 4, 153-164, 2011).

Example 7

High Throughput Pretreatment and Enzymatic Hydrolysis (HTPH)

The HTPH system at University of California, Riverside (Studer et al., *Biotechnol Bioeng.* 105, 231-238, 2010; DeMartini et al., *Bioresource Technology*, 102, 1352-1358, 2011) was employed to determine whether the mutants exhibited altered sugar release compared to the WT control during pretreatment and enzymatic hydrolysis. In light of this, glucose and xylose release from hydrothermal pretreatment and co-hydrolysis were measured. First, hydrothermal pretreatment was conducted at 180° C. for 11.1 minutes. Then, the pretreated slurry was allowed to proceed to a 72-hour co-hydrolysis step at 50° C. in 50 mM citrate buffer (pH 4.8). Accellerase® 1500 cellulase and Accellerase® XY xylanase from Genencor were used at a loading of 112.5+37.5 mg cellulase plus xylanase/g glucan+xylan in the raw biomass. In this method, sugar concentrations were quantified using Waters Alliance 2695 HPLC (Milford, Mass., USA) equipped with an Aminex HPX-87H column (BioRad, Hercules, Calif., USA) and a refractive index detector.

Example 8

Downscaled Compositional Analysis

Glucan and xylan were determined by performing a downscaled compositional analysis method (DeMartini et al., *Biotech. Bioengineer.* 108, 306-312, 2011), but using 100 times less biomass. The entire process was performed in 1.5-ml high recovery glass vials (Agilent, Santa Clara, Calif., USA) with 3 mg dry biomass, loaded into each vial by a Core Module Robotics Platform (Symyx Technologies, Sunnyvale, Calif.). A set of glucose and xylose sugar recovery standards (SRS) was also run in parallel for correction of sugar degradation. Sugars were analyzed by Waters Alliance 2695 HPLC (Milford, Mass., USA) equipped with an Aminex HPX-87H column (BioRad, Hercules, Calif., USA) and a refractive index detector.

Example 9

Microscope Image Acquisition

Confocal imaging was performed using a Leica TCS SP2 confocal microscope (Leica Microsystems) and the HCX PL APO 63x/1.2 W water-immersion objective. All images were analyzed using Leica Confocal Software. GFP channels were acquired by simultaneous scanning using 488-nm laser lines for excitation. The signals were detected between 500-530 nm for GFP. Microscopy of vascular-tissues was carried out after preparing 100 μM longitudinal sections of 35-d-old fresh stem tissues using a Vibratome 1000 plus. GUS staining was performed on 35-d-old stem tissues and 7-d-old whole seedlings using 3 mM potassium ferricyanide and ferrocyanide to limit diffusion of GUS reaction products.

Example 10

S-Adenosyl-Methionine (SAM) Analysis

Around 200 mg lyophilized grounded samples of wild-type and the mutant were taken into 10 ml ethanol:water (70:30 v/v) mix and samples were centrifuged at 14,000 rpm for 15 min at 4° C. Supernatant was collected and further processing and analysis of the sample was done as described by Castro et al. (*J. Pharmaceutical and Biomedical Analysis*, 29, 963-968, 2002). UPLC/FLR analysis of SAM derivatives was carried out using a Waters Acquity UPLC system (Waters) coupled to FLR detector (Waters). A Waters Acquity UPLC 2.1×150 mm, BEH C18 column was used for analysis at 20° C. The mobile phase consisted of 0.1 M sodium acetate in HPLC grade water, pH 4.5 (A) and HPLC grade acetonitrile (B). Using an injection volume of 2.0 μl, separation was achieved using the following gradient: isocratic at 95.8% A for 7.8 min; 95.8% A to 50% A in 6 min; isocratic at 50% A for 1 min; followed by re-equilibration at 95.8% A for 7 min at a flow rate of 0.280 ml/min. The fluorescent SAM derivatives were monitored at excitation of 270 nm and emission of 410 nm with a PMT Gain setting of 1.00 and data rate (5 pts/sec). Identification was based on retention time of authentic standards. Data was processed using Empower 2 Software (Waters).

Example 11

Figure 6:
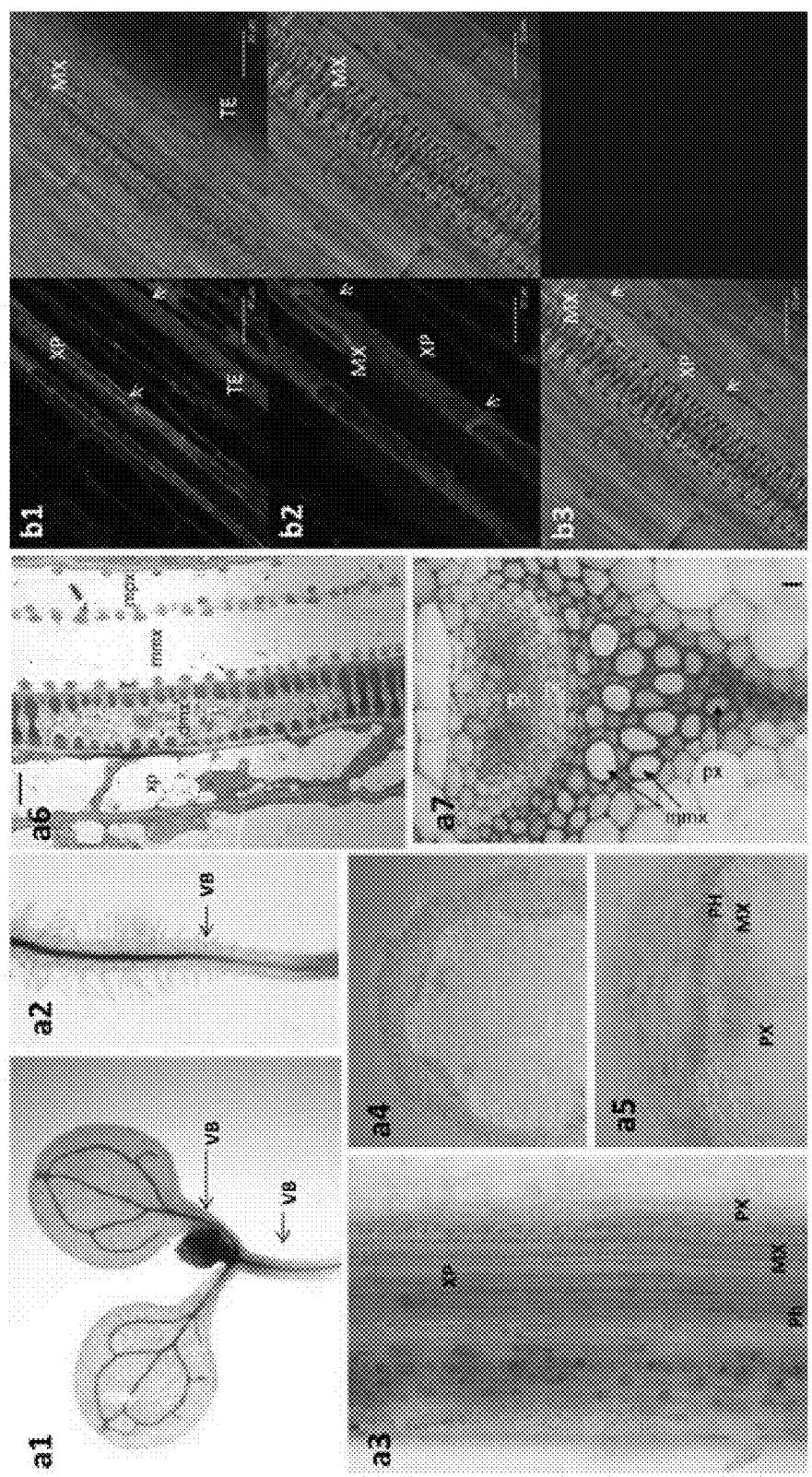
FIG. 6: Shows expression of AtFPGS1. (a) Plants transformed with pFPGS1-uidA constructs showing FPGS1 expression in the vascular bundles of the midrib in petioles (a1), root (a2) and stem (a3-5). Stem cross sections of the stained tissues show expression in the xylem parenchyma (XP), protoxylem region (PX), and procambium (PC) region. Structural detail of *Arabidopsis* stem cross sections (a6-a7) was acquired from Turner and Sieburth (2003) and this was compared to stem cross sections of pFPGS1-uidA and pFPGS1-FPGS1-GFP confirming expression in the vascular tissue region (a3-a5; b1-b3). (b) Localization of pFPGS1-FPGS1-GFP in the vascular-tissues. Longitudinal stem-sections (100 μm) of the plants expressing pFPGS1-FPGS1-GFP were examined for GFP fluorescence. Arrowheads in (b1-b3) indicate that pFPGS1-FPGS1-GFP fluorescence is specific to the xylem parenchyma (XP) cells and treachery elements (TE), phloem (Ph), procambium (PC), protoxylem (PX), mature metaxylem (MMX) and developing metaxylem (DMX). Scale bar 20 μm.
Figure 7:
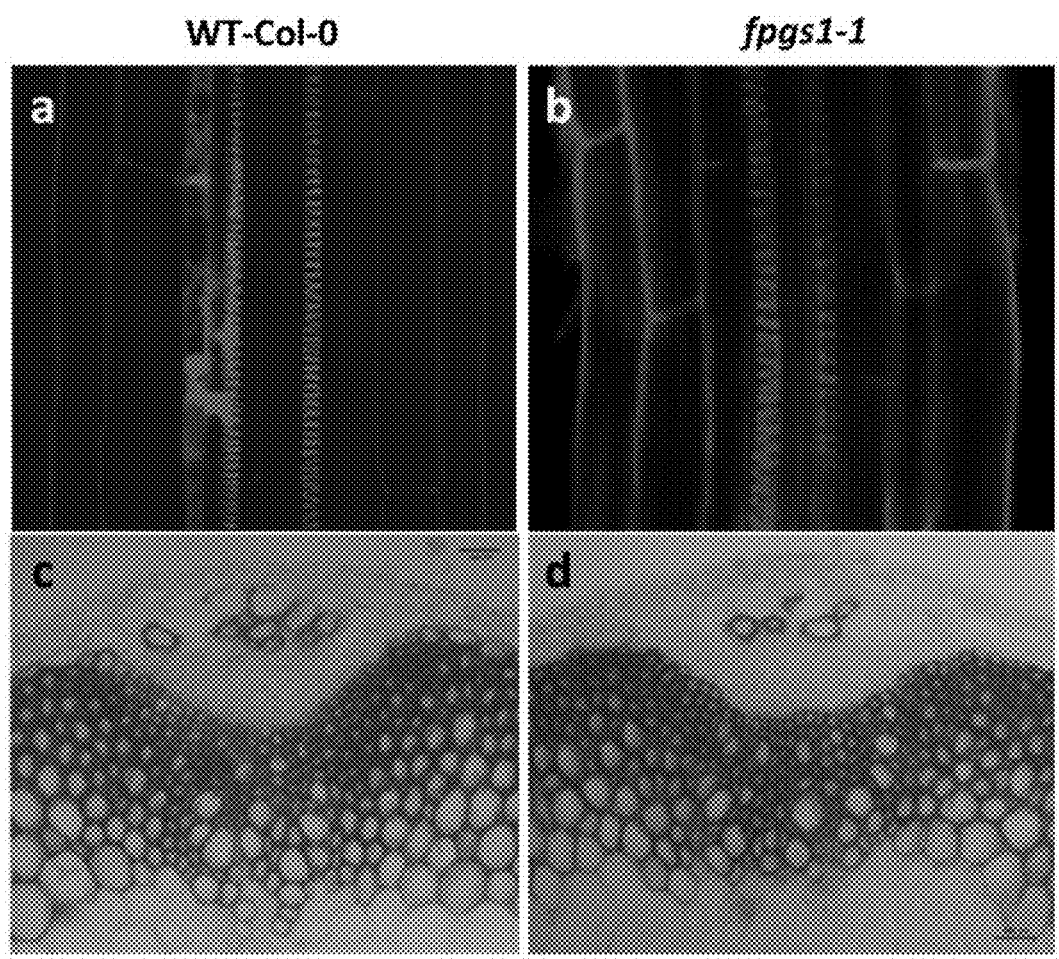
FIG. 7: Shows a lack of developmental defects in the vascular tissue of fpgs1-1. (a-b) Median confocal image of 7-day-old propidium iodide-stained wild-type and fpgs1-1 roots clearly showed no developmental defects in the vascular tissues. (c-d) Transverse section of 35-day-old stem of WT and fpgs1-1 stained with 0.01% safranine did not show any visual difference in the vascular tissue organization.
Figure 8:
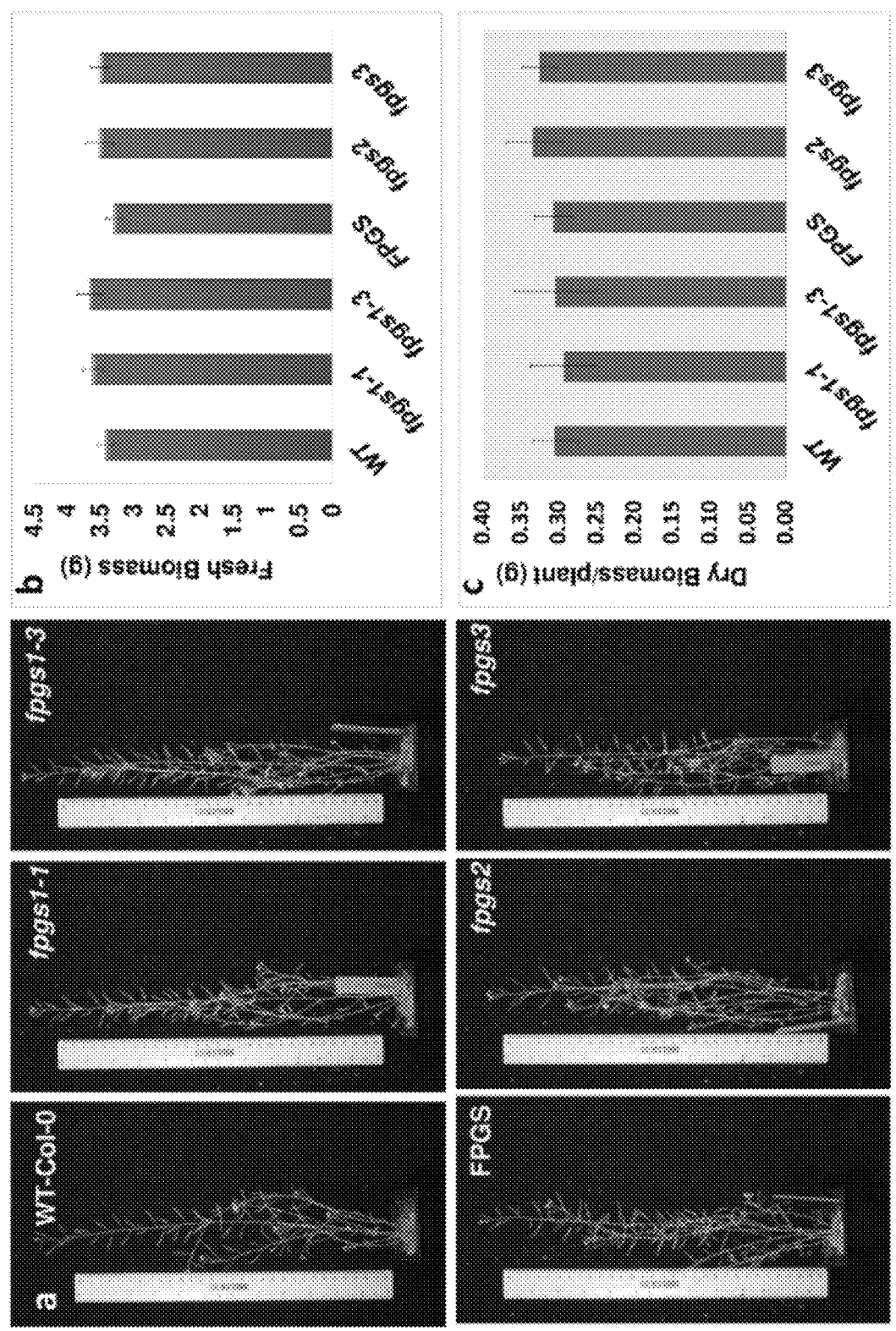
FIG. 8: Shows comparative aerial growth analysis of fpgs1 mutants. (a) 35-day-old wild-type plants were compared to two mutants of fpgs1 (fpgs1-1 and fpgs1-3), knockout mutants of two other isoforms of fpgs (fpgs2; mitochondrial and fpgs-3; cytoplasmic) and complemented transformed lines of fpgs1-1 [FPGS (pFPGS1-FPGS1-GFP:: fpgs1-1)] and collectively no visual differences were observed in the above-ground growth of these plants. Fresh (b) and dry (c) biomass of the plants were also not significantly different.

FPGS1 is Preferentially Expressed in Vascular Tissues, Consistent with its Role in Lignin Biosynthesis Lignification in plants occurs predominantly in the vascular tissues where secondary cell walls are being formed. The FPGS1 promoter was therefore fused to the β-glucuronidase (GUS) reporter gene and pFPGS1::GUS expression was analyzed in wild-type (Col-0) *Arabidopsis* plants. As expected, GUS expression was predominantly confined to the vascular tissues in cotyledons, hypocotyl, and roots of seedlings, and inflorescence stems of mature plants (FIG. 6a). The results with the GUS expression construct were consistent with the labeling patterns of plants expressing the entire regulatory sequence of FPGS1 consisting of the 7 kb genomic DNA fragment (2 kb upstream of the FPGS1 transcription start site, and 5 kb downstream from the FPGS1 start codon including all exon and intron regions) fused to green fluorescent protein (GFP) (FIG. 6b). Use of the GFP-based construct revealed that FPGS1 expression was most pronounced in xylem cells. Despite the elevated expression of FPGS1 in vascular tissues, no developmental defects in the vascular tissues of fpgs1-1 mutants were observed in primary roots and inflorescence stems (FIGS. 7 and 8).

Example 12

Lignin Composition is Altered in fpgs1 Mutants

Lignin deposition patterns in the wild-type and fpgs1-1 plants were compared. Microscopic observations of the vascular tissues of phloroglucinol-HCl-stained cross-sections of inflorescence stems showed less red coloration in fpgs1-1, indicative of reduced lignin levels (FIG. 5a); this reduction corresponded to reduced levels of lignin autofluorescence when stem sections were viewed under UV light (FIG. 5a).

Although phloroglucinol-HCl staining of stem cross-sections is a routine procedure to check for lignin deposition, consistently obtaining cross-sections from the same portion of the stem so as to ensure reliable comparison among genotypes is not always guaranteed. Therefore attempts were made to visualize lignin in intact inflorescence stems. Three separate portions of the inflorescence stem as depicted in FIG. 5b were harvested and divided into 5-mm segments. The stem pieces were fixed and incubated in phloroglucinol-HCl for 3 min. Comparative analysis of these stems under a light microscope clearly showed less lignin in the fpgs1 mutants as evident by the less intense red coloration.

Figure 9:
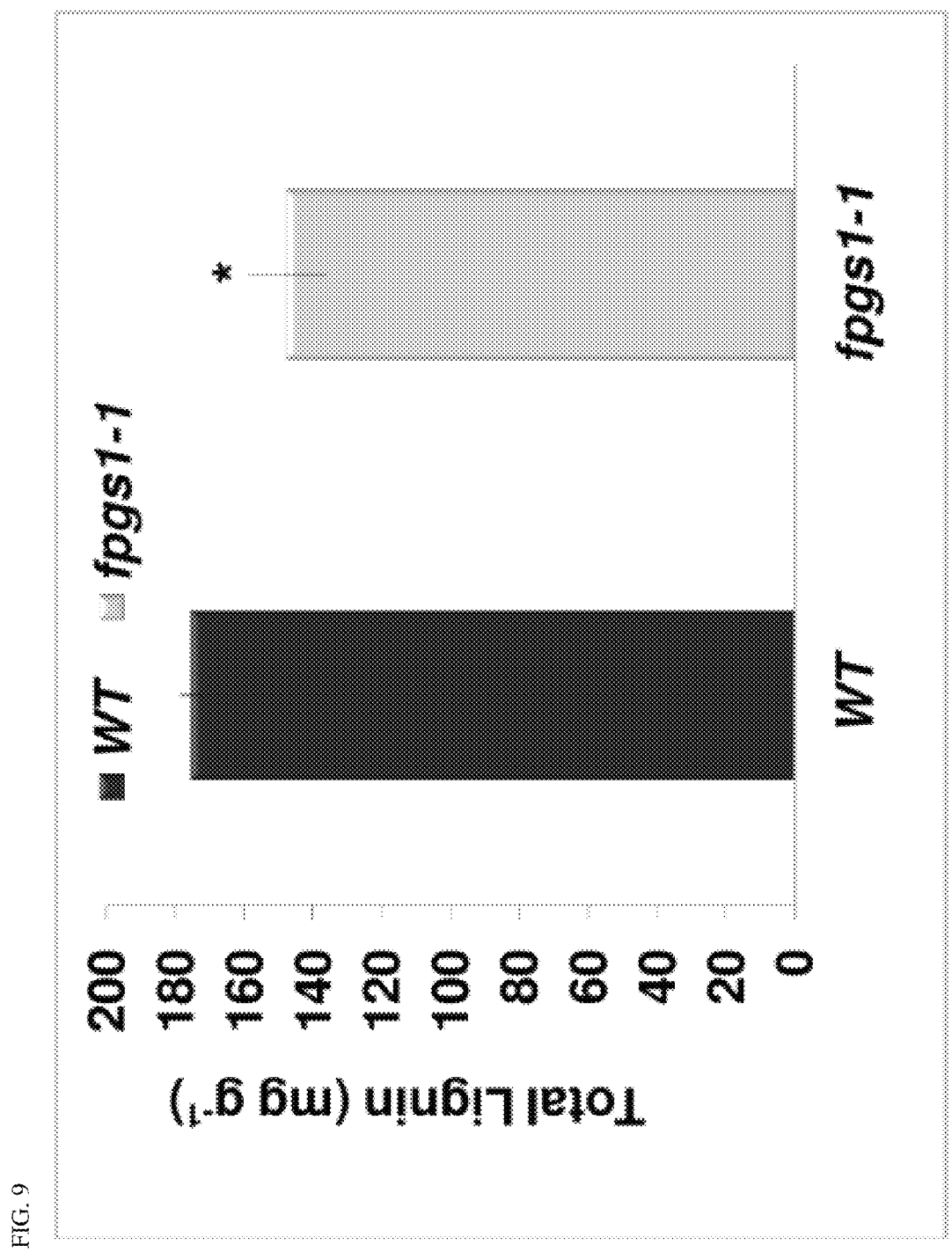
FIG. 9: Shows acetyl bromide (AcBr) lignin levels in wild-type and fpgs1-1 plants. Total lignin was significantly less in the fpgs1 mutants. Each biological replicate was visualized in a single column (average of n=5). Statistically significant difference t test (P<0.05).

Lignin levels were then quantified by the AcBr method, which revealed a 17% reduction in total lignin content in 35-d-old fpgs1-1 plants compared to controls (FIG. 9). Two other mutant alleles (fpgs1-2 and fpgs1-3; Srivastava et al., *Plant Physiol.* 155, 1237-1251, 2011) also exhibited significant reduction in total lignin, suggesting that the FPGS1 mutation was indeed the cause of the lower lignin phenotype (FIG. 10a). This was conclusively verified by introducing the pFPGS1::FPGS1-GFP construct into the fpgs1-1 background, which resulted in restoration of wild-type levels of lignin (FIG. 10b). Interestingly, the other two mutants of the three-member *Arabidopsis* FPGS family (fpgs2 and fpgs3), which correspond to the cytosolic and mitochondrial isoforms (Mershashi et al., 2010), did not show any major difference in total lignin compared to wild-type (FIG. 10b). The thioacidolysis method was then used to determine lignin composition in the fpgs1 mutant. A significant reduction in guaiacyl (G) lignin monomers, but not syringyl (S) or p-hydroxyphenyl (H) monomers, was observed in all fpgs1 mutant alleles compared to wild-type (FIGS. 11a-b). Similarly, total lignin levels were restored to wild-type levels in fpgs1-1 mutants complemented with pFPGS1::FPGS1-GFP (FIG. 10B).

Example 13

Transcript Profiling of fpgs1 Inflorescence Stems Reveals Down-Regulation of Genes in the Phenylpropanoid Pathway To gain insight into whether mutation of FPGS1 and the corresponding alterations in C1 intermediates resulting from this mutation lead to feedback regulation of genes directly involved in lignin biosynthesis, transcriptomic analysis was conducted of 35-d-old inflorescence stem tissues using six ATH1 Affymetrix chips. Transcriptome data revealed that about 400 genes were differentially expressed between the fpgs1-1 mutants and wild-type plants using a Bonferroni corrected P value of 2.19202E-06 and a ratio of 2 as cutoffs. Among the differentially expressed genes, 182 had higher expression in the fpgs1-1 mutant, while 227 had lower expression. Close examination of phenylpropanoid pathway-related genes showed that around 9 genes were significantly down-regulated in the mutant, including six O-methyltransferases, which also includes one CCoAOMT (At1g67980). Besides these, one peroxidase super family protein (At2g22420), cinnamoyl-CoA reductase (CCR-At5g14700) and a UDP-glucose:flavonol-3-O-glycoside-7-O-glucosyltransferase (UGT73C6-At2g36790) were also down regulated. The most up-regulated genes in the mutants were members of the R2R3 transcription factor gene family (At4g34990). Among the genes directly involved in the folate biosynthetic pathway, expression of homocysteine S-methyltransferase 3 (HMT3) that converts homocysteine to methionine was 6 times higher in the mutant. Microarray data further validated that the FPGS1 gene was down-regulated 5 times in the fpgs1 mutant, whereas genes encoding other FPSG2 and FPGS3 isoforms were not affected. It was also observed that genes involved in sulfate metabolism and in the glucosinolate biosynthesis pathway were differentially expressed in the mutant. Among 34 genes involved in sulfate metabolism detected by microarray analysis, 50% of them were significantly up-regulated in the fpgs1 mutant, and the majority of these up-regulated genes are involved in methionine-derived glucosinolate synthesis.

The microarray data were validated by quantitative real-time (qRT)-PCR experiments in 35-d-old stem tissues of fpgs1-1 and wild-type plants. Twenty two genes were tested, and transcript levels of CCoAOMT, COMT, SAM synthetases, SAM dependent methyltransferases and Laccase 4 were significantly repressed in the fpgs1-1 mutants, consistent with the microarray results (Table 2).

TABLE 2

Relative expression levels of some selected genes in the wild-type and fpgs1-1 plants estimated by real time qRT-PCR and microarray analysis.

| Gene ID | Gene Name | Relative to Internal Standard by RT-PCR | | Ratio (fpgs1/WT) | Ratio (fpgs1/WT) |
|---|---|---|---|---|---|
| | | fpgs1-1 | WT | qRT-PCR | Microarray |
| AT1G67980 | S-adenosyl-L-methionine: transcaffeoyl Coenzyme A 3-O-methyltransferase | 0.164 | 0.936 | 0.18* | 0.281** |
| AT1G21100 | Indole Glucosinolate O-Methyltransferase 1 | 0.665 | 2.411 | 0.28* | 0.193** |
| AT3G54150 | SAM-Dependent Methyltransferases Superfamily Protein | 0.184 | 0.634 | 0.29* | 0.270** |

TABLE 2-continued

Relative expression levels of some selected genes in the wild-type and fpgs1-1 plants estimated by real time qRT-PCR and microarray analysis.

| Gene ID | Gene Name | Relative to Internal Standard by RT-PCR | | Ratio (fpgs1/WT) | Ratio (fpgs1/WT) |
|---|---|---|---|---|---|
| | | fpgs1-1 | WT | qRT-PCR | Microarray |
| AT1G15125 | SAM-Dependent Methyltransferases Superfamily Protein | 2.591 | 8.325 | 0.31* | 0.380** |
| AT1G69526 | SAM-Dependent Methyltransferases Superfamily Protein | 0.02 | 0.048 | 0.41* | 0.500** |
| AT1G33030 | COMT-O-Methyltransferase Family Protein | 0.126 | 0.288 | 0.44* | 0.449** |
| AT4G22530 | SAM-Dependent Methyltransferases Superfamily Protein | 0.08 | 0.174 | 0.46* | 0.491** |
| AT2G38080 | Laccase 4 | 23.317 | 33.473 | 0.70* | 0.97 |
| AT1G02500 | S-Adenosylmethionine Synthetase 1 | 180.713 | 255.93 | 0.71* | 0.96 |
| AT1G66690 | SAM-Dependent Methyltransferases Superfamily Protein | 0.004 | 0.005 | 0.71* | 0.65** |
| AT4G01850 | S-Adenosylmethionine Synthetase 2 | 10.468 | 14.607 | 0.72* | 0.85** |
| AT1G15950 | Cinnamoyl CoA Reductase 1 | 23.261 | 31.304 | 0.74* | 1.12 |
| AT5G04230 | Phenyl Alanine Ammonia-Lyase 3 | 0.275 | 0.354 | 0.78* | 0.67** |
| AT1G72680 | Cinnamyl Alcohol Dehydrogenase 1 | 0.558 | 0.693 | 0.80* | 0.89 |
| AT2G36880 | Methionine Adenosyltransferase 3 | 9.275 | 6.237 | 1.49* | 1.35** |
| AT3G17390 | S-adenosylmethionine synthetase 3 | 10.637 | 6.958 | 1.53* | 1.32** |
| AT3G22740 | Homocysteine S-Methyltransferase 3 | 0.303 | 0.035 | 8.70* | 6.158** |

*student t-test p < 0.05;
**associative analysis P < 2.20E−06 (Bonferroni-corrected P value cutoff).

Example 14

Levels of the Methyl Group Donor S-adenosyl-L-methionine are Reduced in fpgs1

Figure 12:
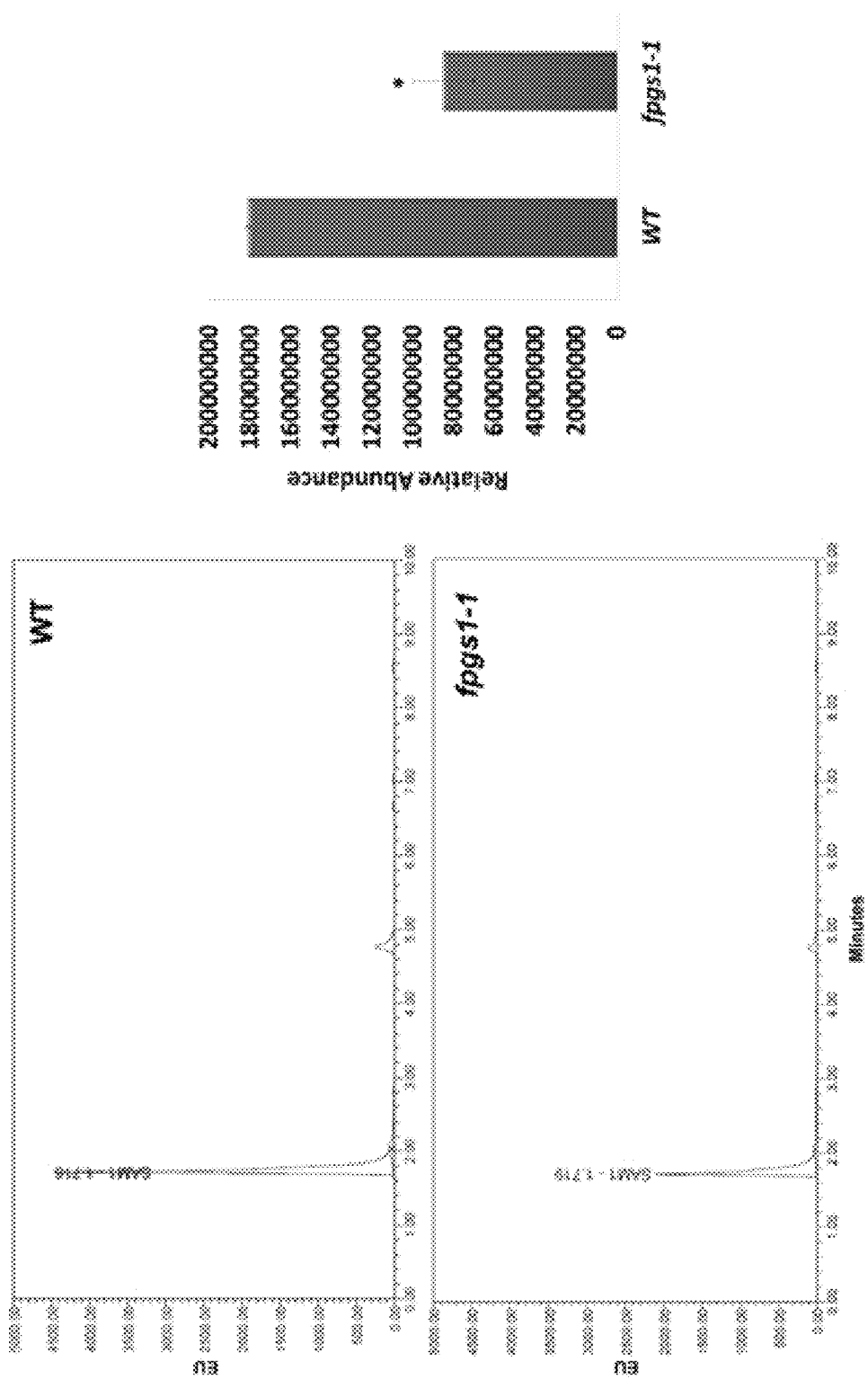
FIG. 12: Shows chromatographic profiles of wild-type and fpgs1 stem tissue samples analyzed for SAM content. Analysis was according to (Castro et al., 2002); two fold reductions in SAM were observed in the fpgs1-1 compared to wild-type plants.

To determine if altered levels of S-adenosyl-L-methionine (SAM) contributed to the lignin phenotypes observed in fpgs1, SAM was quantified by HPLC based on the method described by Castro et al. (*J. Pharmaceutical and Biomedical Analysis*, 29, 963-968, 2002). Extracts from fpgs1-1 mutant stems had about 50% less SAM content than extracts from wild-type stem (FIG. 12).

Example 15

Figure 13:
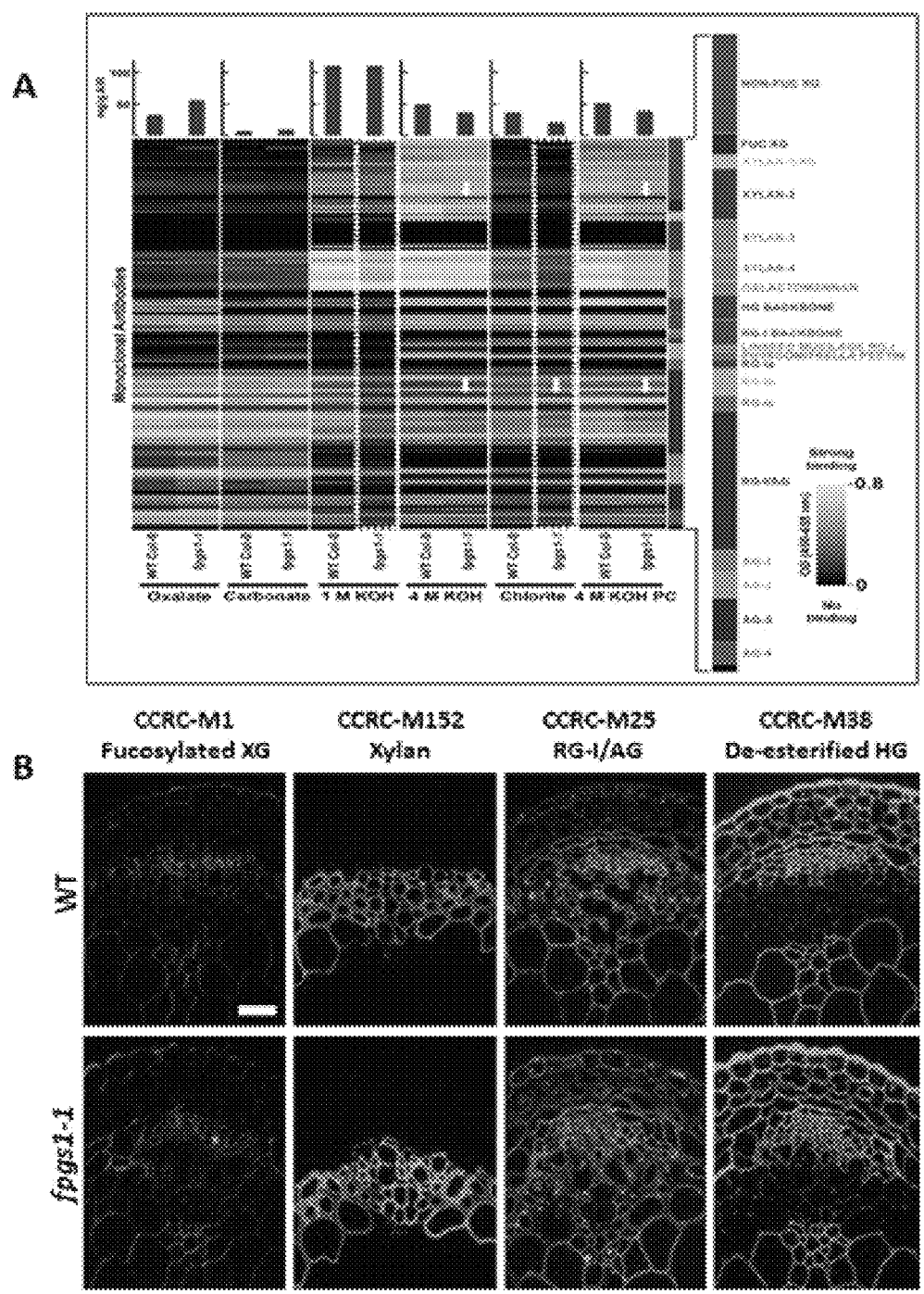
FIG. 13: Shows immunological analyses of stems harvested from wild-type and fgps1-1 plants. A. Glycome profiling of sequential extracts prepared from the cell walls isolated from 35-d-old stems of fpgs1-1 and wild-type plants. The data are the average of three independent biological replicates. Various extraction reagents used are indicated at the bottom of the figure. The panel on right depicts the clades of monoclonal antibodies that recognize most major classes of plant cell wall glycans. The dotted boxes and arrows highlight the differences in the glycome profiles between fpgs1-1 and wild-type plants. The yellow-black scale indicates the strength of the ELISA signal: bright yellow color depicts strongest binding and black color indicates no binding. B. Immunofluorescence labeling with four selected antibodies representing different clades of antibodies. Tissue was harvested from 35-day old plants and fixed and sectioned as described in Methods. (Scale bar=25 µM and is applicable to all images).

Glycome Profiling Reveals Subtle Alterations in the Cell Wall of fpgs1 Inflorescence Stems Glycome profiling was conducted (Pattathil et al., Immunological approaches to plant cell wall and biomass characterization: glycome profiling. In *Methods in Molecular Biology, Biomass Conversion: Methods and Protocols*, Vol 908 (M. Himmel, ed), New York, N.Y.: Springer Science Business Media, pp. 61-72, 2012; Zhu et al., *Mol. Plant*, 3, 818-833, 2010) of the cell wall material [alcohol insoluble residues (AIR)] isolated from 35-d-old inflorescence stems of wild-type and fpgs1-1 mutants to determine any alterations in the overall extractability of non-cellulosic glycan epitopes (FIG. 13A). The glycome profiles of the fpgs1-1 mutants were mostly similar to those of wild-type lines. However, a subtle reduction in the overall abundance of xyloglucan (non-fucosylated and fucosylated) and xylan epitopes were observed in the 1 M KOH and chlorite extracts of fpgs1-1 mutant walls (see white dotted blocks). Similar subtle reductions in the abundance of epitopes recognized by the pectic backbone (HG-backbone and RG-I backbone), RG-Ia through c, RG-I/AG, and AG1-4 groups of monoclonal antibodies (mAbs) were also evident in the 1 M KOH and chlorite extracts (see white dotted blocks).

Overall, when the total amounts of carbohydrate released during the various extractions were quantitated, it was noted that mild extractions released higher amounts of carbohydrate from cell walls of fpgs1 inflorescence stems (significantly higher in oxalate and marginally higher in carbonate extracts), indicating that the extractability of cell walls from fpgs1-1 was slightly higher than from wild-type (FIG. 13A). Differences between fpgs1 and wild-type wall extracts were also noted with respect to the binding of single antibodies (see white arrows), but these need further investigation to fully validate. The differences include the absence of binding of CCRC-M90, a non-fucosylated xyloglucan-directed mAb, to 4 M KOH and 4MKOH PC extracts from fpgs1-1 lines (upper row of white arrows) and the absence of binding of CCRC-M24, an RG-I/AG-directed mAb, to 4 M KOH, chlorite and 4 M KOH PC extracts from fpgs1-1 lines (lower row of white arrows).

To determine if the subtle differences in glycome profiling between wild-type and fpgs1-1 is reflected in situ, immunolabeling was performed on cross-sections of 40-d-old inflorescence stems using monoclonal antibodies directed against a fucosylated xyloglucan epitope (CCRC-M1), a xylan epitope (CCRC-M152), an arabinogalactan side chain epitope of RG-I (RG-I/AG), and a non-methylesterified homogalacturonan epitope (CCRC-M38). All of these mAbs labeled wild-type and fpgs1-1 mutant stems in a similar fashion; however, labeling intensity differed slightly among some of the mAbs (FIG. 13B).

Example 16

Saccharification Efficiency is Enhanced in fpgs1 Mutants

Figure 14:
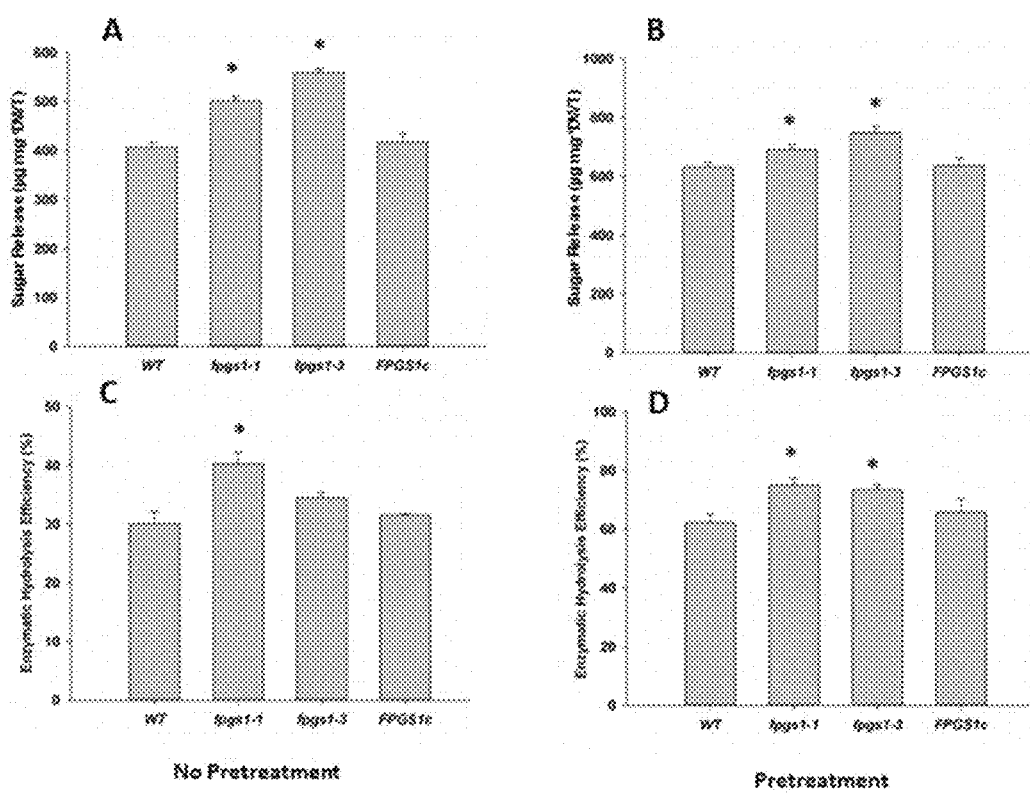
FIG. 14: Shows glucose release and saccharification efficiency of fpgs1 and wild-type plants. Total sugar release (A, B) and saccharification efficiency (C, D) of fpgs1-1, fpgs1-3, wild-type, and complemented FPGS1c plants with or without acid pretreatment, respectively. Mature inflorescence stems of 20 individual plants were pooled and assayed for saccharification efficiency. * indicates samples that are statistically significant over wild-type (Tukey's test, P<0.05).
Figure 15:
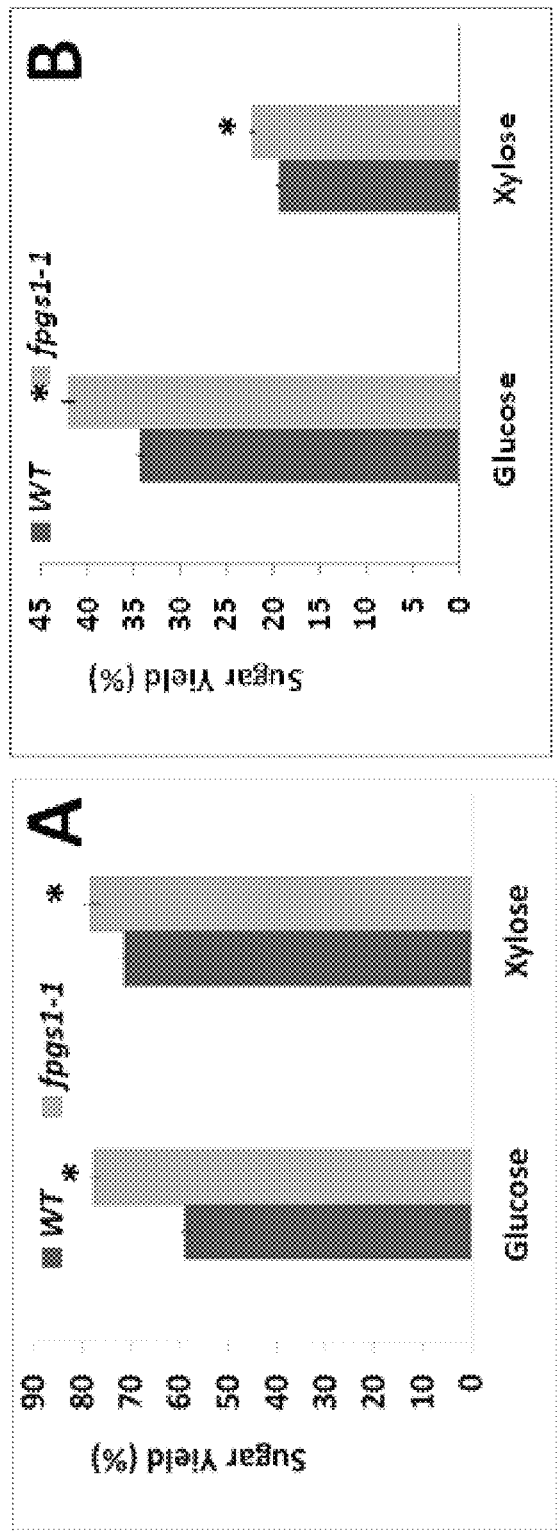
FIG. 15: Shows sugar analysis in cell wall residues of atfpgs1-1 and wild-type stems. Glucose and xylose release after hydrothermal pretreatment and enzymatic-hydrolysis (A) and no pretreatment (B) of atfpgs1-1 and wild type stem samples. Mature inflorescence stems of 20 individual plants were analyzed for compositional analysis and sugar release assay. Data are the means±se from five separate experiments. *Statistically significant different; t-test (P<0.05).

Mature whole plants (stem and leaves) (i.e. when green pods started turning gold) were analyzed for sugar release. Enzymatic hydrolysis of the cell wall residues (CWR) with acid treatment prior to enzymatic hydrolysis showed 29% and 37% higher sugar release in the fpgs1-1 and fpgs1-3 mutants, respectively, compared to wild-type plants (FIG. 14A). Sugar release from CWR without acid pretreatment released 23% and 15% sugar in the fpgs1-1 and fpgs1-3 plants, respectively, when compared to wild-type plants (FIG. 14B). Accordingly, the saccharification efficiency of the mutant increased 18-34% with acid pre-treatment and around 14-20% without acid pre-treatment (FIGS. 14C-D). To verify these results, an independent test for sugar release was performed on CWRs from wild-type and fpgs1 using hydrothermal pretreatment (hydrated CWRs were kept at 180° C. for 11.1 minutes; DeMartini et al., *Biotech. Bioengineer.* 108, 306-312, 2011) and enzymatic hydrolysis. Glucose and xylose release from these treatments were measured, and a 32% and 9% higher release of glucose and xylose, respectively, were observed in the fpgs1 CWRs when samples were pretreated, and 32% and 15.7% higher release of glucose and xylose, respectively, when CWRs were not pretreated (FIG. 15).

Example 17

Sugar Release in Transgenic Switchgrass and *Populus* Compared to Control

Figure 17:
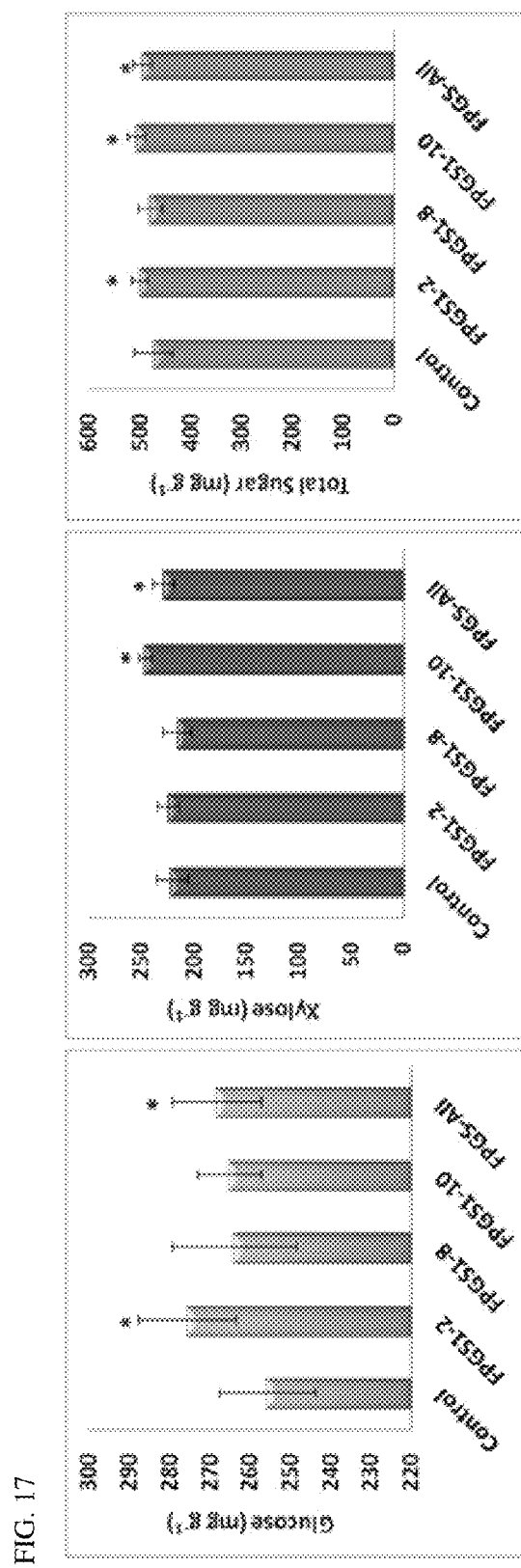
FIG. 17: Shows glucose, xylose, and glucose+xylose released from stem tissues of PvFPGS1-RNAi lines and vector control plants at the R1 stage.

Three RNAi lines of PvFPGS1 based on their transcript level reduction were selected for compositional analysis at the National Renewable Energy Laboratory (NREL). The region selected for RNAi is shown in FIG. 16. Plants were sampled at the R1 stage and whole stem tissues were used. A significant increase in glucose was recorded in PvFPGS1-RNAi line 2, and PvFPGS1-RNAi line 10 had significant increases in xylose and total sugar (FIG. 17). Consequently, RNAi lines 2 and 10 of PvFPGS1 showed 6% and 7% increase in total sugar (glucose and xylose), respectively, compared to vector control plants (FIG. 17).

Figure 18:
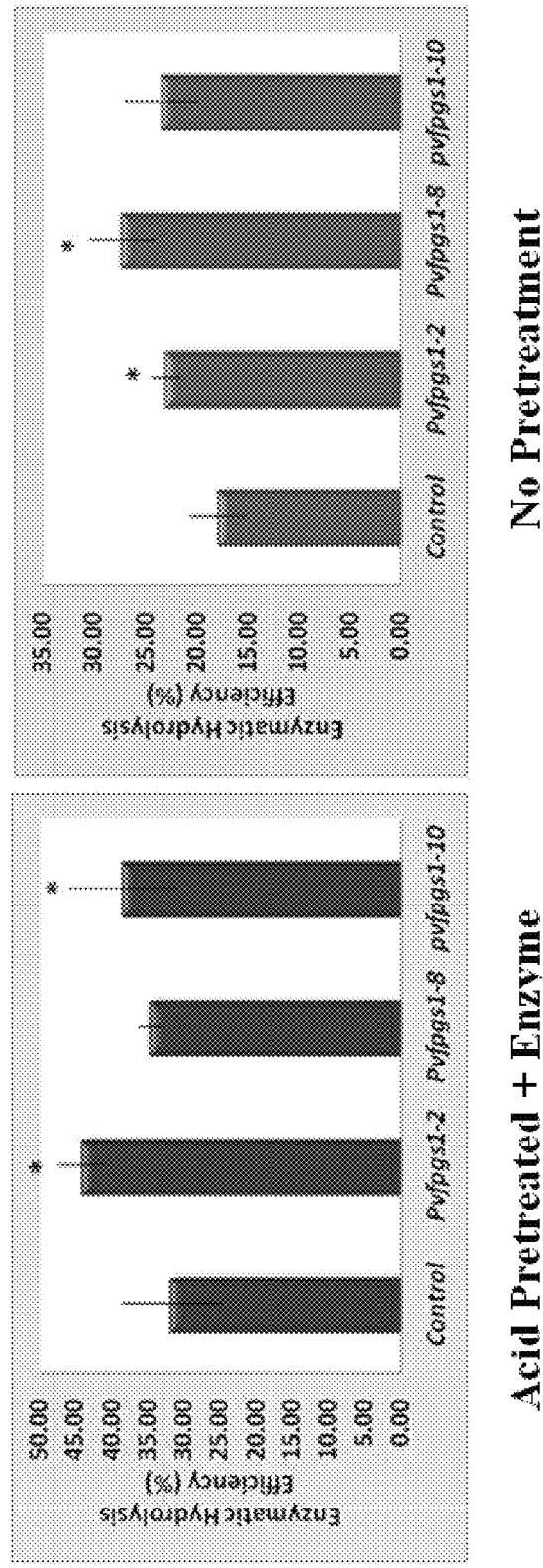
FIG. 18: Shows saccharification efficiency in acid pretreated samples and no acid treated samples of Pvfpgs1-RNAi lines and vector control plants at the R1 stage. The asterisk indicates a statistically significant difference according to Student's t test (P<0.05).

To gather additional data on these RNAi lines, the same three RNAi lines (Pvfpgs1-RNAi lines 2, 8, and 10) and vector controls plants were used for biochemical assays. Stem materials were harvested at R1 stage and saccharification assay (sugar release per unit of biomass) was performed. Compared to control plants, RNAi lines 2, and 10 showed significant increases in saccharification efficiency (Total sugar/acid treated+Enzyme released sugar) when they were exposed to mild acid and a cocktail of various cell wall degradable enzymes, but RNAi line 8 did not show any major difference in saccharification efficiency (FIG. 18). Similarly, saccharification efficiency (Total sugar/enzyme released sugar) of all three PvFPGS1-RNAi lines was also higher when they were treated with only enzymes and not pretreated with acids. This increase in saccharification efficiency in RNAi lines 2 and 8 was statistically significant (FIG. 18).

Example 18

Other Phenotypes of Transgenic Switchgrass or *Populus*

Figure 19:
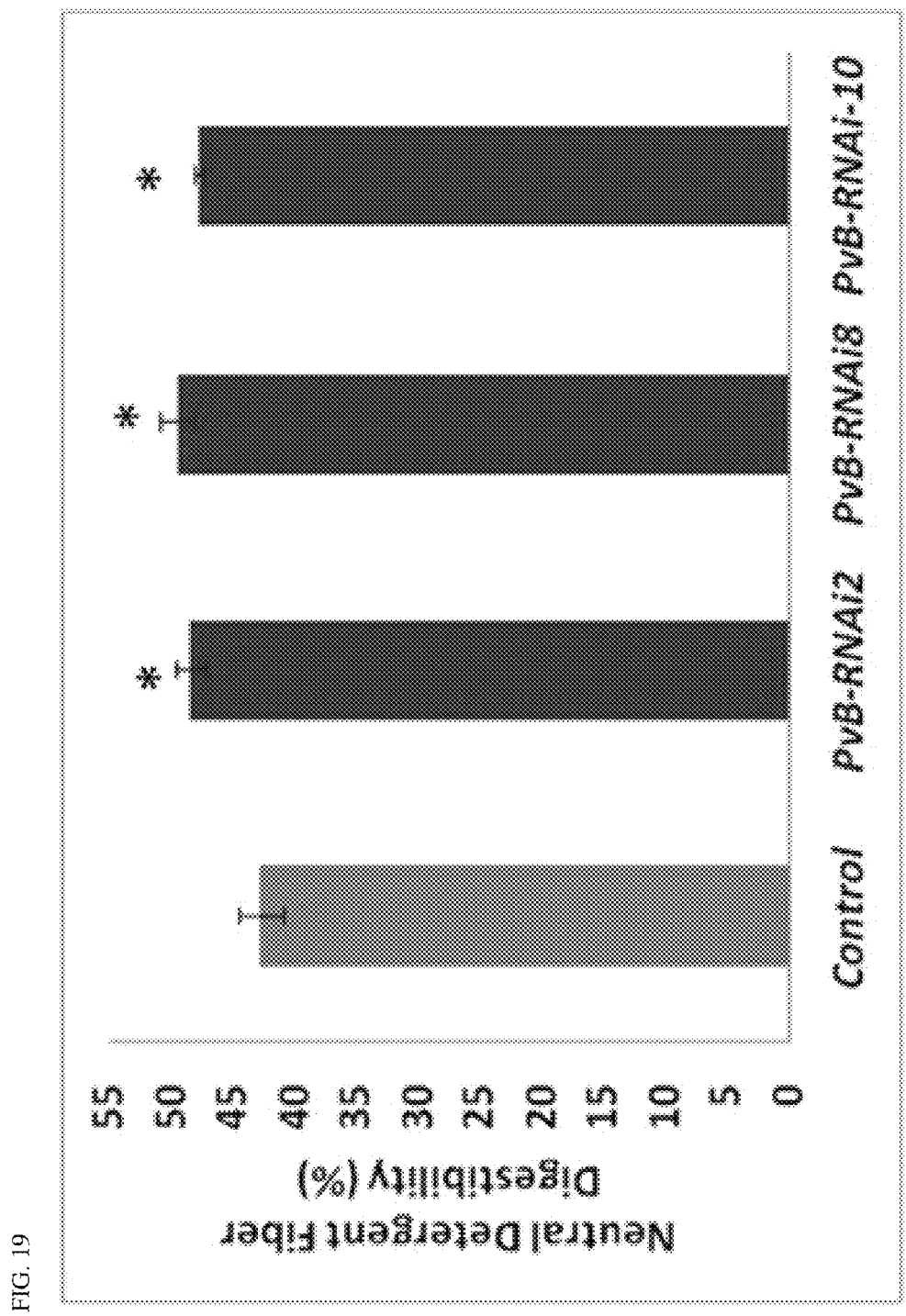
FIG. 19: Shows neutral detergent fiber digestibility (NDFD) of PvFPGS1-RNAi lines and control plants at the R1 stage. Pvfpgs1-RNAi lines had higher fiber digestibility, with significant 11.7%, 13.6%, and 10.5% increases in NDFD in Pvfpgs1-RNAi lines 2, 8, and 10, respectively.

NIRS (Near Infra-Red Spectroscopy) analysis was performed on Pvfpgs1-RNAi lines 2, 8, and 10. This analysis is a reflection of in vitro true dry matter digestibility (IVT-DMD) and neutral detergent fiber digestibility (NDFD), which measures the amount of forage material that can be digested by the rumen of animals. Hence it is an important indicator of fiber quality and lignin content. The NDFD of the Pvfpgs1-RNAi lines was analyzed and showed that all selected lines had higher fiber digestibility (FIG. 19), with significant 11.7%, 13.6%, and 10.5% increases in NDFD in Pvfpgs1-RNAi lines 2, 8, and 10, respectively.

The basis for NIRS experiment was the mathematic relationship of the wet chemistry and the NIR absorption/reflectance by the organic bonds of known samples. These samples were used to predict unknown sample through these correlations. An equation derived from analysis of known samples was used to calculate all unknown samples.

Figure 20:
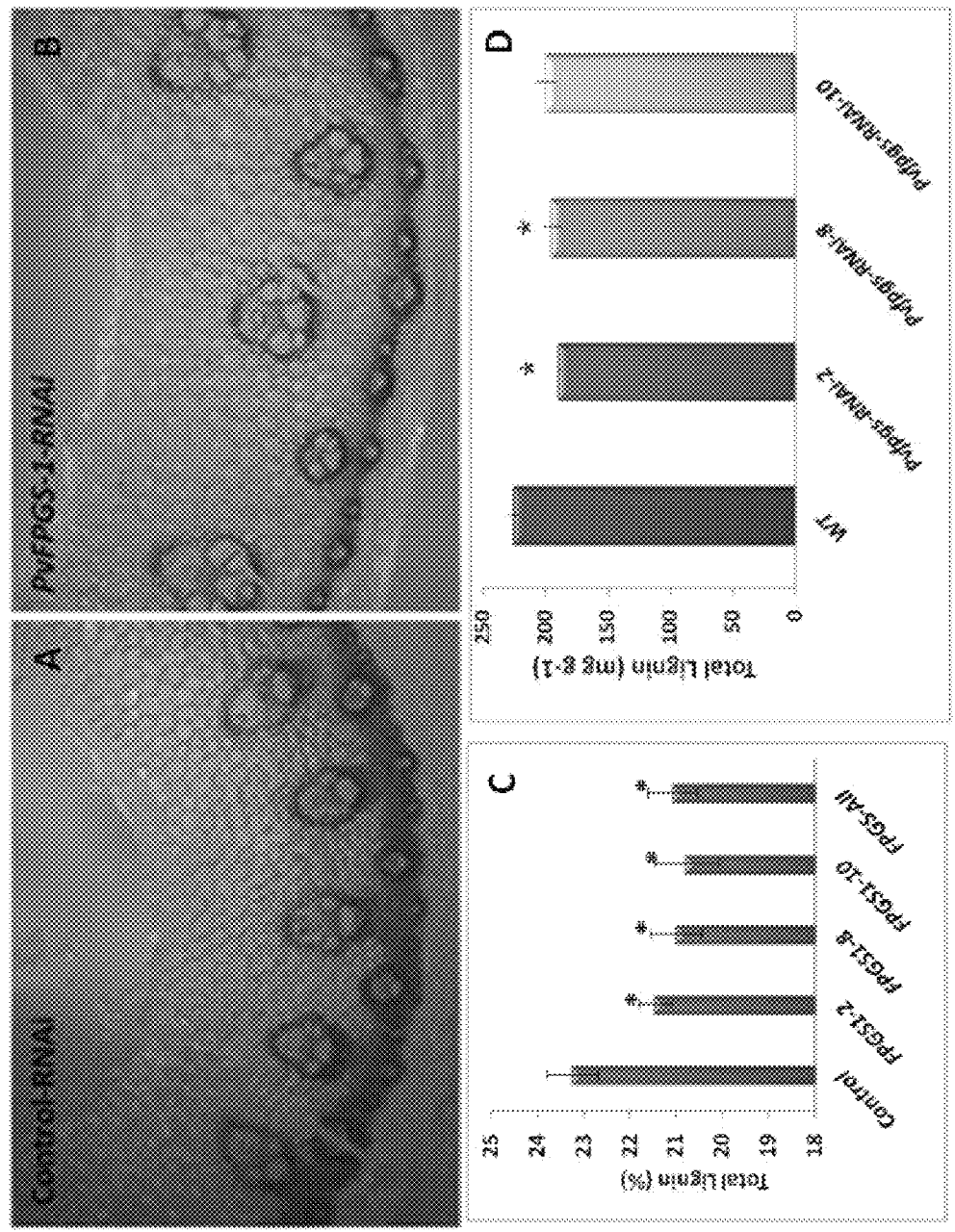
FIG. 20: (A-B) Phloroglucinol stained switchgrass RNAi stems of PvFPGS-1 showing reduced lignin in selected RNAi lines. (C) Total lignin analysis (NREL) in PvFPGS1-RNAi lines and in control plants. (D) AcBr lignin analysis in PvFPGS1-RNAi lines and in vector control plants.

The PvFPGS1-RNAi lines were further tested for lignin deposition in the inflorescence stems. Intense lignin staining was seen in the control plants, whereas less lignin staining was detected in the PvFPGS1-RNAi sections, indicating less lignin deposition in the xylem cells and fibers (FIG. 20A-B). To confirm these histochemical results, total lignin content was analyzed by the acetyl bromide (AcBr) method. Significant reductions in total lignin were recorded in PvFPGS1-RNAi lines (FIG. 20D). More in-depth quantitative lignin analysis on all selected PvFPGS1-RNAi lines were done through NREL characterization pipeline, and the total lignin was significantly reduced in all three RNAi lines, with an average of 10% reduction in selected RNAi lines (FIG. 20C). All of these results were in agreement with previous observations for *Arabidopsis* (atfpgs-1) mutants, in which defects in the plastidial isoform of folylpolyglutamate synthetase (FPGS) were found to affect lignin biosynthesis.

Example 19

Figure 21:
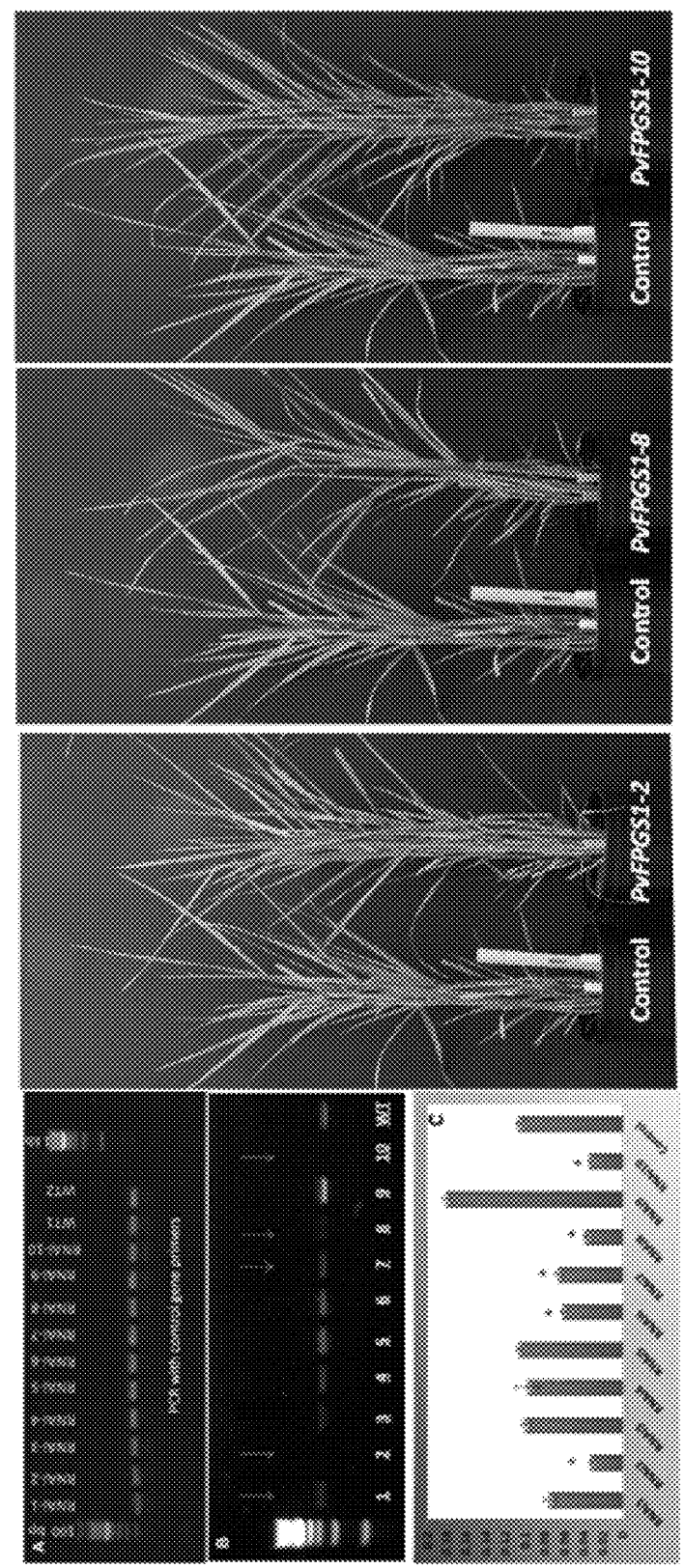
FIG. 21: Shows semi-quantitative PCR results for PvFPGS1 by control primers (A) and gene specific primers (B); RT-qPCR of PvFPGS1-RNAi lines (C); Phenotypes of switchgrass PvFPGS1-RNAi selected lines. RNAi lines 2, 8, and 10 have lowest transcripts, but repression of PvFPGS1 has no impact on their aerial phenotype.

Switchgrass or *Populus* Phenotypes are Correlated with Transcript Expression Levels Twenty-nine RNAi lines were acquired for PvFPGS-1. Confirmatory tests were performed on 10 hygromycin-resistant transgenic lines using GUS linker and gene specific primers, and it was found that all 10 lines were positive transgenic lines. To analyze the PvFPGS1 expression in these lines, a gene-specific forward primer (PvDFB-RNAi-F, AAGCAGGGGCATAAGGACA, SEQ ID NO:5) was used that was designed for outside the targeted region, and the reverse primer (PvDFB-RNAi-R, ATCGATTTGTTCA-GGCTCAGC, SEQ ID NO:6) was within the target region. Total RNA was extracted from the second internodes of approximately two-month-old transgenic plants, and these were reverse-transcribed to check expression levels of PvFPGS1 by semi-quantitative RT-PCR. Using 22 PCR cycles, plant numbers 2, 8, and 10 had very low or no detectable transcript levels compared to the wild-type plants (FIG. 21A, B). Similar conclusions were drawn by RT-qPCR results (FIG. 21C) prompting the selection of these plants for further analysis. The selected lines were transferred into 2-gallon pots, and each selected line was replicated three times for subsequent physiological and biochemical characterization. All plants, along with 3 vector control lines, were grown until the R1 stage and harvested for analysis. As shown in FIG. 21D, PvFPGS1-RNAi lines have no dramatic differences when compared to control plants.

Example 20

Growth and Other Phenotypes in Species Other than Switchgrass or *Populus*

Above-ground biomass of plants with defects in AtFPGS1 was not affected (FIG. 8*a*) and no significant difference was found in the fresh biomass (FIG. 8*b*), or dry biomass (FIG. 8*c*) of the atfpgs1-1 mutant when compared to same physiological age wild-type plants.

Figure 10:
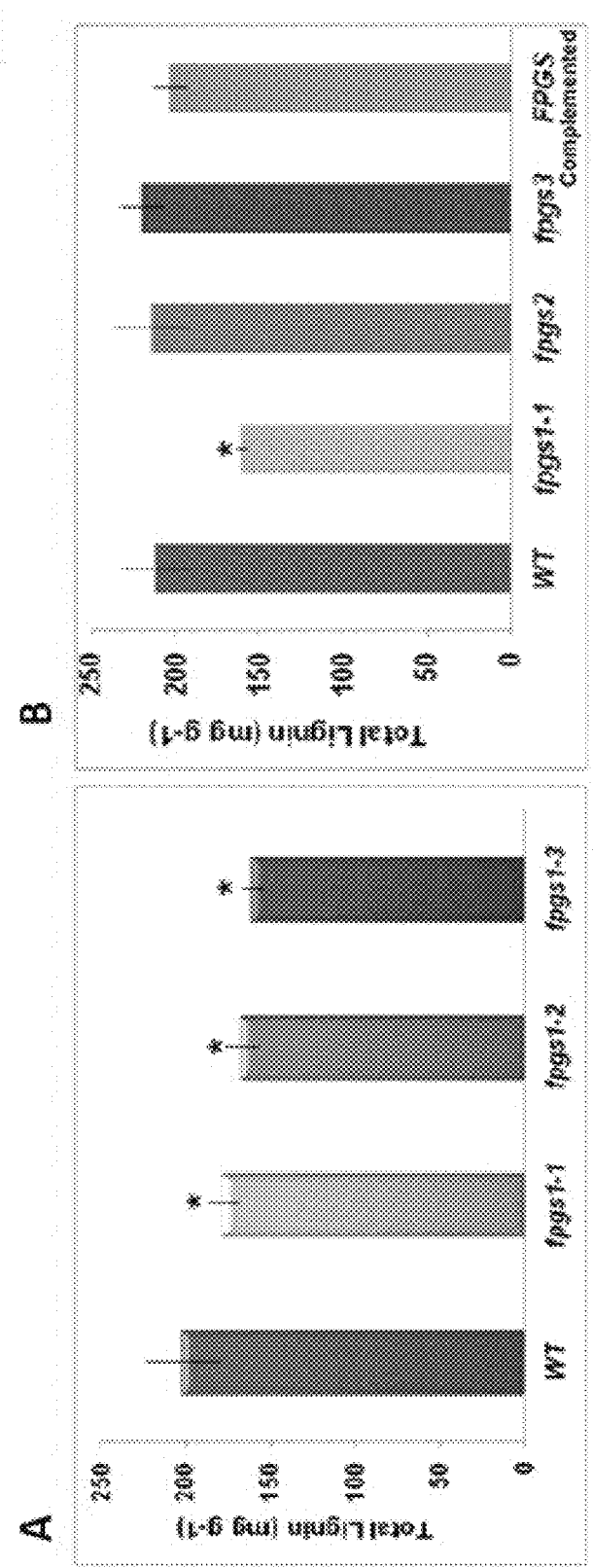
FIG. 10: Shows AcBr lignin levels in wild-type and fpgs1-1. Alterations in total AcBr lignin of all three independent mutant alleles of fpgs1 (fpgs1-1, fpgs1-2, fpgs1-3) (a) and knockout mutants of the other two isoforms of fpgs (fpgs2 and fpgs3) along with complemented fpgs1-1 (b) showed that total lignin was significantly less in the fpgs1 mutants only. Each data point was collected from five biological replicates and is visualized in a single column (average of n=5). Means with different letters are statistically significant (Tukey's test, P<0.05).
Figure 22:
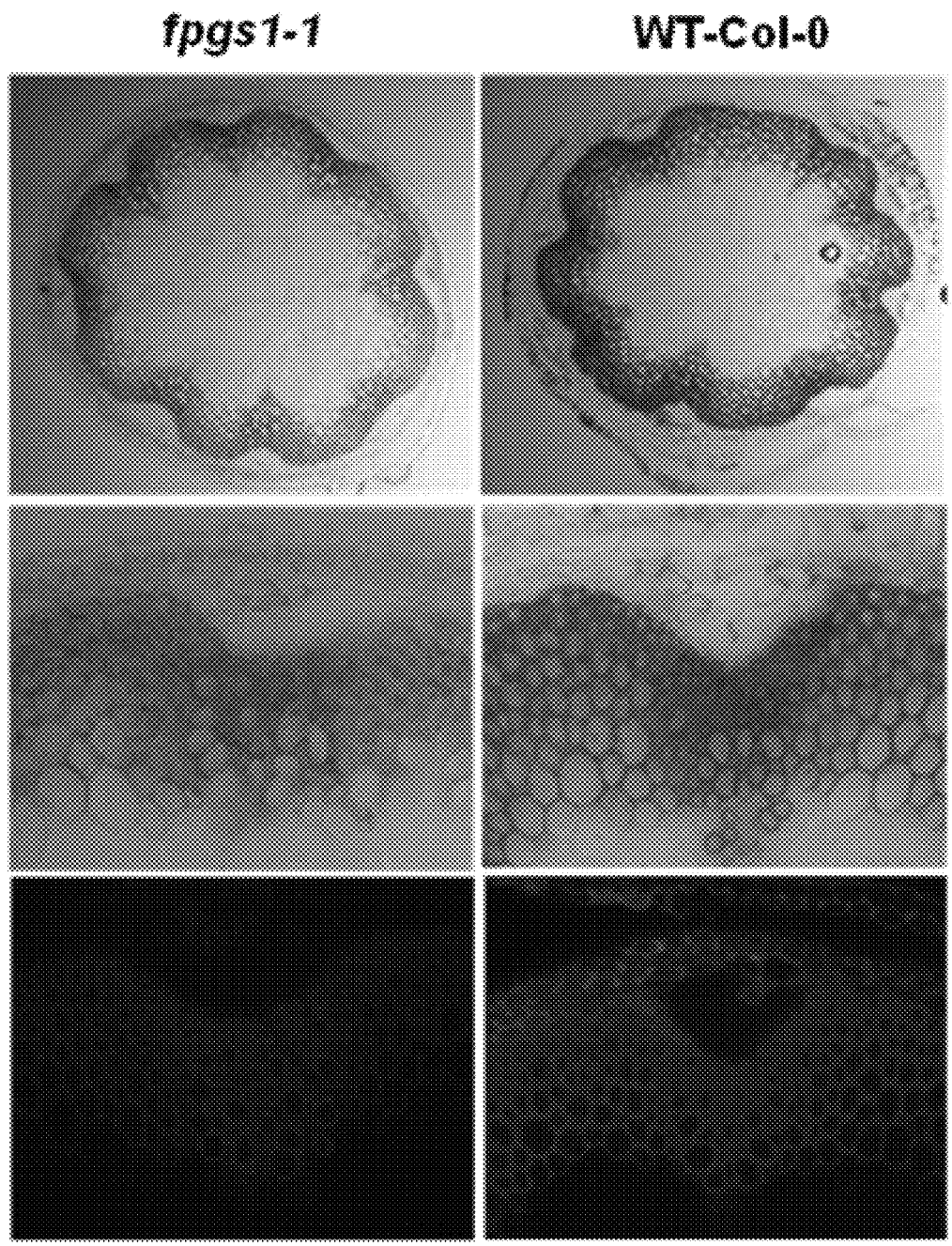
FIG. 22: Shows lignification in the inflorescence stems of wild-type and fpgs1-1 plants. (A) Basal stem portions were sectioned (50 µm), stained with phloroglucinol-HCl showing less lignin in the atfpgs1-1 plants.

Microscopic observations of phloroglucinol-HCl stained cross-sections of inflorescence stems showed less red coloration in the atfpgs1-1, which is indicative of reduced lignin (FIG. 22). Phloroglucinol-HCl staining was verified by examining inflorescence stem cross sections for lignin autofluorescence. It was found that fpgs1-1 cross sections were less fluorescent compared to wild-type cross sections (FIG. 22). Histological evaluation of lignin was followed by more sensitive biochemical tests, such as the acetyl bromide (AcBr) method. Using this method, it was found that 35-d-old fpgs1-1 plants had 17% reduction in the total lignin content (FIG. 10). Two other mutant alleles (fpgs1-2 and fpgs1-3) also exhibited significant reduction in total lignin indicating that the FPGS1 mutation was the cause of the lower lignin phenotype (FIG. 10A). Furthermore, restoration of wild-type levels of lignin was accomplished by introducing the pFPGS1::FPGS1-GFP construct (FIG. 10), but the other two isoforms of FPGS (fpgs2 and fpgs3 mutants), which correspond to the cytosolic and mitochondrial isoforms, did not show any major difference in total lignin compared to wild-type (FIG. 10B).

Example 21

Silencing of FPGS1 in Switchgrass

Figure 24:
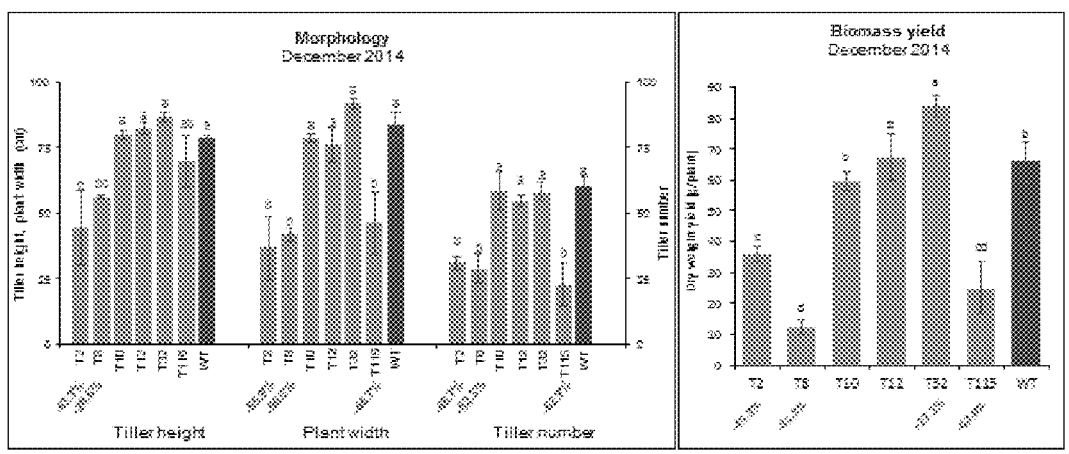
FIG. 24: Shows field growth data for FPGS RNAi Lines. Six independent RNAi lines with a range of fpgs down regulation were selected for field study. RNAi lines 2, 8, and 10 were selected for analysis in the greenhouse growth study.
Figure 25:
FIG. 25: Shows a field study of switchgrass FPGS RNAi lines: (A) FPGS field two months after transplanting, showing green plants; and (B) senesced field pictures taken 3 months later.

Transgenic switchgrass lines showing silencing of FPGS1 were selected for evaluation in field and greenhouse trials and showed promise in maintaining biomass production. Six independent RNAi lines with a range of fpgs down regulation were selected for field study (FIGS. 23-24). Green switchgrass FPGS RNAi lines in the field study two months after transplanting are shown in FIG. 25A, and plants exhibiting senescence 3 months later are shown in FIG. 25B.

Following the field studies, RNAi lines T2, T8, and T10 were selected for analysis in a greenhouse growth study. RNAi lines T2, T8, and T10 exhibiting significant reduction in fpgs1 gene expression were evaluated and measurements were collected at week 12 (FIG. 26). The biomass of the RNAi lines was similar or superior to WT. Line T10 had growth traits in greenhouse and field studies similar to the parent (WT) plant. One RNAi line was found to maintain biomass in both greenhouse and field trials, while other lines showed better growth in one or the other of the environments.

Example 22

Mutation in FPGS Genes Resulted in Reduced Lignin in Maize

Mutations in the brown midrib4 (bm4) gene affect the accumulation and composition of lignin in maize. Fine-mapping analysis of bm4 narrowed the candidate region to an approximately 105-kb interval on chromosome 9 containing six genes. Only one of these six genes, GRMZM2G393334, showed decreased expression in mutant plants. At least four of 10 Mu-induced bm4 mutant alleles contain a Mu insertion in the GRMZM2G393334 gene. Based on these results, it was concluded that GRMZM2G393334 is the bm4 gene. GRMZM2G393334 encodes a putative FPGS, which functions in one-carbon (C1) metabolism to polyglutamylate substrates of folate-dependent enzymes. Yeast complementation experiments demonstrated that expression of the maize bm4 gene in FPGS-deficient met7 yeast is able to rescue the yeast mutant phenotype, thus demonstrating that bm4 encodes a functional FPGS. Consistent with earlier studies, bm4 mutants exhibit a modest decrease in lignin concentration and an overall increase in the S:G lignin ratio relative to wild-type. Orthologs of bm4 include at least one paralogous gene in maize and various homologs in other grasses and dicots. Discovery of the gene underlying the bm4 maize phenotype illustrates a role for FPGS in lignin biosynthesis.

What is claimed is:

1. A plant exhibiting artificially down-regulated FPGS1 gene expression, wherein the plant comprises an RNAi construct directed against the FPGS1 gene and exhibits reduced lignin content.

2. The plant of claim 1, wherein the RNAi construct comprises all or a portion of SEQ ID NO:3 or a complement thereof.

3. The plant of claim 1, wherein the plant is a forage plant, a biofuel crop, a cereal crop, or an industrial plant.

4. The plant of claim 1, wherein the plant is a switchgrass (*Panicum virgatum*) or poplar plant.

5. A plant part of the plant of claim 1 comprising the RNAi construct.

6. The plant part of claim 5, wherein the plant part is a protoplast, cell, meristem, root, pistil, anther, flower, seed, embryo, stalk or petiole.

7. A method of reducing lignin content in a plant comprising down-regulating expression of the FPGS1 gene in the plant using an RNAi construct directed against the FPGS1 gene, wherein the lignin content of the plant is reduced when compared to a plant exhibiting normal FPGS1 expression.

8. The method of claim 7, wherein the plant is a monocotyledonous plant.

9. The method of claim 7, wherein the plant is a dicotyledonous plant.

10. The method of claim 7, wherein the reduced lignin content further comprises reduced G lignin content.

11. A plant produced by the method of claim 7, or plant part or seed thereof, wherein the plant comprises the RNAi construct and exhibits reduced lignin content.

12. The plant part of claim 11, further defined as a protoplast, cell, meristem, root, leaf, node, pistil, anther, flower, seed, embryo, stalk or petiole.

13. A method of improving a forage crop or biofuel crop comprising down-regulating expression of the FPGS1 gene in a plant using an RNAi construct directed against the FPGS1 gene, wherein the plant comprises reduced lignin content and further comprises a beneficial trait when compared to a plant that lacks the reduced expression.

14. The method of claim 13, wherein said beneficial trait is selected from the group consisting of increased sugar release, increased forage digestibility, and increased saccharification efficiency.

15. The method of claim 13, wherein the plant is a monocotyledonous plant.

16. The method of claim 13, wherein the plant is a dicotyledonous plant.

17. The method of claim 13, wherein the reduced lignin content further comprises reduced G lignin content.

18. A plant produced by the method of claim 13, or plant part or seed thereof, wherein said plant comprises the RNAi construct and exhibits reduced lignin content.

19. The plant part of claim 18, further defined as a protoplast, cell, meristem, root, leaf, node, pistil, anther, flower, seed, embryo, stalk or petiole.

20. A method of producing plant biomass, the method comprising:
   (a) obtaining a plant of claim 1 exhibiting reduced expression of the FPGS1 gene;
   (b) growing said plant under plant growth conditions to produce plant tissue from the plant; and
   (c) preparing biomass from said plant tissue.

21. The method of claim 20, wherein said preparing biomass comprises harvesting said plant tissue.

22. The method of claim 20, further comprising using the biomass for biofuel.

23. A method of making a commodity product comprising:
   (a) obtaining a plant of claim 1 exhibiting reduced expression of the FPGS1 gene, wherein the lignin content of the plant is decreased when compared to a plant that lacks the reduced expression;
   (b) growing the plant under plant growth conditions to produce plant tissue from the plant; and
   (c) preparing a commodity product from the plant tissue.

24. The method of claim 23, wherein preparing the commodity product comprises harvesting the plant tissue.

25. The method of claim 23, wherein the commodity product is selected from the group consisting of paper, paper pulp, ethanol, butanol, biodiesel, biogas, silage, carbon fiber, animal feed, and fermentable biofuel feedstock.

26. The method of claim 13, wherein improving said forage crop or biofuel crop comprises increasing the digestibility of said crop, increasing sugar release of said crop, or increasing the saccharification efficiency of said crop.

27. A plant produced by the method of claim 26, wherein said plant is selected from the group consisting of Pvfpgs1-RNAi lines 2, 8, and 10.

\* \* \* \* \*

SEQUENCE LISTING

```
<160> NUMBER OF SEQ ID NOS: 69

<210> SEQ ID NO 1
<211> LENGTH: 1716
<212> TYPE: DNA
<213> ORGANISM: Arabidopsis thaliana

<400> SEQUENCE: 1
atgtttgcag tttcgatagt acctcgaacc acatcgtgcc gtttgagctc tgcctttctc      60
tgtcaactct cgattcctct cactcttcgg ctccaccatc actaccaaca ccaccagcct     120
cacctaccat ctcctctctc ttttcagatt cattcgttaa gaaagcagat cgacatggca     180
gctcaaggag gtgattcata tgaggaagcg ttggctgctt tgtcgtcttt gatcacgaaa     240
cgaagtcgtg ctgataagag caataaaggg gatcgctttg agttagtctt tgattatctc     300
aagctacttg acctggaaga agacatttta aagatgaatg ttattcatgt cgctggtacc     360
aaaggcaagg gatccacatg tacctttaca gagtctatta ttcgaaacta tggctttcga     420
actggactct tcacttcacc tcacctcatt gatgtccggg aaagatttcg tttggatggt     480
gtggacataa gtgaagagaa atttttggga tatttctggt ggtgctataa caggctcaag     540
gagagaacta acgaggagat accaatgcct acatatttcc gcttccttgc attgctagct     600
tttaaaatat ttgctgcaga agaggtagat gctgctatat tggaggttgg attaggtgga     660
```

```
aagtttgatg ccaccaatgc ggttcagaaa cctgtggtat gtggtatttc ttcactcgga    720
tatgaccaca tggaaattct aggtgataca cttggaaaaa ttgctggtga aaggctgga     780 attttcaagc ttggagttcc agctttcaca gtgccccaac ctgatgaagc catgcgtgtc    840
cttgaagaga aagcttccga acagaagtg aatctcgaag tggtgcagcc actaaccgca     900
aggctgttaa gtggtcagaa acttgggctt gatggggaac accaatatgt caatgctggt    960
ctagcagttt cgcttgcctc tatctggctt cagcaaattg gtaaactaga agttccgagt   1020
cggactcaga tgagtattct gcctgagaaa ttcatcaaag ggttagctac agcgagtttg   1080
caaggacgag cacaggtcgt ccctgatcaa tatactgaat ctcggacttc aggagatcta   1140 gtatttatc tggatggagc tcacagtcca gaaagcatgg aagcatgcgc caaatggttt    1200
tcggttgcgg ttaagggaga caaccagtca gggagttcag acatttggt taatggctct    1260 gcaggatcct ctcatgataa atggtcaaat gaaacctgtg aacagatatt gttgttcaat   1320
tgtatgtcag ttcgggaccc aaatctactg cttccacatc taagaatat gtgcgcaaaa    1380 tacggtgtca atttcaagaa ggcattgttt gtaccaaaca tgtcggtgta tcataaggtt   1440
ggtacagcag ctgatttgcc agagaatgat ccacaggttg acttgtcatg gcagttcaca   1500
cttcagaaag tgtgggaaag ccttgtgcag agtgaaagag atggagaaaa agatggtgaa   1560
agtgatggaa acagtgaggt gtttacttca ctacccatgg caataaaaatg tctaagggac   1620 actgtacatg agagtagctc agccacacgt ttccaggtcc ttgtaactgg ttcgttacat   1680
cttgtgggcg atgtactgag attaatcaga aaatga                              1716

<210> SEQ ID NO 2
<211> LENGTH: 571
<212> TYPE: PRT
<213> ORGANISM: Arabidopsis thaliana

<400> SEQUENCE: 2

Met Phe Ala Val Ser Ile Val Pro Arg Thr Thr Ser Cys Arg Leu Ser
1               5                   10                  15

Ser Ala Phe Leu Cys Gln Leu Ser Ile Pro Leu Thr Leu Arg Leu His
            20                  25                  30

His His Tyr Gln His His Gln Pro His Leu Pro Ser Pro Leu Ser Phe
        35                  40                  45

Gln Ile His Ser Leu Arg Lys Gln Ile Asp Met Ala Ala Gln Gly Gly
    50                  55                  60

Asp Ser Tyr Glu Glu Ala Leu Ala Ala Leu Ser Ser Leu Ile Thr Lys
65                  70                  75                  80

Arg Ser Arg Ala Asp Lys Ser Asn Lys Gly Asp Arg Phe Glu Leu Val
                85                  90                  95

Phe Asp Tyr Leu Lys Leu Leu Asp Leu Glu Glu Asp Ile Leu Lys Met
            100                 105                 110

Asn Val Ile His Val Ala Gly Thr Lys Gly Lys Gly Ser Thr Cys Thr
        115                 120                 125

Phe Thr Glu Ser Ile Ile Arg Asn Tyr Gly Phe Arg Thr Gly Leu Phe
    130                 135                 140

Thr Ser Pro His Leu Ile Asp Val Arg Glu Arg Phe Arg Leu Asp Gly
145                 150                 155                 160

Val Asp Ile Ser Glu Glu Lys Phe Leu Gly Tyr Phe Trp Trp Cys Tyr
                165                 170                 175

Asn Arg Leu Lys Glu Arg Thr Asn Glu Glu Ile Pro Met Pro Thr Tyr
            180                 185                 190
```

```
Phe Arg Phe Leu Ala Leu Leu Ala Phe Lys Ile Phe Ala Ala Glu Glu
        195                 200                 205

Val Asp Ala Ala Ile Leu Glu Val Gly Leu Gly Gly Lys Phe Asp Ala
        210                 215                 220

Thr Asn Ala Val Gln Lys Pro Val Val Cys Gly Ile Ser Ser Leu Gly
225                 230                 235                 240

Tyr Asp His Met Glu Ile Leu Gly Asp Thr Leu Gly Lys Ile Ala Gly
                245                 250                 255

Glu Lys Ala Gly Ile Phe Lys Leu Gly Val Pro Ala Phe Thr Val Pro
                260                 265                 270

Gln Pro Asp Glu Ala Met Arg Val Leu Glu Glu Lys Ala Ser Glu Thr
            275                 280                 285

Glu Val Asn Leu Glu Val Val Gln Pro Leu Thr Ala Arg Leu Leu Ser
        290                 295                 300

Gly Gln Lys Leu Gly Leu Asp Gly Glu His Gln Tyr Val Asn Ala Gly
305                 310                 315                 320

Leu Ala Val Ser Leu Ala Ser Ile Trp Leu Gln Gln Ile Gly Lys Leu
                325                 330                 335

Glu Val Pro Ser Arg Thr Gln Met Ser Ile Leu Pro Glu Lys Phe Ile
            340                 345                 350

Lys Gly Leu Ala Thr Ala Ser Leu Gln Gly Arg Ala Gln Val Val Pro
        355                 360                 365

Asp Gln Tyr Thr Glu Ser Arg Thr Ser Gly Asp Leu Val Phe Tyr Leu
    370                 375                 380

Asp Gly Ala His Ser Pro Glu Ser Met Glu Ala Cys Ala Lys Trp Phe
385                 390                 395                 400

Ser Val Ala Val Lys Gly Asp Asn Gln Ser Gly Ser Ser Gly His Leu
                405                 410                 415

Val Asn Gly Ser Ala Gly Ser Ser His Asp Lys Trp Ser Asn Glu Thr
            420                 425                 430

Cys Glu Gln Ile Leu Leu Phe Asn Cys Met Ser Val Arg Asp Pro Asn
        435                 440                 445

Leu Leu Leu Pro His Leu Lys Asn Met Cys Ala Lys Tyr Gly Val Asn
    450                 455                 460

Phe Lys Lys Ala Leu Phe Val Pro Asn Met Ser Val Tyr His Lys Val
465                 470                 475                 480

Gly Thr Ala Ala Asp Leu Pro Glu Asn Asp Pro Gln Val Asp Leu Ser
                485                 490                 495

Trp Gln Phe Thr Leu Gln Lys Val Trp Glu Ser Leu Val Gln Ser Glu
            500                 505                 510

Arg Asp Gly Glu Lys Asp Gly Glu Ser Asp Gly Asn Ser Glu Val Phe
        515                 520                 525

Thr Ser Leu Pro Met Ala Ile Lys Cys Leu Arg Asp Thr Val His Glu
    530                 535                 540

Ser Ser Ser Ala Thr Arg Phe Gln Val Leu Val Thr Gly Ser Leu His
545                 550                 555                 560

Leu Val Gly Asp Val Leu Arg Leu Ile Arg Lys
                565                 570

<210> SEQ ID NO 3
<211> LENGTH: 1623
<212> TYPE: DNA
<213> ORGANISM: Panicum virgatum
```

<400> SEQUENCE: 3

```
atgcgctcgc atccccctct cgccgcccac ctccgccgcc tcctcctcct ctcgccctcc     60
acccaactaa cccatcgcgc cgccatggcc tccaccgccg ccgtcgctcg ggcaggtgct    120
gtggcgccgg cggagtacga ggaggtgctg gggcggctct cctcgctcat cacgcagaag    180
gtgcgcgcgc acagcggcaa ccgaggcaac cagtgggacc tcatggcaca ctacgtcaag    240
attctggagc tggaggagcc catcgcgcgg atgaaggtca tccacgtcgc agggaccaag    300
ggcaagggtt cgacatgcac gttcaccgag tcaatcctgc gatcgtgtgg cttccacact    360
gggctgttca cctcaccaca tttgatggat gtcagggagc gattccggct agatggagtt    420
gatatttctg aagagaaatt tttgaagtac ttttggtggt gctggaataa gttgaaggag    480
aagactgatg atgatattcc catgccagcc tatttcaggt tcctggcgtt gctcgcattc    540
aagatatttt ctgctgagca ggtagatgtt gctgttctcg aggttggcct tggagggaag    600
tttgatgcaa ctaatgtggt tgaagcacct gtagtttgtg ggtatcttc gcttggatat    660
gatcatatgg aaattcttgg gaatacgctt ggagaaatcg ctggggagaa ggctgggatt    720
ttcaagaaag gagttccagc ctatactgct ccacaacaag aagaggcaat ggttgctctc    780
aaacaaagag cttcggagtt gggtatacct ctccaagttg ctgatcctct ggtgccgtat    840
cacttaaaag gtcaacttct tggactgaat ggtgaacacc aatacataaa tgctggcctt    900
gcagttgctt tggctagtac atggcttgag aagcaggggc ataaggacag gataccactc    960
aatcgtactg atcccctacc agatcatttt attagaggtc tatcaaatgc ttgtttgcaa   1020
gggcgagcac agattgttcc agattcacga gtgaattcag gagcggccag aaattcttct   1080
ttggtttct atttggatgg ggctcacagt cctgaaagta tggaaatatg tgccaagtgg    1140
ttttcccatg tcactaatga tgataaaaga ataccatctt ccacagagca gtctcagagt   1200
tcgaagtctc taaagatcct tctgttcaat tgcatgtccg tgagagatcc tatgagactg   1260
cttccgcatc tcctggatgc ctcaactcaa aatggagtcc actttgatct ggccctattt   1320
gtaccaaatc aatcgcaata caacaagctt ggttctagta catcagcacc tgctgagcct   1380
gaacaaatcg atttgtcatg gcagttgtca ctccaaacag tgtgggagaa gttacttcag   1440
gataaaggaa tagatagtgc aaattccagt gacaatagta aagtttttgc atctcttcca   1500
cttgcgatcg agtggctaag gaagaatgcc caagaaaacg gatctacttc ttttcagaac   1560
caggtcttgg ttactggctc cctgcatctt gttggtgatg tcttgaggct tattaagaag   1620
tga                                                                 1623
```

<210> SEQ ID NO 4
<211> LENGTH: 539
<212> TYPE: PRT
<213> ORGANISM: Panicum virgatum

<400> SEQUENCE: 4

```
Met Arg Ser His Pro Pro Leu Ala Ala His Leu Arg Arg Leu Leu Leu
1               5                   10                  15

Leu Ser Pro Ser Thr Gln Leu Thr His Arg Ala Ala Met Ala Ser Thr
            20                  25                  30

Ala Ala Val Ala Arg Ala Gly Ala Val Ala Pro Ala Glu Tyr Glu Glu
        35                  40                  45

Val Leu Gly Arg Leu Ser Ser Leu Ile Thr Gln Lys Val Arg Ala His
    50                  55                  60

Ser Gly Asn Arg Gly Asn Gln Trp Asp Leu Met Ala His Tyr Val Lys
```

```
                65                  70                  75                  80
Ile Leu Glu Leu Glu Pro Ile Ala Arg Met Lys Val Ile His Val
                    85                  90                  95
Ala Gly Thr Lys Gly Lys Gly Ser Thr Cys Thr Phe Thr Glu Ser Ile
                    100                 105                 110
Leu Arg Ser Cys Gly Phe His Thr Gly Leu Phe Thr Ser Pro His Leu
                    115                 120                 125
Met Asp Val Arg Glu Arg Phe Arg Leu Asp Gly Val Asp Ile Ser Glu
            130                 135                 140
Glu Lys Phe Leu Lys Tyr Phe Trp Trp Cys Trp Asn Lys Leu Lys Glu
145                 150                 155                 160
Lys Thr Asp Asp Ile Pro Met Pro Ala Tyr Phe Arg Phe Leu Ala
                    165                 170                 175
Leu Leu Ala Phe Lys Ile Phe Ser Ala Glu Gln Val Asp Val Ala Val
                    180                 185                 190
Leu Glu Val Gly Leu Gly Gly Lys Phe Asp Ala Thr Asn Val Val Glu
                    195                 200                 205
Ala Pro Val Val Cys Gly Val Ser Ser Leu Gly Tyr Asp His Met Glu
            210                 215                 220
Ile Leu Gly Asn Thr Leu Gly Glu Ile Ala Gly Glu Lys Ala Gly Ile
225                 230                 235                 240
Phe Lys Lys Gly Val Pro Ala Tyr Thr Ala Pro Gln Gln Glu Ala
                    245                 250                 255
Met Val Ala Leu Lys Gln Arg Ala Ser Glu Leu Gly Ile Pro Leu Gln
                    260                 265                 270
Val Ala Asp Pro Leu Val Pro Tyr His Leu Lys Gly Gln Leu Leu Gly
                    275                 280                 285
Leu Asn Gly Glu His Gln Tyr Ile Asn Ala Gly Leu Ala Val Ala Leu
            290                 295                 300
Ala Ser Thr Trp Leu Glu Lys Gln Gly His Lys Asp Arg Ile Pro Leu
305                 310                 315                 320
Asn Arg Thr Asp Pro Leu Pro Asp His Phe Ile Arg Gly Leu Ser Asn
                    325                 330                 335
Ala Cys Leu Gln Gly Arg Ala Gln Ile Val Pro Asp Ser Arg Val Asn
                    340                 345                 350
Ser Gly Ala Ala Arg Asn Ser Ser Leu Val Phe Tyr Leu Asp Gly Ala
                    355                 360                 365
His Ser Pro Glu Ser Met Glu Ile Cys Ala Lys Trp Phe Ser His Val
            370                 375                 380
Thr Asn Asp Asp Lys Arg Ile Pro Ser Ser Thr Glu Gln Ser Gln Ser
385                 390                 395                 400
Ser Lys Ser Leu Lys Ile Leu Leu Phe Asn Cys Met Ser Val Arg Asp
                    405                 410                 415
Pro Met Arg Leu Leu Pro His Leu Leu Asp Ala Ser Thr Gln Asn Gly
                    420                 425                 430
Val His Phe Asp Leu Ala Leu Phe Val Pro Asn Gln Ser Gln Tyr Asn
            435                 440                 445
Lys Leu Gly Ser Ser Thr Ser Ala Pro Ala Glu Pro Glu Gln Ile Asp
            450                 455                 460
Leu Ser Trp Gln Leu Ser Leu Gln Thr Val Trp Glu Lys Leu Leu Gln
465                 470                 475                 480
Asp Lys Gly Ile Asp Ser Ala Asn Ser Ser Asp Ser Lys Val Phe Ala
                    485                 490                 495
```

```
Ser Leu Pro Leu Ala Ile Glu Trp Leu Arg Lys Asn Ala Gln Glu Asn
                500                 505                 510

Gly Ser Thr Ser Phe Gln Asn Gln Val Leu Val Thr Gly Ser Leu His
            515                 520                 525

Leu Val Gly Asp Val Leu Arg Leu Ile Lys Lys
            530                 535

<210> SEQ ID NO 5
<211> LENGTH: 19
<212> TYPE: DNA
<213> ORGANISM: Artificial sequence
<220> FEATURE:
<223> OTHER INFORMATION: Primer

<400> SEQUENCE: 5
aagcaggggc ataaggaca                                                  19

<210> SEQ ID NO 6
<211> LENGTH: 21
<212> TYPE: DNA
<213> ORGANISM: Artificial sequence
<220> FEATURE:
<223> OTHER INFORMATION: Primer

<400> SEQUENCE: 6
atcgatttgt tcaggctcag c                                               21

<210> SEQ ID NO 7
<211> LENGTH: 4704
<212> TYPE: DNA
<213> ORGANISM: Arabidopsis thaliana

<400> SEQUENCE: 7
atgtttgcag tttcgatagt acctcgaacc acatcgtgcc gtttgagctc tgcctttctc      60
tgtcaactct cgattcctct cactcttcgg ctccaccatc actaccaaca ccaccagcct     120
cacctaccat ctcctctctc ttttcaggtt tccctttctc tttcgctctc tgtctctcat     180
attccgagaa tctcggagtt tcggcatctc tgatattctc tcttattcgt gtttcagatt     240
cattcgttaa gaaagcagat cgacatggca gctcaaggtt tgttattgat tttcttattc     300
ttctctagct cttcctcact tgatgataac agtaatcgaa tcgagttcac ttgtttgttt     360
ttgttggtga caggaggtga ttcatatgag gaagcgttgg ctgctttgtc gtctttgatc     420
acgaaacgaa gtcgtgctga taagagcaat aaaggggatc gctttgagtt agtctttgat     480
tatctcaagg tttctctttt cgattggatt ctcgtagagt tttgaatatt tattgcacct     540
tttgttttat tttctgattg aatacgcttc ttgtaattaa tttggcagct acttgacctg     600
gaagaagaca ttttaaagat gaatgttatt catgtcgctg gtaccaaagg caaggtaaca     660
acaacaactt tacttttct ggtaaagctc aataaatgat actaaatcat ctattgtcaa     720
tattaggagt tggttttgtt actttagtta gttagttaga tatcttctga attcgtgtca     780
gcttctacac tagttgtgac cgttacgtcc ttatgactgc tttgtcagaa gaagcctaag     840 gttttgctc tgtggggatt agagatacgt ttctggactg agtcatcttg agcttttttc     900
caatttgagt gagtgcgaga agaacattgg ttttgagatc cttgcatgct ggagatgcg     960 tatggtttca tctgatggag tgtcagtttt gcaaaagttg ctactttaat cttgactcat    1020
atcacttatg tgatagtaga tttgggatag cacaaaggaa attgttatga aactagtact    1080
tgcttacttt ttgattcaaa ccttcagtga acttgtttga tgaaagtggt tcattgttag    1140
```

```
catggctgat tactatctga tccagcacct aacagtattc cttttttgttt cttatgtggc    1200 atgaagggat ccacatgtac ctttacagag tctattattc gaaactatgg ctttcgaact    1260
ggactcttca cttcacctca cctcattgat gtccgggaaa gatttcgttt ggatgggtaa    1320 gttttttctaa gtttgctgaa aattttgaga aaataaatat atagttaccg gccctcatat    1380
aatcaggaac caacaatact tcgctagcat aatcctgttt ttcactcttc tttactgaga    1440
aatgcttata ttcgcttaat ctgatatgtt ctatttattg ctgcagtgtg gacataagtg    1500
aagagaaatt tttgggatat ttctggtggt gctataacag gctcaaggta tgttcgtgag    1560
aaaagaaggt tcagctattt gattcatttg ttttgaactc aatatctgta gtttggttat    1620
ctcgattgac tagtagacta gttgttagta acgttctgta aacttggaat cttagtgatg    1680
aaagccatat agaatgtgat aaacatgtaa acaccccttt ttcatgaaca cttattttgt    1740
ttttccattt tagcttaaaa ccatggtgtt cagtactgaa gttttggtac ttagagaaat    1800
tgtattattg gaactatttt catcgagggg gtggtgatgc ggtagagctc atgtatagtg    1860
tcttccctgt atcttgttga agtcaccttt tgttttgcgg tctgagtatt tcatgatatg    1920
aactcataag aatttacaat ggtgtgcata gttgcaaatt aagatacatg ctttagtttt    1980
ttactcaaaa tacaaggttg ccgactattt gatttgcagg agagaactaa cgaggagata    2040
ccaatgccta catatttccg cttccttgca ttgctagctt ttaaaatatt tgctgcagaa    2100
gaggtttgat accagtctttt accttggctg actattttc ttactcagtg acatgataga    2160
taaactaaca tcatgttctc tttattgata taaggggttc tgcttttttgc ttctttatgc    2220 aggtagatgc tgctatattg gaggttggat taggtggaaa gtttgatgcc accaatgcgg    2280
tatgtttgac cttttttttcag ctgaaatgct tttgtctgaa catatccctt tacctaacat    2340
cctgaattac gaaagaggaa agttatatga aaaccttaga taagatcgga acccaaatcc    2400
ttaactaatc gtatactgaa gtatagtaat atcctcaaaa gactccaatt actaaaatat    2460
gaataacttt caggacgggt gtaagtagag cttcttgtgc ctaattaagt tctcatggtg    2520
atttactact gacttgttac aggttcagaa acctgtggta tgtggtatttt cttcactcgg    2580 atatgaccac atggaaattc taggtttgta actggaatct tctcagcatg ccatacgaat    2640
attgtccatg cctctactct ttttttttca tatcagaact ttaaagcatg aagtctatgc    2700
ttgcattaaa tgagcagaca tattttgagt tacatttcgt ttttataatt tctttcttat    2760
ctgtggaatg catcacaggt gatacacttg gaaaaattgc tggtgagaag gctggaattt    2820
tcaaggtggc tataactctg ttaaattgta acttagcaat attctccata gttgcctcat    2880
cttcattgtt catatttcag cttggagttc cagctttcac agtgccccaa cctgatgaag    2940
ccatgcgtgt ccttgaagag aaagcttccg aaacagaagt acgctcaatt ttaattaatg    3000
agcactatgg tcattaaatt tggtagacaa tgtatgtaca tatatatagt ttctgtttat    3060
gtcctgcgtg gttgattgta gtgctttaga tctaccattc ttttacggta aataatgaga    3120
aatcaatgtg tccacaaata tgtgcattag ttatagtccc attctagctt ttttgatctg    3180
tgaaagtaag agtgggtgct tttgcggaga tgattcaaca ttctattgac agatcttgaa    3240
agtaggtaag tgtttttgag aagctttaac atcatattga caggtgaatc tcgaagtggt    3300
gcagccacta accgcaaggc tgttaagtgg tcagaaactt gggcttgatg gggaacacca    3360
atatgtcaat gctggtctag cagtttcgct tgcctctatc tggcttcagc aaattggtaa    3420
actagaagtt ccgagtcgga ctcagatggt aaaatgctct tttccgtctt tacgcttact    3480
```

```
cacagtttgt atcttggccc ttctctcatt tgtgaatttc atccctttt  cgacattctt      3540 cttcgaatta gagtattctg cctgagaaat tcatcaaagg gttagctaca gcgagtttgc      3600
aaggacgagc acaggtcgtc cctgatcaat atactgaatc tcggacttca ggagatctag      3660
tattttatct ggatggagct cacagtccag aaagcatgga agcatgcgcc aaatggtttt      3720
cggttgcggt taagggagac aaccagtcag ggagttcagg acatttggtt aatggctctg      3780
caggatcctc tcatgataaa tggtcaaatg aaacctgtga acaggtaagg tccgggtttc      3840
gtggtctgtc ttggatttat aaatcatatg agagactgaa tgaattcaca ggaaaaggat      3900
tgggtttaga gtatcttctt atgtctatgc ttgtctttct ctagtttctc agcttttaa       3960 atatctgaac gagagcatct ggctgctttg cagatattgt tgttcaattg tatgtcagtt      4020
cgggacccaa atctactgct tccacatcta agaatatgt gcgcaaaata cggtaagttc       4080
gtgagccctt gtgtcttcaa aagacaaaat gtagaaacag aaaacttggc ctgaggtaaa      4140
acggatagtt agagaagctg aataatggtt gatgtaggtg tcaatttcaa gaaggcattg      4200
tttgtaccaa acatgtcggt gtatcataag gttggtacag cagctgattt gccagagaat      4260
gatccacagg ttgacttgtc atggcagttc acacttcaga agtgtgggaa agccttgtg       4320 cagagtgaaa gaggtagtcc taaatcttta tgatcatgga ataaaatcaa cacgtcacaa      4380
tcgttatctc aacttaactc ttcttgtttg gtcacgcaga tggagaaaaa gatggtgaaa      4440 gtgatgaaa cagtgaggtg tttacttcac tacccatggc aataaaatgt ctaagggaca      4500
ctgtacatga gagtagctca gccacacgtt tccaggtata aacaaaccc cttttctga      4560 acgagtgttc aatccggatt ttcagttttc ggataatgaa tagttagcaa tgtaagatgg      4620
ctcagggact gtttgtgtgt gcaggtcctt gtaactggtt cgttacatct tgtgggcgat      4680
gtactgagat taatcagaaa atga                                            4704

<210> SEQ ID NO 8
<211> LENGTH: 4704
<212> TYPE: DNA
<213> ORGANISM: Arabidopsis thaliana

<400> SEQUENCE: 8
atgtttgcag tttcgatagt acctcgaacc acatcgtgcc gtttgagctc tgcctttctc        60
tgtcaactct cgattcctct cactcttcgg ctccaccatc actaccaaca ccaccagcct       120
cacctaccat ctcctctctc ttttcaggtt tccctttctc tttcgctctc tgtctctcat       180
attccgagaa tctcggagtt tcggcatctc tgatattctc tcttattcgt gtttcagatt       240
cattcgttaa gaaagcagat cgacatggca gctcaaggtt tgttattgat tttcttattc       300
ttctctagct cttcctcact tgatgataac agtaatcgaa tcgagttcac ttgtttgttt       360
ttgttggtga caggaggtga ttcatatgag gaagcgttgg ctgctttgtc gtctttgatc       420
acgaaacgaa gtcgtgctga taagagcaat aaaggggatc gctttgagtt agtctttgat       480
tatctcaagg tttctctttt cgattggatt ctcgtagagt tttgaatatt tattgcacct       540
tttgttttat ttctgattg aatacgcttc ttgtaattaa tttggcagct acttgacctg       600
gaagaagaca ttttaaagat gaatgttatt catgtcgctg gtaccaaagg caaggtaaca       660
acaacaactt tacttttct ggtaaagctc aataaatgat actaaatcat ctattgtcaa       720
tattaggagt tggttttgtt actttagtta gttagttaga tatcttctga attcgtgtca       780
gcttctacac tagttgtgac cgttacgtcc ttatgactgc tttgtcagaa gaagcctaag       840 gttttgctc tgtggggatt agagatacgt ttctggactg agtcatcttg agcttttttc        900
```

```
caatttgagt gagtgcgaga agaacattgg ttttgagatc cttgcatgct tggagatgcg    960
tatggtttca tctgatggag tgtcagtttt gcaaaagttg ctactttaat cttgactcat   1020
atcacttatg tgatagtaga tttgggatag cacaaaggaa attgttatga aactagtact   1080
tgcttacttt ttgattcaaa ccttcagtga acttgtttga tgaaagtggt tcattgttag   1140
catggctgat tactatctga tccagcacct aacagtattc cttttttgttt cttatgtggc   1200 atgaagggat ccacatgtac ctttacagag tctattattc gaaactatgg ctttcgaact   1260
ggactcttca cttcacctca cctcattgat gtccgggaaa gatttcgttt ggatgggtaa   1320 gttttttctaa gtttgctgaa aattttgaga aaataaatat atagttaccg gccctcatat   1380
aatcaggaac caacaatact tcgctagcat aatcctgttt ttcactcttc tttactgaga   1440
aatgcttata ttcgcttaat ctgatatgtt ctatttattg ctgcagtgtg gacataagtg   1500
aagagaaatt tttgggatat ttctggtggt gctataacag gctcaaggta tgttcgtgag   1560
aaaagaaggt tcagctattt gattcatttg ttttgaactc aatatctgta gtttggttat   1620
ctcgattgac tagtagacta gttgttagta acgttctgta aacttggaat cttagtgatg   1680
aaagccatat agaatgtgat aaacatgtaa aacacccttt ttcatgaaca cttattttgt   1740 ttttccatt tagcttaaaa ccatggtgtt cagtactgaa gttttggtac ttagagaaat   1800
tgtattattg gaactatttt catcgagggg gtggtgatgc ggtagagctc atgtatagtg   1860
tcttccctgt atcttgttga agtcaccttt tgttttgcgg tctgagtatt tcatgatatg   1920
aactcataag aatttacaat ggtgtgcata gttgcaaatt aagatacatg ctttagtttt   1980
ttactcaaaa tacaaggttg ccgactattt gatttgcagg agagaactaa cgaggagata   2040
ccaatgccta catatttccg cttccttgca ttgctagctt ttaaaatatt tgctgcagaa   2100
gaggtttgat accagtcttt accttggctg actattttc ttactcagtg acatgataga   2160
taaactaaca tcatgttctc tttattgata taaggggttc tgcttttttgc ttctttatgc   2220 aggtagatgc tgctatattg gaggttggat taggtggaaa gtttgatgcc accaatgcgg   2280
tatgtttgac cttttttcag ctgaaatgct tttgtctgaa catatcccctt tacctaacat   2340 cctgaattac gaaagaggaa agttatatga aaaccttaga taagatcgga acccaaatcc   2400
ttaactaatc gtatactgaa gtatagtaat atcctcaaaa gactccaatt actaaaatat   2460
gaataacttt caggacgggt gtaagtagag cttcttgtgc ctaattaagt tctcatggtg   2520
atttactact gacttgttac aggttcagaa acctgtggta tgtggtattt cttcactcgg   2580
atatgaccac atggaaaattc taggtttgta actggaatct tctcagcatg ccatacgaat   2640
attgtccatg cctctactct ttttttttttca tatcagaact ttaaagcatg aagtctatgc   2700
ttgcattaaa tgagcagaca tattttgagt tacatttcgt tttataatt tctttcttat   2760 ctgtggaatg catcacaggt gatacacttg aaaaattgc tggtgagaag gctggaattt   2820
tcaaggtggc tataactctg ttaaattgta acttagcaat attctccata gttgcctcat   2880
cttcattgtt catatttcag cttggagttc cagctttcac agtgccccaa cctgatgaag   2940
ccatgcgtgt ccttgaagag aaagcttccg aaacagaagt acgctcaatt ttaattaatg   3000
agcactatgg tcattaaatt tggtagacaa tgtatgtaca tatatatagt ttctgtttat   3060
gtcctgcgtg gttgattgta gtgctttaga tctaccattc ttttacggta aataatgaga   3120
aatcaatgtg tccacaaata tgtgcattag ttatagtccc attctagctt ttttgatctg   3180
tgaaagtaag agtgggtgct tttgcggaga tgattcaaca ttctattgac agatcttgaa   3240
```

```
agtaggtaag tgtttttgag aagctttaac atcatattga caggtgaatc tcgaagtggt      3300
gcagccacta accgcaaggc tgttaagtgg tcagaaactt gggcttgatg gggaacacca      3360
atatgtcaat gctggtctag cagtttcgct tgcctctatc tggcttcagc aaattggtaa      3420
actagaagtt ccgagtcgga ctcagatggt aaaatgctct tttccgtctt tacgcttact      3480
cacagtttgt atcttggccc ttctctcatt tgtgaatttc atccctttt cgacattctt       3540
cttcgaatta gagtattctg cctgagaaat tcatcaaagg gttagctaca gcgagtttgc      3600
aaggacgagc acaggtcgtc cctgatcaat atactgaatc tcggacttca ggagatctag      3660
tattttatct ggatggagct cacagtccag aaagcatgga agcatgcgcc aaatggtttt      3720
cggttgcggt taagggagac aaccagtcag ggagttcagg acatttggtt aatggctctg      3780
caggatcctc tcatgataaa tggtcaaatg aaacctgtga acaggtaagg tccgggtttc      3840
gtggtctgtc ttggatttat aaatcatatg agagactgaa tgaattcaca ggaaaaggat      3900
tgggtttaga gtatcttctt atgtctatgc ttgtctttct ctagtttctc agcttttaa       3960
atatctgaac gagagcatct ggctgctttg cagatattgt tgttcaattg tatgtcagtt      4020
cgggacccaa atctactgct tccacatcta aagaatatgt gcgcaaaata cggtaagttc      4080
gtgagcccct gtgtcttcaa aagacaaaat gtagaaacag aaaacttggc ctgaggtaaa      4140
acggatagtt agagaagctg aataatggtt gatgtaggtg tcaatttcaa gaaggcattg      4200
tttgtaccaa acatgtcggt gtatcataag gttggtacag cagctgattt gccagagaat      4260
gatccacagg ttgacttgtc atggcagttc acacttcaga aagtgtggga aagccttgtg      4320
cagagtgaaa gaggtagtcc taaatcttta tgatcatgga ataaaatcaa cacgtcacaa      4380
tcgttatctc aacttaactc ttcttgtttg gtcacgcaga tggagaaaaa gatggtgaaa      4440
gtgatggaaa cagtgaggtg tttacttcac tacccatggc aataaaatgt ctaagggaca      4500
ctgtacatga gagtagctca gccacacgtt tccaggtata aaacaaaccc cttttttctga     4560
acgagtgttc aatccgggtt ttcagttttc ggataatgaa tagttagcaa tgtaagatgg      4620
ctcagggact gtttgtgtgt gcaggtcctt gtaactggtt cgttacatct tgtgggcgat      4680
gtactgagat taatcagaaa atga                                             4704
```

<210> SEQ ID NO 9
<211> LENGTH: 4704
<212> TYPE: DNA
<213> ORGANISM: Arabidopsis thaliana

<400> SEQUENCE: 9

```
atgtttgcag tttcgatagt acctcgaacc acatcgtgcc gtttgagctc tgcctttctc       60
tgtcaactct cgattcctct cactcttcgg ctccaccatc actaccaaca ccaccagcct      120
cacctaccat ctcctctctc ttttcaggtt tccctttctc tttcgctctc tgtctctcat      180
attccgagaa tctcggagtt tcggcatctc tgatattctc tcttattcgt gtttcagatt      240
cattcgttaa gaaagcagat cgacatggca gctcaaggtt tgttattgat tttcttattc      300
ttctctagct cttcctcact tgatgataac agtaatcgaa tcgagttcac ttgtttgttt      360
ttgttggtga caggaggtga ttcatatgag aagcgttgg ctgctttgtc gtctttgatc       420
acgaaacgaa gtcgtgctga taagagcaat aaaggggatc gctttgagtt agtctttgat      480
tatctcaagg tttctctttt cgattggatt ctcgtagagt tttgaatatt tattgcacct      540
tttgttttat tttctgattg aatacgcttc ttgtaattaa tttggcagct acttgacctg      600
gaagaagaca ttttaaagat gaatgttatt catgtcgctg gtaccaaagg caaggtaaca      660
```

```
acaacaactt tactttttct ggtaaagctc aataaatgat actaaatcat ctattgtcaa      720
tattaggagt tggttttgtt actttagtta gttagttaga tatcttctga attcgtgtca      780
gcttctacac tagttgtgac cgttacgtcc ttatgactgc tttgtcagaa gaagcctaag      840 gttttttgctc tgtggggatt agagatacgt ttctggactg agtcatcttg agctttttc      900 caatttgagt gagtgcgaga agaacattgg ttttgagatc cttgcatgct tggagatgcg      960
tatggtttca tctgatggag tgtcagtttt gcaaaagttg ctactttaat cttgactcat     1020
atcacttatg tgatagtaga tttgggatag cacaaaggaa attgttatga aactagtact     1080
tgcttacttt ttgattcaaa ccttcagtga acttgtttga tgaaagtggt tcattgttag     1140
catggctgat tactatctga tccagcacct aacagtattc cttttgttt cttatgtggc      1200 atgaagggat ccacatgtac ctttacagag tctattattc gaaactatgg ctttcgaact     1260
ggactcttca cttcacctca cctcattgat gtccgggaaa gatttcgttt ggatgggtaa     1320
gtttttctaa gtttgctgaa aattttgaga aaataaatat atagttaccg ccctctatat     1380
aatcaggaac caacaatact tcgctagcat aatcctgttt ttcactcttc tttactgaga     1440
aatgcttata ttcgcttaat ctgatatgtt ctatttattg ctgcagtgtg gacataagtg     1500
aagagaaatt tttgggatat ttctggtggt gctataacag gctcaaggta tgttcgtgag     1560
aaaagaaggt tcagctattt gattcatttg tttgaactc aatatctgta gtttggttat      1620
ctcgattgac tagtagacta gttgttagta acgttctgta aacttggaat cttagtgatg     1680
aaagccatat agaatgtgat aaacatgtaa aacacccttt ttcatgaaca cttattttgt     1740
ttttccattt tagcttaaaa ccatggtgtt cagtactgaa gttttggtac ttagagaaat     1800
tgtattattg gaactatttt catcgagggg gtggtgatgc ggtagagctc atgtatagtg     1860
tcttccctgt atcttgttga agtcaccttt tgttttgcgg tctgagtatt tcatgatatg     1920
aactcataag aatttacaat ggtgtgcata gttgcaaatt aagatacatg ctttagtttt     1980
ttactcaaaa tacaaggttg ccgactattt gatttgcagg agagaactaa cgaggagata     2040
ccaatgccta catatttccg cttccttgca ttgctagctt ttaaaatatt tgctgcagaa     2100
gaggtttgat accagtcttt accttggctg actattttc ttactcagtg acatgataga     2160
taaactaaca tcatgttctc tttattgata taaggggttc tgcttttgc ttctttatgc      2220 aggtagatgc tgctatattg gaggttggat taggtggaaa gtttgatgcc accaatgcgg     2280
tatgtttgac cttttttcag ctgaaatgct tttgtctgaa catatccctt tacctaacat     2340
cctgaattac gaaagaggaa agttatatga aaaccttaga taagatcgga acccaaatcc     2400
ttaactaatc gtatactgaa gtatagtaat atcctcaaaa gactccaatt actaaaatat     2460
gaataacttt caggacgggt gtaagtagag cttcttgtgc ctaattaagt tctcatggtg     2520
atttactact gacttgttac aggttcagaa acctgtggta tgtggtattt cttcactcgg     2580
atatgaccac atgaaaattc taggtttgta actggaatct tctcagcatg ccatacgaat     2640
attgtccatg cctctactct ttttttttca tatcagaact ttaaagcatg aagtctatgc     2700
ttgcattaaa tgagcagaca tatttttgagt tacatttcgt ttttataatt tctttcttat    2760
ctgtggaatg catcacaggt gatacacttg gaaaaattgc tggtgagaag ctggaatttt    2820
tcaaggtggc tataactctg ttaaattgta acttagcaat attctccata gttgcctcat     2880
cttcattgtt catatttcag cttggagttc cagcttccac agtgccccaa cctgatgaag     2940
ccatgcgtgt ccttgaagag aaagcttccg aaacagaagt acgctcaatt ttaattaatg     3000
```

```
agcactatgg tcattaaatt tggtagacaa tgtatgtaca tatatatagt ttctgtttat    3060
gtcctgcgtg gttgattgta gtgctttaga tctaccattc ttttacggta aataatgaga    3120
aatcaatgtg tccacaaata tgtgcattag ttatagtccc attctagctt ttttgatctg    3180
tgaaagtaag agtgggtgct tttgcggaga tgattcaaca ttctattgac agatcttgaa    3240
agtaggtaag tgtttttgag aagctttaac atcatattga caggtgaatc tcgaagtggt    3300
gcagccacta accgcaaggc tgttaagtgg tcagaaactt gggcttgatg gggaacacca    3360
atatgtcaat gctggtctag cagtttcgct tgcctctatc tggcttcagc aaattggtaa    3420
actagaagtt ccgagtcgga ctcagatggt aaaatgctct tttccgtctt tacgcttact    3480
cacagtttgt atcttggccc ttctctcatt tgtgaatttc atccctttt  cgacattctt    3540 cttcgaatta gagtattctg cctgagaaat tcatcaaagg gttagctaca gcgagtttgc    3600
aaggacgagc acaggtcgtc cctgatcaat atactgaatc tcggacttca ggagatctag    3660
tattttatct ggatggagct cacagtccag aaagcatgga agcatgcgcc aaatggtttt    3720
cggttgcggt taagggagac aaccagtcag ggagttcagg acatttggtt aatggctctg    3780
caggatcctc tcatgataaa tggtcaaatg aaacctgtga acaggtaagg tccgggtttc    3840
gtggtctgtc ttggatttat aaatcatatg agagactgaa tgaattcaca ggaaaaggat    3900
tgggtttaga gtatcttctt atgtctatgc ttgtctttct ctagtttctc agcttttaa     3960 atatctgaac gagagcatct ggctgctttg cagatattgt tgttcaattg tatgtcagtt    4020
cgggacccaa atctactgct tccacatcta agaatatgt  gcgcaaaata cggtaagttc    4080
gtgagcccct tgtgtcttca aagacaaaat gtagaaacag aaaacttggc ctgaggtaaa    4140
acggatagtt agagaagctg aataatggtt gatgtaggtg tcaatttcaa gaaggcattg    4200
tttgtaccaa acatgtcggt gtatcataag gttggtacag cagctgattt gccagagaat    4260
gatccacagg ttgacttgtc atggcagttc acacttcaga aagtgtggga aagccttgtg    4320
cagagtgaaa gaggtagtcc taaatcttta tgatcatgaa ataaaatcaa cacgtcacaa    4380
tcgttatctc aacttaactc ttcttgtttg gtcacgcaga tggagaaaaa gatggtgaaa    4440
gtgatggaaa cagtgaggtg tttacttcac tacccatggc aataaaatgt ctaagggaca    4500
ctgtacatga gagtagctca gccacacgtt tccaggtata aacaaaccc  cttttctga     4560 acgagtgttc aatccgggtt ttcagttttc ggataatgaa tagttagcaa tgtaagatgg    4620
ctcagggact gttttgtgtgt gcaggtcctt gtaactggtt cgttacatct tgtgggcgat    4680
gtactgagat taatcagaaa atga                                           4704
```

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10

```
ggctttcgaa ctggactctt c                                              21
```

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ctgaccactt aacagccttg c							21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cgatggttct cttctgcagt c							21

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ggcccaagtt gtttgtatca tc						22

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ctctttctgc ggttcagaca c							21

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
tgttaaggtc aaaacataaa ctccat					26

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
tgttaaggtc aaaacataaa ctccat					26

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
ggaaagattt cgtttggatg g							21

<210> SEQ ID NO 18
<211> LENGTH: 20
<212> TYPE: DNA

```
<213> ORGANISM: Artificial Sequence
<220> FEATURE:
<223> OTHER INFORMATION: Primer

<400> SEQUENCE: 18
ggggcttgac catacactga                                             20

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
gcaaagaaga agagaagagt ttcg                                         24

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
ggctgaatga agttctcgat ggacag                                       26

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
cagtacatca tggaaacgtc agc                                          23

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
cactggcacg gtgtgaga                                                18

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
cttctccagg aattgagcat g                                            21

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
gtaaccttcc tgaaaacaga gca                                          23
```

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
gtcttcctta atacctgggc ac                                      22

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
gttacaaagg tgcacttgga ttac                                    24

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tagatccact tgcagggaga tt                                      22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tcgtaaaaca tgccgtgaga                                         20

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
taatggcatg gctcgcag                                           18

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
gattcgagct tcacgagatc a                                       21

<210> SEQ ID NO 31
<211> LENGTH: 24
<212> TYPE: DNA
<213> ORGANISM: Artificial Sequence
<220> FEATURE:

```
<223> OTHER INFORMATION: Primer

<400> SEQUENCE: 31
gtcatcgtat cagagagctt tgtt                                       24

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ccatcttgtt ccaaaacttg c                                          21

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
tgggcttgtg gagcattac                                             19

<210> SEQ ID NO 34
<211> LENGTH: 17
<212> TYPE: DNA
<213> ORGANISM: Artificial Sequence
<220> FEATURE:
<223> OTHER INFORMATION: Primer

<400> SEQUENCE: 34
catcggaatc gcggaac                                               17

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
acgtctccca cactgatttc                                            20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
accatcttcc acttgaaccc                                            20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ccggaacaaa tggtggag                                              18
```

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
ccgcttcaga aacctaaaca ag        22

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
cctgggcatg agattgct        18

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
ttaaggattt gggttccgat c        21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
attggaggtt ggattaggtg g        21

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
ggagggttct cacttctcat g        21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ttcaagcttg tcacgatttc c        21

<210> SEQ ID NO 44
<211> LENGTH: 21
<212> TYPE: DNA
<213> ORGANISM: Artificial Sequence
<220> FEATURE:
<223> OTHER INFORMATION: Primer

```
<400> SEQUENCE: 44
tgatcccttc aaaacgatca c                                      21

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
tctcttgtca ctaacattgc tacactt                                27

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
ttttctgatt aatctcagta catcgc                                 26

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
tgacatacaa ttgaacaaca atatc                                  25

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
ctgcaggtcc accacattg                                         19

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
gaaaacgaac ttgtttactt tggc                                   24

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
acgagagcct ggcactggag aag                                    23

<210> SEQ ID NO 51
<211> LENGTH: 21
```

```
<212> TYPE: DNA
<213> ORGANISM: Artificial Sequence
<220> FEATURE:
<223> OTHER INFORMATION: Primer

<400> SEQUENCE: 51
ggtaatacgg ccatcttcag g                                        21

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
cattcaccta gaacgatgac tttct                                    25

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gtgtctcctg ggaactctgg                                          20

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
gctattgaca gtgaagcacc tagc                                     24

<210> SEQ ID NO 55
<211> LENGTH: 26
<212> TYPE: DNA
<213> ORGANISM: Artificial Sequence
<220> FEATURE:
<223> OTHER INFORMATION: Primer

<400> SEQUENCE: 55
catcaactaa aactttcaca cctttg                                   26

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
catgaaccct tggtgcatc                                           19

<210> SEQ ID NO 57
<211> LENGTH: 23
<212> TYPE: DNA
<213> ORGANISM: Artificial Sequence
<220> FEATURE:
<223> OTHER INFORMATION: Primer

<400> SEQUENCE: 57
```

-continued tatcttcagg cttcttggtc aaa                                                    23

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
cctcctctgg cttcttggt                                                         19

<210> SEQ ID NO 59
<211> LENGTH: 24
<212> TYPE: DNA
<213> ORGANISM: Artificial Sequence
<220> FEATURE:
<223> OTHER INFORMATION: Primer

<400> SEQUENCE: 59
gaatgtctct ttcacgatct tcag                                                   24

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
gaaatgtttc tgaaacatcc ttgg                                                   24

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
ctctaagata cttctcttcc acggc                                                  25

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
ggtgcgagat cgaagtagtg a                                                      21

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
gtcgaagaaa tggacagctt g                                                      21

<210> SEQ ID NO 64
<211> LENGTH: 22
<212> TYPE: DNA
<213> ORGANISM: Artificial Sequence

```
<220> FEATURE:
<223> OTHER INFORMATION: Primer

<400> SEQUENCE: 64
ccacagagtt ctctcctcca at                                              22

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
gtgtagtgaa tcctgcctct g                                               21

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
gcgtatgaga cctgaacaag ag                                              22

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
caataccaat tcttggtgtt tttg                                            24

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
gctagacgag tgttatccat gg                                              22

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
gcagtacctt tcatgaacaa caat                                            24
```